US006673356B1

(12) United States Patent
Reed et al.

(10) Patent No.: US 6,673,356 B1
(45) Date of Patent: Jan. 6, 2004

(54) COMPOUNDS AND METHODS FOR THE DIAGNOSIS AND TREATMENT OF EHRLICHIA INFECTION

(75) Inventors: Steven G. Reed, Bellevue, WA (US); Michael J. Lodes, Seattle, WA (US); Raymond L. Houghton, Bothell, WA (US); Patricia D. McNeill, Des Moines, WA (US)

(73) Assignee: Corixa Corporation, Seattle, WA (US)

( * ) Notice: Subject to any disclaimer, the term of this patent is extended or adjusted under 35 U.S.C. 154(b) by 66 days.

(21) Appl. No.: 09/693,542

(22) Filed: Oct. 20, 2000

Related U.S. Application Data

(63) Continuation-in-part of application No. 09/566,617, filed on May 8, 2000, and a continuation-in-part of application No. 09/295,028, filed on Apr. 20, 1999, and a continuation-in-part of application No. 09/159,469, filed on Sep. 23, 1998, and a continuation-in-part of application No. 09/106,582, filed on Jun. 29, 1998, and a continuation-in-part of application No. 08/975,762, filed on Nov. 20, 1997, and a continuation-in-part of application No. 08/821,324, filed on Mar. 21, 1997, and a continuation-in-part of application No. PCT/US98/05695, filed on Mar. 23, 1998, and a continuation-in-part of application No. PCT/US99/14793, filed on Jun. 29, 1999.

(51) Int. Cl.[7] .......................... A61K 39/02; C12Q 1/68; C07H 21/04

(52) U.S. Cl. ....................... 424/234.1; 435/6; 536/23.7; 536/24.32; 536/24.33

(58) Field of Search .......................... 424/234.1; 435/6; 536/23.7, 24.32, 24.33

(56) References Cited

FOREIGN PATENT DOCUMENTS

| | | |
|---|---|---|
| WO | WO 96/39484 | 12/1986 |
| WO | WO 98/14584 | 4/1998 |
| WO | WO 98/42740 | 10/1998 |
| WO | WO 98/49313 | 11/1998 |
| WO | WO 00/00615 | 1/2000 |

OTHER PUBLICATIONS

Database TrEMBL Accession No. 085170, Nov. 1, 1998.

Database EMBL Accession No. AF100890, Mar. 15, 2000.

Storey et al., "Molecular cloning and sequencing of three granulocytic Ehrlichia genes encoding high–molecular–weight immunoreactive proteins," *Infection and Immunity* *66*(4):1356–1363, Apr. 1998.

Asanovich et al., "Partial Characterization of Cloned Genes Encoding Immunoreactive Proteins of *Ehrlichia equi* and the Agent of Human Granulocytic Ehrlichiosis (HGE)," *Abstracts of the General Meeting of the America Society for Microbiology*: Abstract No. D–22, 1996.

Borodin et al., "Genes Coding for Bacterial RNA Polymerase. III. Use of Modified Method of Sanger for Sequencing C–Terminal Region of rpoB Gene, Intercistron Region, rpoBC Operon, and N–Terminal Region of rpoC Gene of *Pseudomonas putida,*" *Bioorg. Khim. 14*(9):1179–1182, 1988 (English Language Summary provided on p. 1182).

Chang et al., "Molecular Cloning, Sequencing, Deletion, and Overexpression of a Methionine Amionpeptidase Gene from *Saccharomyces cerevisiae,*" *The Journal of Biological Chemistry 267* (12):8007–8009, Apr. 25, 1992.

Dumler et al., "Serologic Cross–Reactions among *Ehrlichia equi, Ehrlichia phagocytophila*, and Human Granulocytic Ehrlichia," *Journal of Clinical Microbiology* *33*(5):1098–1103, 1995.

Fleischmann et al., "Whole–Genome Random Sequencing and Assembly of *Haemophilus influenzae Rd,*" *Science* *269*:496–512, Jul. 28, 1995.

Leyva–vazquez and Setlow, "Cloning and Nucleotide Sequences of the Genes Encoding Triose Phosphate Isomerase, Phosphoglycerate Mutase, and Enolase from *Bacillus subtilis,*" *Journal of Bacteriology* *176*(13):3903–3910, Jul. 1994.

Leyva–vazquez and Setlow, "Cloning and Nucleotide Sequences of the Genes Encoding Triose Phosphate Isomerase, Phosphoglycerate Mutase, and Enolase from *Bacillus subtilis,*" *Journal of Bacteriology* 176 (13):3903–3910, Jul. 1994.

Monastryrskaya et al., "Primary Structure of EcoRI–F Fragment of rpoB, C Genes and Corresponding Fragments of β–and β'–Subunits of RNA Polymerase from *E. Coli,* "*Bioorg. Khim. 6*:1106–1109, 1980 (English Language Summary provided on p. 1109).

Palmer et al., "The Immunoprotective *Anaplasma marginal* Major Surface Protein 2 Is Encoded by a Polymorphic Multigene Family," *Infection and Immunity 62* (9):3808–3816, 1994.

*Primary Examiner*—Rodney P. Swartz
(74) *Attorney, Agent, or Firm*—Kristen K. Walker; Cynthia L. Shumate

(57) ABSTRACT

Compounds and methods for the diagnosis and treatment of Ehrlichia infection, in particular human granulocytic ehrlichiosis, are disclosed. The compounds provided include polypeptides that contain at least one antigenic portion of an Ehrlichia antigen and DNA sequences encoding such polypeptides. Pharmaceutical compositions and vaccines comprising such polypeptides or DNA sequences are also provided. Diagnostic kits containing such polypeptides or DNA sequences and a suitable detection reagent may be used for the detection of Ehrlichia infection in patients and biological samples. Antibodies directed against such polypeptides are also provided.

3 Claims, 5 Drawing Sheets

SEQUENCE LISTING

```
<160> NUMBER OF SEQ ID NOS:  89

<210> SEQ ID NO 1
<211> LENGTH: 1345
<212> TYPE: DNA
<213> ORGANISM: Ehrlichia sp.

<400> SEQUENCE: 1

ttgagcttga gattggttac gagcgcttca agaccaaggg tattagagat agtggtagta     60

aggaagatga agctgataca gtatatctac tagctaagga gttagcttat gatgttgtta    120

ctggtcagac tgataacctt gccgctgctc ttgccaaaac ctccggtaag gatattgttc    180

agtttgctaa ggcggtggag atttctcatt ccgagattga tggcaaggtt tgtaagacga    240

agtcggcggg aactggaaaa aatccgtgtg atcatagcca aaagccgtgt agtacgaatg    300

cgtattatgc gaggagaacg cagaagagta ggagttcggg aaaaacgtct ttatgcgggg    360

acagtgggta tagcgggcag gagctaataa cgggtgggca ttatagcagt ccaagcgtat    420

tccggaattt tgtcaaagac acactacaag gaaatggtag tgagaactgg cctacatcta    480

ctggagaagg aagtgagagt aacgacaacg ccatagccgt tgctaaggac ctagtaaatg    540

aacttactcc tgaagaacga accatagtgg ctgggttact tgctaaaatt attgaaggaa    600

gcgaggttat tgagattagg gccatctctt cgacttcagt tacaatgaat atttgctcag    660

atatcacgat aagtaatatc ttaatgccgt atgtttgtgt tggtccaggg atgagctttg    720

ttagtgttgt tgatggtcac actgctgcaa agtttgcata tcggttaaag gcaggtctga    780

gttataaatt ttcgaaagaa gttacagctt ttgcaggtgg tttttaccat cacgttatag    840

gagatggtgt ttatgatgat ctgccattgc ggcatttatc tgatgatatt agtcctgtga    900

aacatgctaa ggaaaccgcc attgctagat tcgtcatgag gtactttggc ggggaatttg    960

gtgttaggct cgctttttaa ggttgcgacc taaaagcact tagctcgcct tcactccccc   1020
```

-continued

```
ttaagcaata tgatgcacat ttgttgccct acaaatctaa tataaggttt gttgcctata   1080

ctcgtgccga attcggcacg aggaggaagc tgaactcacc catcagtctc tctcatccgt   1140

tggccacctg ctgtccccac ccacccacca aactggtgct tttaatggaa tcagctttaa   1200

aaagaaaaaa atcctccaag taacaaagca ccctataatt attccgcagc tccttgtcct   1260

cggtaatttt aggcttgtgc tgctatcatt acacattaca tggagttagg gagtcatagc   1320

tcttgtgtgg ccaatcagtg ataca                                         1345


<210> SEQ ID NO 2
<211> LENGTH: 1132
<212> TYPE: DNA
<213> ORGANISM: Ehrlichia sp.

<400> SEQUENCE: 2

atttctatat tggtttggat tacagtccag cgtttagcaa gataagagat tttagtataa     60

gggagagtaa cggagagaca aaggcagtat atccatactt aaaggatgga aagagtgtaa    120

agctagagtc acacaagttt gactggaaca cacctgatcc tcggattggg tttaaggaca    180

acatgcttgt agctatggaa ggtagtgttg gttatggtat tggtggtgcc agggttgagc    240

ttgagattgg ttacgagcgc ttcaagacca agggtattag agatagtggt agtaaggaag    300

atgaagctga tacagtatat ctactagcta aggagttagc ttatgatgtt gttactggac    360

agactgataa ccttgctgct gctcttgcta agacctcggg gaaagacatc gttcagtttg    420

ctaaggcggt tggggtttct catcctagta ttgatgggaa ggtttgtaag acgaaggcgg    480

atagctcgaa gaaatttccg ttatatagtg acgaaacgca cacgaagggg gcaaatgagg    540

ggagaacgtc tttgtgcggt gacaatggta gttctacgat aacaaccagt ggtacgaatg    600

taagtgaaac tgggcaggtt tttagggatt ttatcagggc aacgctgaaa gaggatggta    660

gtaaaaactg gccaacttca agcggcacgg gaactccaaa acctgtcacg aacgacaacg    720

ccaaagccgt agctaaagac ctagtacagg agctaacccc tgaagaaaaa accatagtag    780

cagggttact agctaagact attgaagggg gtgaagttgt tgagatcagg gcggtttctt    840

ctacttccgt aatggtcaat gcttgttatg atcttcttag tgaaggttta ggtgttgttc    900

cttatgcttg tgttggtctc ggtggtaact tcgtgggcgt ggttgatgga attcattaca    960

caaaccatct ttaactctga ataccctagt taaggtaagt gaagtaacta ggcaaattag   1020

tgctgcacca ctcgtgaaac aaactacgat cagcgattca ccatacttag taggtccgta   1080

cagtggcttt acgctcttac ccatcatgaa aaatacttgc tatctaggaa tc           1132


<210> SEQ ID NO 3
<211> LENGTH: 554
<212> TYPE: DNA
<213> ORGANISM: Ehrlichia sp.

<400> SEQUENCE: 3

ctactagcta aggagttagc ttatgatgtt gttactgggc agactgataa ccttgctgct     60

gctcttgcca agacttctgg taaagatatt gttcagtttg ctaagactct taatatttct    120

cactctaata tcgatgggaa ggtttgtagg agggaaaagc atgggagtca aggtttgact    180

ggaaccaaag caggttcgtg tgatagtcag ccacaaacgg cgggtttcga ttccatgaaa    240

caaggtttga tggcagcttt aggcgaacaa ggcgctgaaa agtggcccaa aattaacaat    300

ggtggccacg caacaattta tagtagtagc gcaggtccag gaaatgcgta tgctagagat    360

gcatctacta cggtagctac agacctaaca aagctcacta ctgaagaaaa aaccatagta    420
```

```
gcagggttac tagctagaac tattgaaggg ggtgaagttg ttgagattag ggcagtttct    480

tctacttctg tgatggttaa tgcttgttat gatcttctta gtgaaggttt aggtgttgta    540

ccttatgctt gtgt                                                      554
```

<210> SEQ ID NO 4
<211> LENGTH: 559
<212> TYPE: DNA
<213> ORGANISM: Ehrlichia sp.

<400> SEQUENCE: 4

```
atgctgtgaa aattactaac tccactatcg atgggaaggt ttgtaatggt agtagagaga     60

aggggaatag tgctgggaac aacaacagtg ctgtggctac ctacgcgcag actcacacag    120

cgaatacatc aacgtcacag tgtagcggtc tagggaccac tgttgtcaaa caaggttatg    180

gaagtttgaa taagtttgtt agcctgacgg gggttggtga aggtaaaaat tggcctacag    240

gtaagataca cgacggtagt agtggtgtca aagatggtga acagaacggg aatgccaaag    300

ccgtagctaa agacctagta gatcttaatc gtgacgaaaa aaccatagta gcaggattac    360

tagctaaaac tattgaaggg ggtgaagttg ttgagatcag ggcggtttct tctacttctg    420

tgatggttaa tgcttgttat gatcttctta gtgaaggttt aggcgttgtt ccttacgctt    480

gtgtcggtct cggaggtaac ttcgtgggcg ttgttgatgg gcatatcact cctaagcttg    540

cttatagatt aaaggctgg                                                 559
```

<210> SEQ ID NO 5
<211> LENGTH: 201
<212> TYPE: DNA
<213> ORGANISM: Ehrlichia sp.

<400> SEQUENCE: 5

```
agcgcttcaa gaccaagggt attagagata gtggtagtaa ggaagatgaa gctgatacag     60

tatatctact agctaaggag ttagcttatg atgttgttac tggacagact gataaccttg    120

ccgctgctct tgctaaaacc tcggggaaag actttgttca gtttgctaag gccgtggaga    180

tttctaattc tacgattggg g                                              201
```

<210> SEQ ID NO 6
<211> LENGTH: 467
<212> TYPE: DNA
<213> ORGANISM: Ehrlichia sp.

<400> SEQUENCE: 6

```
ggtatatcga tagcctacgt agtcactcct tattattaaa aaggaagacc aagggtatta     60

gagatagtgg aagtaaggaa gatgaagcag atacagtata tctactagct aaggagttag    120

cttatgatgt tgttactggg cagactgata accttgccgc tgctcttgcc aaaacctccg    180

gtaaggactt tgttaaattt gccaatgctg ttgttggaat ttctcacccc gatgttaata    240

agaaggtttg tgcgacgagg aaggacagtg gtggtactag atatgcgaag tatgctgcca    300

cgactaataa gagcagcaac cctgaaacct cactgtgtgg agacgaaggt ggctcgagcg    360

gcacgaataa tacacaagag tttcttaagg aatttgtagc ccaaacccta gtagaaaatg    420

aaagtaaaaa ctggcctact tcaagcggga ctgggttgaa gactaac                  467
```

<210> SEQ ID NO 7
<211> LENGTH: 530
<212> TYPE: DNA

-continued

```
<213> ORGANISM: Ehrlichia sp.

<400> SEQUENCE: 7

aagatgaagc tgatacagta tatctactgg ctaaggagtt agcttatgat gttgttactg     60

gacagactga taagcttact gctgctcttg ctaagacctc cgggaaggac tttgttcagt    120

ttgctaaggc ggttggggtt tctcatccta atatcgatgg gaaggtttgt aagactacgc    180

tagggcacac gagtgcggat agctacggtg tgtatgggga gttaacaggc caggcgagtg    240

cgagtgagac atcgttatgt ggtggtaagg gtaaaaatag tagtggtggt ggagctgctc    300

ccgaagtttt aagggacttt gtaaagaaat ctctgaaaga tgggggccaa aactggccaa    360

catctagggc gaccgagagt tcacctaaga ctaaatctga aactaacgac aatgcaaaag    420

ctgtcgctaa agacctagta gaccttaatc ctgaagaaaa aaccatagta gcagggttac    480

tagctaaaac tattgaaggt ggggaagttg tagaaatcag agcagtttct               530


<210> SEQ ID NO 8
<211> LENGTH: 325
<212> TYPE: PRT
<213> ORGANISM: Ehrlichia sp.

<400> SEQUENCE: 8

Glu Leu Glu Ile Gly Tyr Glu Arg Phe Lys Thr Lys Gly Ile Arg Asp
 1               5                  10                  15

Ser Gly Ser Lys Glu Asp Glu Ala Asp Thr Val Tyr Leu Leu Ala Lys
            20                  25                  30

Glu Leu Ala Tyr Asp Val Val Thr Gly Gln Thr Asp Asn Leu Ala Ala
        35                  40                  45

Ala Leu Ala Lys Thr Ser Gly Lys Asp Ile Val Gln Phe Ala Lys Ala
    50                  55                  60

Val Glu Ile Ser His Ser Glu Ile Asp Gly Lys Val Cys Lys Thr Lys
65                  70                  75                  80

Ser Ala Gly Thr Gly Lys Asn Pro Cys Asp His Ser Gln Lys Pro Cys
                85                  90                  95

Ser Thr Asn Ala Tyr Tyr Ala Arg Arg Thr Gln Lys Ser Arg Ser Ser
            100                 105                 110

Gly Lys Thr Ser Leu Cys Gly Asp Ser Gly Tyr Ser Gly Gln Glu Leu
        115                 120                 125

Ile Thr Gly Gly His Tyr Ser Ser Pro Ser Val Phe Arg Asn Phe Val
    130                 135                 140

Lys Asp Thr Leu Gln Gly Asn Gly Ser Glu Asn Trp Pro Thr Ser Thr
145                 150                 155                 160

Gly Glu Gly Ser Glu Ser Asn Asp Asn Ala Ile Ala Val Ala Lys Asp
                165                 170                 175

Leu Val Asn Glu Leu Thr Pro Glu Glu Arg Thr Ile Val Ala Gly Leu
            180                 185                 190

Leu Ala Lys Ile Ile Glu Gly Ser Glu Val Ile Glu Ile Arg Ala Ile
        195                 200                 205

Ser Ser Thr Ser Val Thr Met Asn Ile Cys Ser Asp Ile Thr Ile Ser
    210                 215                 220

Asn Ile Leu Met Pro Tyr Val Cys Val Gly Pro Gly Met Ser Phe Val
225                 230                 235                 240

Ser Val Val Asp Gly His Thr Ala Ala Lys Phe Ala Tyr Arg Leu Lys
                245                 250                 255

Ala Gly Leu Ser Tyr Lys Phe Ser Lys Glu Val Thr Ala Phe Ala Gly
```

-continued

```
            260                 265                 270

Gly Phe Tyr His His Val Ile Gly Asp Gly Val Tyr Asp Asp Leu Pro
        275                 280                 285

Leu Arg His Leu Ser Asp Asp Ile Ser Pro Val Lys His Ala Lys Glu
    290                 295                 300

Thr Ala Ile Ala Arg Phe Val Met Arg Tyr Phe Gly Gly Glu Phe Gly
305                 310                 315                 320

Val Arg Leu Ala Phe
                325


<210> SEQ ID NO 9
<211> LENGTH: 323
<212> TYPE: PRT
<213> ORGANISM: Ehrlichia sp.

<400> SEQUENCE: 9

Phe Tyr Ile Gly Leu Asp Tyr Ser Pro Ala Phe Ser Lys Ile Arg Asp
 1               5                  10                  15

Phe Ser Ile Arg Glu Ser Asn Gly Glu Thr Lys Ala Val Tyr Pro Tyr
            20                  25                  30

Leu Lys Asp Gly Lys Ser Val Lys Leu Glu Ser His Lys Phe Asp Trp
        35                  40                  45

Asn Thr Pro Asp Pro Arg Ile Gly Phe Lys Asp Asn Met Leu Val Ala
    50                  55                  60

Met Glu Gly Ser Val Gly Tyr Gly Ile Gly Gly Ala Arg Val Glu Leu
65                  70                  75                  80

Glu Ile Gly Tyr Glu Arg Phe Lys Thr Lys Gly Ile Arg Asp Ser Gly
                85                  90                  95

Ser Lys Glu Asp Glu Ala Asp Thr Val Tyr Leu Leu Ala Lys Glu Leu
            100                 105                 110

Ala Tyr Asp Val Val Thr Gly Gln Thr Asp Asn Leu Ala Ala Ala Leu
        115                 120                 125

Ala Lys Thr Ser Gly Lys Asp Ile Val Gln Phe Ala Lys Ala Val Gly
    130                 135                 140

Val Ser His Pro Ser Ile Asp Gly Lys Val Cys Lys Thr Lys Ala Asp
145                 150                 155                 160

Ser Ser Lys Lys Phe Pro Leu Tyr Ser Asp Glu Thr His Thr Lys Gly
                165                 170                 175

Ala Asn Glu Gly Arg Thr Ser Leu Cys Gly Asp Asn Gly Ser Ser Thr
            180                 185                 190

Ile Thr Thr Ser Gly Thr Asn Val Ser Glu Thr Gly Gln Val Phe Arg
        195                 200                 205

Asp Phe Ile Arg Ala Thr Leu Lys Glu Asp Gly Ser Lys Asn Trp Pro
    210                 215                 220

Thr Ser Ser Gly Thr Gly Thr Pro Lys Pro Val Thr Asn Asp Asn Ala
225                 230                 235                 240

Lys Ala Val Ala Lys Asp Leu Val Gln Glu Leu Thr Pro Glu Glu Lys
                245                 250                 255

Thr Ile Val Ala Gly Leu Leu Ala Lys Thr Ile Glu Gly Gly Glu Val
            260                 265                 270

Val Glu Ile Arg Ala Val Ser Ser Thr Ser Val Met Val Asn Ala Cys
        275                 280                 285

Tyr Asp Leu Leu Ser Glu Gly Leu Gly Val Val Pro Tyr Ala Cys Val
    290                 295                 300
```

-continued

```
Gly Leu Gly Gly Asn Phe Val Gly Val Val Asp Gly Ile His Tyr Thr
305                 310                 315                 320

Asn His Leu


<210> SEQ ID NO 10
<211> LENGTH: 185
<212> TYPE: PRT
<213> ORGANISM: Ehrlichia sp.

<400> SEQUENCE: 10

Leu Leu Ala Lys Glu Leu Ala Tyr Asp Val Val Thr Gly Gln Thr Asp
 1               5                  10                  15

Asn Leu Ala Ala Ala Leu Ala Lys Thr Ser Gly Lys Asp Ile Val Gln
            20                  25                  30

Phe Ala Lys Thr Leu Asn Ile Ser His Ser Asn Ile Asp Gly Lys Val
        35                  40                  45

Cys Arg Arg Glu Lys His Gly Ser Gln Gly Leu Thr Gly Thr Lys Ala
    50                  55                  60

Gly Ser Cys Asp Ser Gln Pro Gln Thr Ala Gly Phe Asp Ser Met Lys
65                  70                  75                  80

Gln Gly Leu Met Ala Ala Leu Gly Glu Gln Gly Ala Glu Lys Trp Pro
                85                  90                  95

Lys Ile Asn Asn Gly Gly His Ala Thr Ile Tyr Ser Ser Ser Ala Gly
            100                 105                 110

Pro Gly Asn Ala Tyr Ala Arg Asp Ala Ser Thr Thr Val Ala Thr Asp
        115                 120                 125

Leu Thr Lys Leu Thr Thr Glu Glu Lys Thr Ile Val Ala Gly Leu Leu
    130                 135                 140

Ala Arg Thr Ile Glu Gly Gly Glu Val Val Glu Ile Arg Ala Val Ser
145                 150                 155                 160

Ser Thr Ser Val Met Val Asn Ala Cys Tyr Asp Leu Leu Ser Glu Gly
                165                 170                 175

Leu Gly Val Val Pro Tyr Ala Cys Val
            180                 185


<210> SEQ ID NO 11
<211> LENGTH: 185
<212> TYPE: PRT
<213> ORGANISM: Ehrlichia sp.

<400> SEQUENCE: 11

Ala Val Lys Ile Thr Asn Ser Thr Ile Asp Gly Lys Val Cys Asn Gly
 1               5                  10                  15

Ser Arg Glu Lys Gly Asn Ser Ala Gly Asn Asn Asn Ser Ala Val Ala
            20                  25                  30

Thr Tyr Ala Gln Thr His Thr Ala Asn Thr Ser Thr Ser Gln Cys Ser
        35                  40                  45

Gly Leu Gly Thr Thr Val Val Lys Gln Gly Tyr Gly Ser Leu Asn Lys
    50                  55                  60

Phe Val Ser Leu Thr Gly Val Gly Glu Gly Lys Asn Trp Pro Thr Gly
65                  70                  75                  80

Lys Ile His Asp Gly Ser Ser Gly Val Lys Asp Gly Glu Gln Asn Gly
                85                  90                  95

Asn Ala Lys Ala Val Ala Lys Asp Leu Val Asp Leu Asn Arg Asp Glu
            100                 105                 110

Lys Thr Ile Val Ala Gly Leu Leu Ala Lys Thr Ile Glu Gly Gly Glu
```

-continued

```
        115                 120                 125

Val Val Glu Ile Arg Ala Val Ser Ser Thr Ser Val Met Val Asn Ala
    130                 135                 140

Cys Tyr Asp Leu Leu Ser Glu Gly Leu Gly Val Val Pro Tyr Ala Cys
145                 150                 155                 160

Val Gly Leu Gly Gly Asn Phe Val Gly Val Val Asp Gly His Ile Thr
                165                 170                 175

Pro Lys Leu Ala Tyr Arg Leu Lys Ala
            180                 185


<210> SEQ ID NO 12
<211> LENGTH: 66
<212> TYPE: PRT
<213> ORGANISM: Ehrlichia sp.

<400> SEQUENCE: 12

Arg Phe Lys Thr Lys Gly Ile Arg Asp Ser Gly Ser Lys Glu Asp Glu
 1               5                  10                  15

Ala Asp Thr Val Tyr Leu Leu Ala Lys Glu Leu Ala Tyr Asp Val Val
            20                  25                  30

Thr Gly Gln Thr Asp Asn Leu Ala Ala Ala Leu Ala Lys Thr Ser Gly
        35                  40                  45

Lys Asp Phe Val Gln Phe Ala Lys Ala Val Glu Ile Ser Asn Ser Thr
    50                  55                  60

Ile Gly
65


<210> SEQ ID NO 13
<211> LENGTH: 155
<212> TYPE: PRT
<213> ORGANISM: Ehrlichia sp.

<400> SEQUENCE: 13

Tyr Ile Asp Ser Leu Arg Ser His Ser Leu Leu Leu Lys Arg Lys Thr
 1               5                  10                  15

Lys Gly Ile Arg Asp Ser Gly Ser Lys Glu Asp Glu Ala Asp Thr Val
            20                  25                  30

Tyr Leu Leu Ala Lys Glu Leu Ala Tyr Asp Val Val Thr Gly Gln Thr
        35                  40                  45

Asp Asn Leu Ala Ala Ala Leu Ala Lys Thr Ser Gly Lys Asp Phe Val
    50                  55                  60

Lys Phe Ala Asn Ala Val Val Gly Ile Ser His Pro Asp Val Asn Lys
65                  70                  75                  80

Lys Val Cys Ala Thr Arg Lys Asp Ser Gly Gly Thr Arg Tyr Ala Lys
                85                  90                  95

Tyr Ala Ala Thr Thr Asn Lys Ser Ser Asn Pro Glu Thr Ser Leu Cys
            100                 105                 110

Gly Asp Glu Gly Gly Ser Ser Gly Thr Asn Asn Thr Gln Glu Phe Leu
        115                 120                 125

Lys Glu Phe Val Ala Gln Thr Leu Val Glu Asn Glu Ser Lys Asn Trp
    130                 135                 140

Pro Thr Ser Ser Gly Thr Gly Leu Lys Thr Asn
145                 150                 155


<210> SEQ ID NO 14
<211> LENGTH: 176
<212> TYPE: PRT
```

-continued

<213> ORGANISM: Ehrlichia sp.

<400> SEQUENCE: 14

```
Asp Glu Ala Asp Thr Val Tyr Leu Leu Ala Lys Glu Leu Ala Tyr Asp
 1               5                  10                  15

Val Val Thr Gly Gln Thr Asp Lys Leu Thr Ala Ala Leu Ala Lys Thr
            20                  25                  30

Ser Gly Lys Asp Phe Val Gln Phe Ala Lys Ala Val Gly Val Ser His
        35                  40                  45

Pro Asn Ile Asp Gly Lys Val Cys Lys Thr Thr Leu Gly His Thr Ser
    50                  55                  60

Ala Asp Ser Tyr Gly Val Tyr Gly Glu Leu Thr Gly Gln Ala Ser Ala
65                  70                  75                  80

Ser Glu Thr Ser Leu Cys Gly Gly Lys Gly Lys Asn Ser Ser Gly Gly
                85                  90                  95

Gly Ala Ala Pro Glu Val Leu Arg Asp Phe Val Lys Lys Ser Leu Lys
            100                 105                 110

Asp Gly Gly Gln Asn Trp Pro Thr Ser Arg Ala Thr Glu Ser Ser Pro
        115                 120                 125

Lys Thr Lys Ser Glu Thr Asn Asp Asn Ala Lys Ala Val Ala Lys Asp
    130                 135                 140

Leu Val Asp Leu Asn Pro Glu Glu Lys Thr Ile Val Ala Gly Leu Leu
145                 150                 155                 160

Ala Lys Thr Ile Glu Gly Gly Glu Val Val Glu Ile Arg Ala Val Ser
                165                 170                 175
```

<210> SEQ ID NO 15
<211> LENGTH: 1185
<212> TYPE: DNA
<213> ORGANISM: Ehrlichia sp.

<400> SEQUENCE: 15

```
gaaacagcat tgctagattt cgttgaacaa tttgctaatt tgcaactaaa gcactcatga     60

taaagcttga tagtatttta gaggatagta ggcaatatgg tttaggggat ttcttcgcat    120

acttgttatc atcgtcctta tttgtgctta gttggtcgga tatttgtgca agttgttgta    180

aaatatgcat attgtatgta taggtgtgca agatatcatc tctttaggtg tatcgtgtag    240

cacttaaaca aatgctggtg aacgtagagg gattaaagga ggatttgcgt atatgtatgg    300

tatagatata gagctaagtg attacagaat tggtagtgaa accatttcca gtggagatga    360

tggctactac gaaggatgtg cttgtgacaa agatgccagc actaatgcgt actcgtatga    420

caagtgtagg gtagtacggg gaacgtggag accgagcgaa ctggttttat atgttggtga    480

tgagcatgtg gcatgtagag atgttgcttc gggtatgcat catggtaatt tgccagggga    540

aggtgtattt tatagaggca gaagcgggca gagctgctac tgctgaaggt ggtgtttata    600

ctaccgttgt ggaggcatta tcgctggtgc aagaggaaga gggtacaggt atgtacttga    660

taaacgcacc agaaaaagcg gtcgtaaggt ttttcaagat agaaaagagt gcagcagagg    720

aacctcaaac agtagatcct agtgtagttg agtcagcaac agggtcgggt gtagatacgc    780

aagaagaaca agaaatagat caagaagcac cagcaattga agaagttgag acagaagagc    840

aagaagttat tctggaagaa ggtactttga tagatcttga gcaacctgta gcgcaagtac    900

ctgtagtagc tgaagcagaa ttacctggtg ttgaagctgc agaagcgatt gtaccatcac    960

tagaagaaaa taagcttcaa gaagtggtag ttgctccaga agcgcaacaa ctagaatcag   1020
```

```
ctcctgaagt ttctgcgcca gcacaacctg agtctacagt tcttggtgtt gctgaaggtg   1080

atctaaagtc tgaagtatct gtagaagcta atgctgatgt acgcaaaaag aagtaatctc   1140

tggtccacra gagcaagaaa ttgcagaagc actagaggga actga                    1185
```

<210> SEQ ID NO 16
<211> LENGTH: 1131
<212> TYPE: DNA
<213> ORGANISM: Ehrlichia sp.

<400> SEQUENCE: 16

```
ataaaggggc tccagcaacg cagagagatg cttatggtaa gacggcttta catatagcag     60

ctgctaatgg tgacggtaag ctatataagt taattgcgaa aaaatgccca gatagctgtc    120

aagcactcct ttctcatatg ggagatacag cgttacatga ggctttatat tctgataagg    180

ttacagaaaa atgcttttta aagatgctta aagagtctcg aaagcatttg tcaaactcat    240

ctttcggaga cttgcttaat actcctcaag aagcaaatgg tgacacgtta ctgcatctgg    300

ctgcatcgcg tggtttcggt aaagcatgta aaatactact aaagtctggg gcgtcagtat    360

cagtcgtgaa tgtagaggga aaaacaccgg tagatgttgc ggatccatca ttgaaaactc    420

gtccgtggtt ttttggaaag tccgttgtca caatgatggc tgaacgtgtt caagttcctg    480

aaggggggatt cccaccatat ctgccgcctg aaagtccaac tccttcttta ggatctattt    540

caagttttga gagtgtctct gcgctatcat ccttgggtag tggcctagat actgcaggag    600

ctgaggagtc tatctacgaa gaaattaagg atacagcaaa aggtacaacg gaagttgaaa    660

gcacatatac aactgtagga gctgaggagt ctatctacga agaaattaag gatacagcaa    720

aaggtacaac ggaagttgaa agcacatata caactgtagg agctgaaggt ccgagaacac    780

cagaaggtga agatctgtat gctactgtgg gagctgcaat tacttccgag gcgcaagcat    840

cagatgcggc gtcatctaag ggagaaaggc cggaatccat ttatgctgat ccatttgata    900

tagtgaaacc taggcaggaa aggcctgaat ctatctatgc tgacccattt gctgcggaac    960

gaacatcttc tggagtaacg acatttggcc ctaaggaaga gccgatttat gcaacagtga   1020

aaaagggtcc taagaagagt gatacttctc aaaaagaagg aacagcttct gaaaaagtcg   1080

gctcaacaat aactgtgatt aagaagaaag tgaaacctca ggttccagct a            1131
```

<210> SEQ ID NO 17
<211> LENGTH: 800
<212> TYPE: DNA
<213> ORGANISM: Ehrlichia sp.

<400> SEQUENCE: 17

```
aatgcgctcc acataactag cataacgttt tcagcaacgg cagatcttca tatataagca     60

ctgaacacct acgttccaag atcatgctct tcgcgcctgt ttacttggtg gctcagagtc    120

atcatcacta ggagttcgtg gtctgtgaga gctaacttgt gcttcttcca gcgtataact    180

agcacctccc aatcctgatg ctgaaggttg atcccacgaa taaggcataa tcccttgatc    240

ctgaggtggc acatagggag cttgtgatct tcccattcca gtactagtac ctcctagccc    300

agatgttgag aattggctag atggataagg aacattctct aggacacgta gtataatatg    360

aggggggggg ggaacgagtt gagctccctg tccggcagta cctcccaatc ctgatgttga    420

gggttgatcc catgatgttg agggttgatc ccacgatgtt gaaggttgtg catacgaata    480

gggcatcatc cctggatcat gtggtggaat atgcgaagct tgttgacttc ccattccagc    540

ggcacttcct aaccctgatg ttgagggttg atcccacgat gttgaatgtt gtgcatacga    600
```

-continued

```
atagggcatc atccctggat catgtggtgg aatatgcgaa gcttgttgac ttcccattcc    660

agcggcactt cctaaccctg atgttgaggg ttgatcccac gatgttgaag gttgtgcata    720

cgaatagggc atcatccctg gatcatgtgg tggaatatgc gaagcttgtt gacttcccgt    780

tccagcggca cttcctaacc                                                800


<210> SEQ ID NO 18
<211> LENGTH: 1011
<212> TYPE: DNA
<213> ORGANISM: Ehrlichia sp.

<400> SEQUENCE: 18

aatgtataca gtctcagatt cagaatctat aacttctttc gttactccac caatgttaat     60

ggcgaatatc tcatcgacta agcgttcagg atacttgcta tcattgtcgg tagagccatc    120

tgactttttt accgtgacat tctttttaaa agaaactcca tttacaacgg acaattcagt    180

gccattttgt agcttcgagc gcaactccac agcaaattca cgtattttct tcatacgtaa    240

tgcactcttc cattcttcag taagaataga cctgctttct tcaagtgtcc ttggtcttgg    300

aggcactact tcagtaacaa gaacgccgaa ataagcgtca ccattgctaa ccagatgaga    360

cggttttcct acggcagatg aaaacgccaa agtagtaaag gcgtttatac caagctgcaa    420

cggaaagtct ttcactaagt tgccagattt atcgagccca tgcatatcaa aattcgtcaa    480

aacaccactg atccgcgcac caaacatatc ctttagttca ttcagcaatg ccccgcggct    540

gatcatatcg tttgcttttt tcacattgct aactagcaac tcacctgcct tttgccttct    600

aatatttgaa gatatcttct ctttcagctt ttctaggtct tccttagtga tctcatgctt    660

ccttattacc ttcatgatat gccagccgac aacgctacgg aacatttcac tgacttctcc    720

ttcatttagt gcaaacacca catttcgcac acctaccgga agaacatcct tagagatatt    780

attgagtgca atatcctcta tggtgtagcc agcatcacta accaattcct caaaagactt    840

accctcttgg taagctttgt aagctagctc agcttcattt ttgtctgtaa atactaaatt    900

tagaacatct ctttgatcat gtagttcact gtttttaatc tcaacgtcta ccttcttgat    960

ccgaaacaat gacatcagca agcaagtcgt cttctgccat gattatatga t            1011


<210> SEQ ID NO 19
<211> LENGTH: 513
<212> TYPE: DNA
<213> ORGANISM: Ehrlichia sp.

<400> SEQUENCE: 19

gcaaatattt ttcttggtgc cgccctaaaa gcctgaaaaa tttaaagaaa tgttactgct     60

ctagtcattc ataaaatgca aatagcctac agaaggagta tttactgcta taggcttgaa    120

agtgcaatcg ttatttacta ttttttatac atatcgcagt acagagattt tacgcgctac    180

gcctgtgcat catagccgta ttgcatcaat aaattgtcgt tgctacgcgg gaaagctgct    240

tagcgcttga ccatttttca tacacattgt accatcatag cgagtgtggt gctcatgaga    300

gtgcgtagtg ttgccgccgg tttctcatgt tataatcttg ctgccgtttt gtgcagaagg    360

aggagtagtc tcgttttttt ccaaaagaca atgtgctgga gtgtcccggt gagcctcaag    420

gttcttgtgg gatttgtgtg ggctgttgta taaataccac gttcgaagct gtcctagtgt    480

attcagcata tgttgaggaa gttgttgcta tga                                 513


<210> SEQ ID NO 20
```

-continued

<211> LENGTH: 464
<212> TYPE: DNA
<213> ORGANISM: Ehrlichia sp.

<400> SEQUENCE: 20
agtcattgag tcgagggtag tcttgtggat ccctgataaa tgttctaaaa tttaaaacaa 60
cactagagtt ttgatcacat gttggttgtc agaaaaaaaa tgtcaaaaaa tttaccaggg 120
ctttttgaaa tgcctagatt ttccatttct caatgaaact tgtttgatca tgactattcc 180
agctaatgga gcagtgtgat gtagaggaag gagccactga gggtatgtgg ggtgttagac 240
tggatcatca ttcttcaagg cgtgttcctt ggaatgcctg ggaggagagc aattttctat 300
taaaatttaa ttcgcctcct tccaaatatg gttccctgga cgatttagca aatagcattc 360 ctttttgga gattcaaaaa gcacattagc attgaggatt gctacagtaa agaaatctgc 420
ctaactttgt tttatccagt attgcctaaa attattggac cact 464

<210> SEQ ID NO 21
<211> LENGTH: 527
<212> TYPE: DNA
<213> ORGANISM: Ehrlichia sp.

<400> SEQUENCE: 21
cctatggcag ctctaaactc ggcacgactg gtttctacaa gagattggtc gacattaaac 60
catgcgaaat cattgcgatc aattcttcct tctttttcct gtatagcact acagacttcc 120
tctgcactag aagccactcg tgtcccgatg cgtacgtcac ggatgcaaag ccccaggtct 180
tttacgctgc cgggtgtgtc tatatcttcc acaacataat caacgcaagc gtgaatatgg 240
ataccagaaa cagaggtaac cctgtatact aaatgctctt ccaaaacatg ttgattaaca 300
ggtaagcgcc tagcactatc accattatca gcaacaacgc cttcatgcgc aacgtaatga 360
gcagcgagct caactggcag agatgaccca ctactgttac tcaagatact agataagagt 420
acccggagat tttctgtgtt tacaccagtt ttctccacaa tatttgcagc atgcttcggc 480
tgtgacctta agatttcacg tatttcatcg gagtgttgta tgaaaat 527

<210> SEQ ID NO 22
<211> LENGTH: 464
<212> TYPE: DNA
<213> ORGANISM: Ehrlichia sp.

<400> SEQUENCE: 22
ttcacctggc caaatcttat tggatcttca ggacaaagac caagaatctg cttctccaag 60
aagcattctc tgacccccac ctacctatct gactcttagc ttagattcct aatggtgtga 120
gtgtgtcaga gcctttactt agtctaagcg taactgtaaa aacatctttt caaaagtctc 180
tgcatgactg tctaggtctc acctatcaca ctgtaagcat ctggaaaaca aagccactga 240
gtcttccttt taccaaaaag gcctagcctt gtttttgaca aatggcaaga acacattaga 300
tgtttgttga gagaacaaaa ggagagaact cattatgaaa ctctggacaa catttatata 360
cctctctaca ttttttgtgt tggaggttag ttttcttttc taataatttg atttctttgg 420
atacatcgag gcaatacact taagaagcaa gaagattggg ggcc 464

<210> SEQ ID NO 23
<211> LENGTH: 233
<212> TYPE: PRT
<213> ORGANISM: Ehrlichia sp.

<400> SEQUENCE: 23

-continued

```
Tyr Gly Glu Arg Gly Asp Arg Ala Asn Trp Phe Tyr Met Leu Val Met
 1               5                  10                  15

Ser Met Trp His Val Glu Met Leu Leu Arg Val Cys Ile Met Val Ile
            20                  25                  30

Cys Gln Gly Lys Val Tyr Phe Ile Glu Ala Glu Ala Gly Arg Ala Ala
        35                  40                  45

Thr Ala Glu Gly Gly Val Tyr Thr Thr Val Val Glu Ala Leu Ser Leu
    50                  55                  60

Val Gln Glu Glu Glu Gly Thr Gly Met Tyr Leu Ile Asn Ala Pro Glu
65                  70                  75                  80

Lys Ala Val Val Arg Phe Phe Lys Ile Glu Lys Ser Ala Ala Glu Glu
                85                  90                  95

Pro Gln Thr Val Asp Pro Ser Val Val Glu Ser Ala Thr Gly Ser Gly
            100                 105                 110

Val Asp Thr Gln Glu Glu Gln Glu Ile Asp Gln Glu Ala Pro Ala Ile
        115                 120                 125

Glu Glu Val Glu Thr Glu Glu Gln Glu Val Ile Leu Glu Glu Gly Thr
    130                 135                 140

Leu Ile Asp Leu Glu Gln Pro Val Ala Gln Val Pro Val Val Ala Glu
145                 150                 155                 160

Ala Glu Leu Pro Gly Val Glu Ala Ala Glu Ala Ile Val Pro Ser Leu
                165                 170                 175

Glu Glu Asn Lys Leu Gln Glu Val Val Val Ala Pro Glu Ala Gln Gln
            180                 185                 190

Leu Glu Ser Ala Pro Glu Val Ser Ala Pro Ala Gln Pro Glu Ser Thr
        195                 200                 205

Val Leu Gly Val Ala Glu Gly Asp Leu Lys Ser Glu Val Ser Val Glu
    210                 215                 220

Ala Asn Ala Asp Val Arg Lys Lys Lys
225                 230


<210> SEQ ID NO 24
<211> LENGTH: 376
<212> TYPE: PRT
<213> ORGANISM: Ehrlichia sp.

<400> SEQUENCE: 24

Lys Gly Ala Pro Ala Thr Gln Arg Asp Ala Tyr Gly Lys Thr Ala Leu
 1               5                  10                  15

His Ile Ala Ala Ala Asn Gly Asp Gly Lys Leu Tyr Lys Leu Ile Ala
            20                  25                  30

Lys Lys Cys Pro Asp Ser Cys Gln Ala Leu Leu Ser His Met Gly Asp
        35                  40                  45

Thr Ala Leu His Glu Ala Leu Tyr Ser Asp Lys Val Thr Glu Lys Cys
    50                  55                  60

Phe Leu Lys Met Leu Lys Glu Ser Arg Lys His Leu Ser Asn Ser Ser
65                  70                  75                  80

Phe Gly Asp Leu Leu Asn Thr Pro Gln Glu Ala Asn Gly Asp Thr Leu
                85                  90                  95

Leu His Leu Ala Ala Ser Arg Gly Phe Gly Lys Ala Cys Lys Ile Leu
            100                 105                 110

Leu Lys Ser Gly Ala Ser Val Ser Val Val Asn Val Glu Gly Lys Thr
        115                 120                 125

Pro Val Asp Val Ala Asp Pro Ser Leu Lys Thr Arg Pro Trp Phe Phe
```

-continued

```
    130                 135                 140

Gly Lys Ser Val Val Thr Met Met Ala Glu Arg Val Gln Val Pro Glu
145                 150                 155                 160

Gly Gly Phe Pro Pro Tyr Leu Pro Pro Glu Ser Pro Thr Pro Ser Leu
                165                 170                 175

Gly Ser Ile Ser Ser Phe Glu Ser Val Ser Ala Leu Ser Ser Leu Gly
            180                 185                 190

Ser Gly Leu Asp Thr Ala Gly Ala Glu Glu Ser Ile Tyr Glu Glu Ile
        195                 200                 205

Lys Asp Thr Ala Lys Gly Thr Thr Glu Val Glu Ser Thr Tyr Thr Thr
    210                 215                 220

Val Gly Ala Glu Glu Ser Ile Tyr Glu Glu Ile Lys Asp Thr Ala Lys
225                 230                 235                 240

Gly Thr Thr Glu Val Glu Ser Thr Tyr Thr Thr Val Gly Ala Glu Gly
                245                 250                 255

Pro Arg Thr Pro Glu Gly Glu Asp Leu Tyr Ala Thr Val Gly Ala Ala
            260                 265                 270

Ile Thr Ser Glu Ala Gln Ala Ser Asp Ala Ala Ser Ser Lys Gly Glu
        275                 280                 285

Arg Pro Glu Ser Ile Tyr Ala Asp Pro Phe Asp Ile Val Lys Pro Arg
    290                 295                 300

Gln Glu Arg Pro Glu Ser Ile Tyr Ala Asp Pro Phe Ala Ala Glu Arg
305                 310                 315                 320

Thr Ser Ser Gly Val Thr Thr Phe Gly Pro Lys Glu Glu Pro Ile Tyr
                325                 330                 335

Ala Thr Val Lys Lys Gly Pro Lys Lys Ser Asp Thr Ser Gln Lys Glu
            340                 345                 350

Gly Thr Ala Ser Glu Lys Val Gly Ser Thr Ile Thr Val Ile Lys Lys
        355                 360                 365

Lys Val Lys Pro Gln Val Pro Ala
    370                 375


<210> SEQ ID NO 25
<211> LENGTH: 148
<212> TYPE: PRT
<213> ORGANISM: Ehrlichia sp.

<400> SEQUENCE: 25

Tyr Glu Gly Gly Gly Glu Arg Val Glu Leu Pro Val Arg Gln Tyr Leu
 1               5                  10                  15

Pro Ile Leu Met Leu Arg Val Asp Pro Met Met Leu Arg Val Asp Pro
            20                  25                  30

Thr Met Leu Lys Val Val His Thr Asn Arg Ala Ser Ser Leu Asp His
        35                  40                  45

Val Val Glu Tyr Ala Lys Leu Val Asp Phe Pro Phe Gln Arg His Phe
    50                  55                  60

Leu Thr Leu Met Leu Arg Val Asp Pro Thr Met Leu Lys Val Val His
65                  70                  75                  80

Thr Asn Arg Ala Ser Ser Leu Asp His Val Val Glu Tyr Ala Lys Leu
                85                  90                  95

Val Asp Phe Pro Phe Gln Arg His Phe Leu Thr Leu Met Leu Arg Val
            100                 105                 110

Asp Pro Thr Met Leu Lys Val Val His Thr Asn Arg Ala Ser Ser Leu
        115                 120                 125
```

-continued

```
Asp His Val Val Glu Tyr Ala Lys Leu Val Asp Phe Pro Phe Gln Arg
    130                 135                 140

His Phe Leu Thr
145


<210> SEQ ID NO 26
<211> LENGTH: 89
<212> TYPE: PRT
<213> ORGANISM: Ehrlichia sp.

<400> SEQUENCE: 26

Tyr Gly Ser Ser Lys Leu Gly Thr Thr Gly Phe Tyr Lys Arg Leu Val
 1               5                  10                  15

Asp Ile Lys Pro Cys Glu Ile Ile Ala Ile Asn Ser Ser Phe Phe Phe
            20                  25                  30

Leu Tyr Ser Thr Thr Asp Phe Leu Cys Thr Arg Ser His Ser Cys Pro
        35                  40                  45

Asp Ala Tyr Val Thr Asp Ala Lys Pro Gln Val Phe Tyr Ala Ala Gly
    50                  55                  60

Cys Val Tyr Ile Phe His Asn Ile Ile Asn Ala Ser Val Asn Met Asp
65                  70                  75                  80

Thr Arg Asn Arg Gly Asn Pro Val Tyr
                85


<210> SEQ ID NO 27
<211> LENGTH: 238
<212> TYPE: PRT
<213> ORGANISM: Ehrlichia sp.

<400> SEQUENCE: 27

Leu Gly Ser Ala Ala Gly Thr Gly Ser Gln Gln Ala Ser His Ile Pro
 1               5                  10                  15

Pro His Asp Pro Gly Met Met Pro Tyr Ser Tyr Ala Gln Pro Ser Thr
            20                  25                  30

Ser Trp Asp Gln Pro Ser Thr Ser Gly Leu Gly Ser Ala Ala Gly Met
        35                  40                  45

Gly Ser Gln Gln Ala Ser His Ile Pro Pro His Asp Pro Gly Met Met
    50                  55                  60

Pro Tyr Ser Tyr Ala Gln Pro Ser Thr Ser Trp Asp Gln Pro Ser Thr
65                  70                  75                  80

Ser Gly Leu Gly Ser Ala Ala Gly Met Gly Ser Gln Gln Ala Ser His
                85                  90                  95

Ile Pro Pro His Asp Pro Gly Met Met Pro Tyr Ser Tyr Ala Gln Pro
            100                 105                 110

Ser Thr Ser Trp Asp Gln Pro Ser Thr Ser Trp Asp Gln Pro Ser Thr
        115                 120                 125

Ser Gly Leu Gly Gly Thr Ala Gly Gln Gly Ala Gln Leu Val Pro Pro
    130                 135                 140

Pro Pro His Ile Ile Leu Arg Val Leu Glu Asn Val Pro Tyr Pro Ser
145                 150                 155                 160

Ser Gln Phe Ser Thr Ser Gly Leu Gly Gly Thr Ser Thr Gly Met Gly
                165                 170                 175

Arg Ser Gln Ala Pro Tyr Val Pro Pro Gln Asp Gln Gly Ile Met Pro
            180                 185                 190

Tyr Ser Trp Asp Gln Pro Ser Ala Ser Gly Leu Gly Gly Ala Ser Tyr
        195                 200                 205
```

```
Thr Leu Glu Glu Ala Gln Val Ser Ser His Arg Pro Arg Thr Pro Ser
    210                 215                 220

Asp Asp Asp Ser Glu Pro Pro Ser Lys Gln Ala Arg Arg Ala
225                 230                 235


<210> SEQ ID NO 28
<211> LENGTH: 334
<212> TYPE: PRT
<213> ORGANISM: Ehrlichia sp.

<400> SEQUENCE: 28

Ser Trp Gln Lys Thr Thr Cys Leu Leu Met Ser Leu Phe Arg Ile Lys
 1               5                  10                  15

Lys Val Asp Val Glu Ile Lys Asn Ser Glu Leu His Asp Gln Arg Asp
            20                  25                  30

Val Leu Asn Leu Val Phe Thr Asp Lys Asn Glu Ala Glu Leu Ala Tyr
        35                  40                  45

Lys Ala Tyr Gln Glu Gly Lys Ser Phe Glu Glu Leu Val Ser Asp Ala
    50                  55                  60

Gly Tyr Thr Ile Glu Asp Ile Ala Leu Asn Asn Ile Ser Lys Asp Val
65                  70                  75                  80

Leu Pro Val Gly Val Arg Asn Val Val Phe Ala Leu Asn Glu Gly Glu
                85                  90                  95

Val Ser Glu Met Phe Arg Ser Val Val Gly Trp His Ile Met Lys Val
            100                 105                 110

Ile Arg Lys His Glu Ile Thr Lys Glu Asp Leu Glu Lys Leu Lys Glu
        115                 120                 125

Lys Ile Ser Ser Asn Ile Arg Arg Gln Lys Ala Gly Glu Leu Leu Val
    130                 135                 140

Ser Asn Val Lys Lys Ala Asn Asp Met Ile Ser Arg Gly Ala Leu Leu
145                 150                 155                 160

Asn Glu Leu Lys Asp Met Phe Gly Ala Arg Ile Ser Gly Val Leu Thr
                165                 170                 175

Asn Phe Asp Met His Gly Leu Asp Lys Ser Gly Asn Leu Val Lys Asp
            180                 185                 190

Phe Pro Leu Gln Leu Gly Ile Asn Ala Phe Thr Thr Leu Ala Phe Ser
        195                 200                 205

Ser Ala Val Gly Lys Pro Ser His Leu Val Ser Asn Gly Asp Ala Tyr
    210                 215                 220

Phe Gly Val Leu Val Thr Glu Val Val Pro Pro Arg Pro Arg Thr Leu
225                 230                 235                 240

Glu Glu Ser Arg Ser Ile Leu Thr Glu Glu Trp Lys Ser Ala Leu Arg
                245                 250                 255

Met Lys Lys Ile Arg Glu Phe Ala Val Glu Leu Arg Ser Lys Leu Gln
            260                 265                 270

Asn Gly Thr Glu Leu Ser Val Val Asn Gly Val Ser Phe Lys Lys Asn
        275                 280                 285

Val Thr Val Lys Lys Ser Asp Gly Ser Thr Asp Asn Asp Ser Lys Tyr
    290                 295                 300

Pro Glu Arg Leu Val Asp Glu Ile Phe Ala Ile Asn Ile Gly Gly Val
305                 310                 315                 320

Thr Lys Glu Val Ile Asp Ser Glu Ser Glu Thr Val Tyr Ile
                325                 330


<210> SEQ ID NO 29
```

```
<211> LENGTH: 175
<212> TYPE: PRT
<213> ORGANISM: Ehrlichia sp.

<400> SEQUENCE: 29

Ile Phe Ile Gln His Ser Asp Glu Ile Arg Glu Ile Leu Arg Ser Gln
 1               5                  10                  15

Pro Lys His Ala Ala Asn Ile Val Glu Lys Thr Gly Val Asn Thr Glu
            20                  25                  30

Asn Leu Arg Val Leu Leu Ser Ser Ile Leu Ser Asn Ser Ser Gly Ser
        35                  40                  45

Ser Leu Pro Val Glu Leu Ala Ala His Tyr Val Ala His Glu Gly Val
    50                  55                  60

Val Ala Asp Asn Gly Asp Ser Ala Arg Arg Leu Pro Val Asn Gln His
65                  70                  75                  80

Val Leu Glu Glu His Leu Val Tyr Arg Val Thr Ser Val Ser Gly Ile
                85                  90                  95

His Ile His Ala Cys Val Asp Tyr Val Val Glu Asp Ile Asp Thr Pro
            100                 105                 110

Gly Ser Val Lys Asp Leu Gly Leu Cys Ile Arg Asp Val Arg Ile Gly
        115                 120                 125

Thr Arg Val Ala Ser Ser Ala Glu Glu Val Cys Ser Ala Ile Gln Glu
    130                 135                 140

Lys Glu Gly Arg Ile Asp Arg Asn Asp Phe Ala Trp Phe Asn Val Asp
145                 150                 155                 160

Gln Ser Leu Val Glu Thr Ser Arg Ala Glu Phe Arg Ala Ala Ile
                165                 170                 175


<210> SEQ ID NO 30
<211> LENGTH: 41
<212> TYPE: PRT
<213> ORGANISM: Ehrlichia sp.
<220> FEATURE:
<221> NAME/KEY: VARIANT
<222> LOCATION: (7)...(7)
<223> OTHER INFORMATION: Xaa = Methionine or Threonine

<400> SEQUENCE: 30

Leu Gly Ser Ala Ala Gly Xaa Gly Ser Gln Gln Ala Ser His Ile Pro
 1               5                  10                  15

Pro His Asp Pro Gly Met Met Pro Tyr Ser Tyr Ala Gln Pro Ser Thr
            20                  25                  30

Ser Trp Asp Gln Pro Ser Thr Ser Gly
        35                  40


<210> SEQ ID NO 31
<211> LENGTH: 860
<212> TYPE: DNA
<213> ORGANISM: Ehrlichia sp.

<400> SEQUENCE: 31

aaaagcttaa ggaagatgtg gcttctatgt cggatgaggc tttgctgaag tttgccaata     60

ggctcagaag aggtgttcct atggctgctc cggtgtttga gggtccgaag gatgcgcaga    120

tttcccggct tttggaatta gcggatgttg atccgtctgg gcaggtggat ctttatgatg    180

ggcgttcagg gcagaagttt gatcgcaagg taactgttgg atacatttac atgttgaagc    240

tccatcactt ggtggatgac aagatacatg ctaggtctgt tggtccgtat ggtctggtta    300

ctcagcaacc tcttggagga aagtcgcact ttggtgggca gagatttggg gaaatggaat    360
```

-continued

```
gctgggcatt gcaggcctat ggtgctgctt atactttgca ggaaatgcta actgtcaaat    420

ctgacgatat cgtaggtagg gtaacaatct atgaatccat aattaagggg gatagcaact    480

tcgagtgtgg tattcctgag tcgtttaatg tcatggtcaa ggagttacgc tcgctgtgcc    540

ttgatgttgt tctaaagcag gataaagagt ttactagtag caaggtggag tagggattta    600

caattatgaa gacgttggat ttgtatggct ataccagtat agcacagtcg ttcgataaca    660

tttgcatatc catatctagt ccacaaagta taagggctat gtcctatgga gaaatcaagg    720

atatctctac tactatctat cgtaccttta aggtggagaa ggggggcta ttctgtccta    780

agatctttgg tccggttaat gatgacgagt gtctttgtgg taagtatagg aaaaagcgct    840

acaggggcat tgtctgtgaa                                                860
```

<210> SEQ ID NO 32
<211> LENGTH: 196
<212> TYPE: PRT
<213> ORGANISM: Ehrlichia sp.

<400> SEQUENCE: 32

```
Lys Leu Lys Glu Asp Val Ala Ser Met Ser Asp Glu Ala Leu Leu Lys
 1               5                  10                  15

Phe Ala Asn Arg Leu Arg Arg Gly Val Pro Met Ala Ala Pro Val Phe
            20                  25                  30

Glu Gly Pro Lys Asp Ala Gln Ile Ser Arg Leu Leu Glu Leu Ala Asp
        35                  40                  45

Val Asp Pro Ser Gly Gln Val Asp Leu Tyr Asp Gly Arg Ser Gly Gln
    50                  55                  60

Lys Phe Asp Arg Lys Val Thr Val Gly Tyr Ile Tyr Met Leu Lys Leu
65                  70                  75                  80

His His Leu Val Asp Asp Lys Ile His Ala Arg Ser Val Gly Pro Tyr
                85                  90                  95

Gly Leu Val Thr Gln Gln Pro Leu Gly Gly Lys Ser His Phe Gly Gly
            100                 105                 110

Gln Arg Phe Gly Glu Met Glu Cys Trp Ala Leu Gln Ala Tyr Gly Ala
        115                 120                 125

Ala Tyr Thr Leu Gln Glu Met Leu Thr Val Lys Ser Asp Asp Ile Val
    130                 135                 140

Gly Arg Val Thr Ile Tyr Glu Ser Ile Ile Lys Gly Asp Ser Asn Phe
145                 150                 155                 160

Glu Cys Gly Ile Pro Glu Ser Phe Asn Val Met Val Lys Glu Leu Arg
                165                 170                 175

Ser Leu Cys Leu Asp Val Val Leu Lys Gln Asp Lys Glu Phe Thr Ser
            180                 185                 190

Ser Lys Val Glu
        195
```

<210> SEQ ID NO 33
<211> LENGTH: 89
<212> TYPE: PRT
<213> ORGANISM: Ehrlichia sp.

<400> SEQUENCE: 33

```
Gly Phe Thr Ile Met Lys Thr Leu Asp Leu Tyr Gly Tyr Thr Ser Ile
 1               5                  10                  15

Ala Gln Ser Phe Asp Asn Ile Cys Ile Ser Ile Ser Ser Pro Gln Ser
            20                  25                  30
```

-continued

```
Ile Arg Ala Met Ser Tyr Gly Glu Ile Lys Asp Ile Ser Thr Thr Ile
        35                  40                  45

Tyr Arg Thr Phe Lys Val Glu Lys Gly Gly Leu Phe Cys Pro Lys Ile
    50                  55                  60

Phe Gly Pro Val Asn Asp Asp Glu Cys Leu Cys Gly Lys Tyr Arg Lys
65                  70                  75                  80

Lys Arg Tyr Arg Gly Ile Val Cys Glu
                85


<210> SEQ ID NO 34
<211> LENGTH: 484
<212> TYPE: DNA
<213> ORGANISM: Ehrlichia sp.

<400> SEQUENCE: 34

atcataagct ttacatgtcc tatccaggcg attatcccta tccatagcat agtaacgccc     60

tgcaacagta gcaatttcgg catttaagtg ctcaatttta gcgttcagca taccgatata    120

cttctcagca gaacgcggtg gaacatccct accatctaga attacatgta taaaaacctt    180

gatgccaaat ccggtgataa cctcaataat ggtttccatg tgcgcctgaa gagaatgcac    240

tccaccatca gaaagcagac caatcatgtg gcataccccca cccttcgcct gtatatcgcg    300

cacaaagtcc aacaatttag gattcttgtg aacctcatta atctcaagat taattctcaa    360

cagatcctga agcactatcc tgccgcatcc tatacttatg tgccctactt ctgaattccc    420

gaactgacct gaaggcaatc cgacatccgt tccactagca gacaaactac tcataggaca    480

gcat                                                                 484


<210> SEQ ID NO 35
<211> LENGTH: 161
<212> TYPE: PRT
<213> ORGANISM: Ehrlichia sp.

<400> SEQUENCE: 35

Cys Cys Pro Met Ser Ser Leu Ser Ala Ser Gly Thr Asp Val Gly Leu
 1               5                  10                  15

Pro Ser Gly Gln Phe Gly Asn Ser Glu Val Gly His Ile Ser Ile Gly
            20                  25                  30

Cys Gly Arg Ile Val Leu Gln Asp Leu Leu Arg Ile Asn Leu Glu Ile
        35                  40                  45

Asn Glu Val His Lys Asn Pro Lys Leu Leu Asp Phe Val Arg Asp Ile
    50                  55                  60

Gln Ala Lys Gly Gly Val Cys His Met Ile Gly Leu Leu Ser Asp Gly
65                  70                  75                  80

Gly Val His Ser Leu Gln Ala His Met Glu Thr Ile Ile Glu Val Ile
                85                  90                  95

Thr Gly Phe Gly Ile Lys Val Phe Ile His Val Ile Leu Asp Gly Arg
            100                 105                 110

Asp Val Pro Pro Arg Ser Ala Glu Lys Tyr Ile Gly Met Leu Asn Ala
        115                 120                 125

Lys Ile Glu His Leu Asn Ala Glu Ile Ala Thr Val Ala Gly Arg Tyr
    130                 135                 140

Tyr Ala Met Asp Arg Asp Asn Arg Leu Asp Arg Thr Cys Lys Ala Tyr
145                 150                 155                 160

Asp
```

-continued

<210> SEQ ID NO 36
<211> LENGTH: 1039
<212> TYPE: DNA
<213> ORGANISM: Ehrlichia sp.

<400> SEQUENCE: 36

```
ttaatcagag cggttgtgct agtcctttcc gaaattcctg tgctgaatgc ggagatttca     60

ggcgatgata tagtctacag ggactattgt aacattggag tcgcggtagg taccgataag    120

gggttagtgg tgcctgttat cagaagagcg gaaactatgt cacttgctga aatggagcaa    180

gcacttgttg acttaagtac aaaagcaaga agtggcaagc tctctgtttc tgatatgtct    240

ggtgcaacct ttactattac caatggtggt gtgtatgggt cgctattgtc taccccctata    300

atcaaccctc ctcaatctgg aatcttgggt atgcatgcta tacagcagcg tcctgtggca    360

gtagatggta aggtagagat aaggcctatg atgtatttgg cgctatcata tgatcataga    420

atagttgacg ggcaaggtgc tgtgacgttt ttggtaagag tgaagcagta catagaagat    480

cctaacagat tggctctagg aatttagggg gtttttatgg ggcggggtac aataaccatc    540

cactccaaag aggattttgc ctgtatgaga agggctggga tgcttgcagc taaggtgctt    600

gattttataa cgccgcatgt tgttcctggt gtgactacta atgctctgaa tgatctatgt    660

cacgatttca tcatttctgc cggggctatt ccagcgcctt tggctatag agggtatcct    720

aagtctattt gtacttcgaa gaattttgtg gtttgccatg gcattccaga tgatattgca    780

ttaaaaaacg gcgatatagt taacatagac gttactgtga tcctcgatgg ttggcacggg    840

gatactaata ggatgtattg ggttggtgat aacgtctcta ttaaggctaa gcgcatttgt    900

gaggcaagtt ataaggcatt gatggcggcg attggtgtaa tacagccagg taagaagctc    960

aatagcatag ggttagctat agaggaagaa atcagaggtt atggatactc cattgttaga   1020

gattactgcg gacatggga                                                 1039
```

<210> SEQ ID NO 37
<211> LENGTH: 168
<212> TYPE: PRT
<213> ORGANISM: Ehrlichia sp.

<400> SEQUENCE: 37

```
Leu Ile Arg Ala Val Val Leu Val Leu Ser Glu Ile Pro Val Leu Asn
 1               5                  10                  15

Ala Glu Ile Ser Gly Asp Asp Ile Val Tyr Arg Asp Tyr Cys Asn Ile
            20                  25                  30

Gly Val Ala Val Gly Thr Asp Lys Gly Leu Val Val Pro Val Ile Arg
        35                  40                  45

Arg Ala Glu Thr Met Ser Leu Ala Glu Met Glu Gln Ala Leu Val Asp
    50                  55                  60

Leu Ser Thr Lys Ala Arg Ser Gly Lys Leu Ser Val Ser Asp Met Ser
65                  70                  75                  80

Gly Ala Thr Phe Thr Ile Thr Asn Gly Gly Val Tyr Gly Ser Leu Leu
                85                  90                  95

Ser Thr Pro Ile Ile Asn Pro Pro Gln Ser Gly Ile Leu Gly Met His
            100                 105                 110

Ala Ile Gln Gln Arg Pro Val Ala Val Asp Gly Lys Val Glu Ile Arg
        115                 120                 125

Pro Met Met Tyr Leu Ala Leu Ser Tyr Asp His Arg Ile Val Asp Gly
    130                 135                 140
```

-continued

Gln Gly Ala Val Thr Phe Leu Val Arg Val Lys Gln Tyr Ile Glu Asp
145 150 155 160

Pro Asn Arg Leu Ala Leu Gly Ile
165

<210> SEQ ID NO 38
<211> LENGTH: 177
<212> TYPE: PRT
<213> ORGANISM: Ehrlichia sp.

<400> SEQUENCE: 38

Gly Val Phe Met Gly Arg Gly Thr Ile Thr Ile His Ser Lys Glu Asp
1 5 10 15

Phe Ala Cys Met Arg Arg Ala Gly Met Leu Ala Ala Lys Val Leu Asp
20 25 30

Phe Ile Thr Pro His Val Val Pro Gly Val Thr Thr Asn Ala Leu Asn
35 40 45

Asp Leu Cys His Asp Phe Ile Ile Ser Ala Gly Ala Ile Pro Ala Pro
50 55 60

Leu Gly Tyr Arg Gly Tyr Pro Lys Ser Ile Cys Thr Ser Lys Asn Phe
65 70 75 80

Val Val Cys His Gly Ile Pro Asp Asp Ile Ala Leu Lys Asn Gly Asp
85 90 95

Ile Val Asn Ile Asp Val Thr Val Ile Leu Asp Gly Trp His Gly Asp
100 105 110

Thr Asn Arg Met Tyr Trp Val Gly Asp Asn Val Ser Ile Lys Ala Lys
115 120 125

Arg Ile Cys Glu Ala Ser Tyr Lys Ala Leu Met Ala Ala Ile Gly Val
130 135 140

Ile Gln Pro Gly Lys Lys Leu Asn Ser Ile Gly Leu Ala Ile Glu Glu
145 150 155 160

Glu Ile Arg Gly Tyr Gly Tyr Ser Ile Val Arg Asp Tyr Cys Gly His
165 170 175

Gly

<210> SEQ ID NO 39
<211> LENGTH: 2129
<212> TYPE: DNA
<213> ORGANISM: Ehrlichia sp.

<400> SEQUENCE: 39
tttacctctt tttgaagaaa tcttaaagaa aaagcatggg gcacggtcca acacatcgaa 60
ccttccccat acttttcacg agaaagatat cctaataact tagaacatct tcatcgtcag 120
gatcctttaa cggcaaagca gtcggaacat ctactaactc ttgctgcata ccagcatcag 180
cttctacaga tacttcaacc ttctcaactt cttcagttgc ttgtgtctct tgatcagaga 240
ttcctgcttc ttgctgcata ccagcatcag cttctacaga tacttcagac ttcagatcac 300
cttcagtaac accaagaact gtagactcag gttgtactgg cgcagaaact tcaggagctg 360
attctagttg ttgcgcttct ggagcaacta ccacttcttg aagcttattt tcttctagtg 420
atggtacaat cgcttctgca gcttcaacac caggtaattc tgcttcagct actacaggta 480
cttgcgctac aggttgctca agatctatca aagtaccttc ttctagaata acttctggct 540
cttccgtttt tgtttctaca gatacttcaa ccttttcaac ttcttcagtt gcttgtgtct 600
cttgatcaga gattcctgct tcttgctgca taccagcatc agcttctaca gatacttcag 660

-continued

```
acttcagatc accttcagta acaccaagaa ctgtagactc aggttgtgct ggtgcagaaa    720

cttcaggagc tgattctagt tgttgcgctt ctggagcaac taccacttct tgaagcttat    780

tttcttctag tgatggtaca atcgcttctg cagcttcaac accaggtaat tctgcttcag    840

ctactacagg tacttgtgct acaggttgct caagatctat caaagtatct tcctttagaa    900

gaacttctgt ttcttctttt acttctacag gagcttcagt tccctctagt gcttctgcaa    960

tttcttgctc ttgttgacca gagattactt ctttttgcgc tacatcagca ttagcttcta   1020

cagatacttc agactttaga tcaccttcag caacaccaag aactgtagac tcaggttgtg   1080

ctggcgcaga aacttcagga gctgattcta gttgttgcgc ttctggagca actaccactt   1140

cttgaagctt attttcttct agtgatggta caatcgcttc tgcagcttca acaccaggta   1200

attctgcttc agctactaca ggtacttgcg ctacaggttg ctcaagatct atcaaagtac   1260

cttcttccag aataacttct tgctcttctg tctcaacttc ttcaattgct ggtgcttctt   1320

gatctatttc ttgttcttct tgcgtatcta cacccgaccc tgttgctgac tcaactacac   1380

taggatctac tgtttgaggt tcctctgctg cactcttttc tatcttgaaa aaccttacga   1440

ccgctttttc tggtgcgttt atcaagtaca tacctgtacc ctcttcctct tgcaccagcg   1500

ataatgcctc cacaacggta gtataaacac caccttcagc agtagcagct ctgcccgctt   1560

ctgcctctat aaaatacacc ttccctggca aattaccatg atgcataccc gaagcaacat   1620

ctctacatgc cacatgctca tcaccaacat ataaaaccag ttcgctcggt ctccacgttc   1680

cccgtactac cctacacttg tcatacgagt acgcattagt gctggcatct ttgtcacaag   1740

cacatccttc gtagtagcca tcatctccac tggaaatggt ttcactacca attctgtaat   1800

cacttagctc tatatctata ccatacatat acgcaaatcc tcctttaatc cctctacgtt   1860

caccagcatt tgtttaagtg ctacacgata cacctaaaga gatgatatct tgcacaccta   1920

tacatacaat atgcatattt tacaacaact tgcacaaata tccgaccaac taagcacaaa   1980

taaggacgat gataacaagt atgcgaagaa atcccctaaa ccatattgcc tactatcctc   2040

taaaatacta tcaagcttta tcatgagtgc tttagttgca aattagcaaa ttgttcaacg   2100

aaatctagca atgctgtttc ctcgtgccg                                     2129
```

```
<210> SEQ ID NO 40
<211> LENGTH: 1919
<212> TYPE: DNA
<213> ORGANISM: Ehrlichia sp.

<400> SEQUENCE: 40
```

```
atgctgtgaa aattactaac tccactatcg atgggaaggt ttgtaatggt agtagagaga     60

aggggaatag tgctgggaac aacaacagtg ctgtggctac ctacgcgcag actcacacag    120

cgaatacatc aacgtcacag tgtagcggtc tagggaccac tgttgtcaaa caaggttatg    180

gaagtttgaa taagtttgtt agcctgacgg gggttggtga aggtaaaaat tggcctacag    240

gtaagataca cgacggtagt agtggtgtca aagatggtga acagaacggg aatgccaaag    300

ccgtagctaa agacctagta gatcttaatc gtgacgaaaa aaccatagta gcaggattac    360

tagctaaaac tattgaaggg ggtgaagttg ttgagatcag ggcggtttct tctacttctg    420

tgatggttaa tgcttgttat gatcttctta gtgaaggttt aggcgttgtt ccttacgctt    480

gtgtcggtct cggaggtaac ttcgtgggcg ttgttgatgg gcatatcact cctaagcttg    540

cttatagatt aaaggctggc ttgagttatc agctctctcc tgaaatctct gcttttgctg    600

gggtttcta ccatcgtgtt gtgggagatg gtgtttatga tgatctgcca gctcaacgtc    660
```

-continued

```
ttgtagatga tactagtccg gcgggccgta ctaaggatac tgctgttgct aacttctcca    720
tggcttatgt cggtggggaa tttggtgtta ggtttgcttt ttaaggtggt ttgttggaag    780
cggggtaagt caaacttacc ccgcttctat tagggagtta gtatatgaga tctagaagta    840
agctattatt aggaagcgta atgatgtcga tggctatagt catggctggg aatgatgtca    900
gggctcatga tgacgttagc gctttggaga ctggtggtgc gggatatttc tatgttggtt    960
tggattacag tccagcgttt agcaagataa gagattttag tataagggag agtaacggag   1020
agactaaggc agtatatcca tacttaaagg atggaaagag tgtaaagcta gagtcacaca   1080
agtttgactg gaacactcct gatcctcgga ttgggtttaa ggacaacatg cttgtagcta   1140
tggaaggcag tgttggttat ggtattggtg gtgccagggt tgagcttgag attggttacg   1200
agcgcttcaa gaccaagggt attagagata gtggtagtaa ggaagatgaa gctgatacag   1260
tatatctact agctaaggag ttagcttatg atgttgttac tggacagact gataaccttg   1320
ctgctgctct tgccaagacc tctggaaaag atatcgttca gtttgccaat gctgttaaaa   1380
ttactaactc cgctatcgat gggaagattt gtaatagggg taaggctagt ggcggcagca   1440
aaggcctgtc tagtagcaaa gcaggttcat gtgatagcat agataagcag agtggaagct   1500
tggaacagag tttaacagcg gctttaggtg ataaaggtgc tgaaaagtgg cctaaaatta   1560
ataatggcac tagcgacacg acactgaatg gaaacgacac tagtagtaca ccgtacacta   1620
aagatgcctc tgctactgta gctaaagacc tcgtagctct taatcatgac gaaaaaacca   1680
tagtagcagg gttactagct aaaactattg aagggggtga ggttgttgag attagggcgg   1740
tttcttctac ttctgtaatg gtcaatgctt gttatgatct tcttagtgaa ggtctaggcg   1800
ttgttcctta cgcttgtgtc ggtcttggag gtaacttcgt gggcgttgtt gatgggcata   1860
tcactcctaa gcttgcttat agattaaagg ctggcttgag ttatcagctc tctcctgaa    1919
```

<210> SEQ ID NO 41
<211> LENGTH: 3073
<212> TYPE: DNA
<213> ORGANISM: Ehrlichia sp.

<400> SEQUENCE: 41

```
tcccatgtcc gcagtaatct ctaacaatgg agtatccata acctctgatt tcttcctcta     60
tagctaaccc tatgctattg agcttcttac ctggctgtat tacaccaatc gccgccatca    120
atgccttata acttgcctca caaatgcgct tagccttaat agagacgtta tcaccaaccc    180
aatacatcct attagtatcc ccgtgccaac catcgaggat cacagtaacg tctatgttaa    240
ctatatcgcc gttttttaat gcaatatcat ctggaatgcc atggcaaacc acaaaattct    300
tcgaagtaca aatagactta ggataccctc tatagcccaa aggcgctgga atagccccgg    360
cagaaatgat gaaatcgtga catagatcat tcagagcatt agtagtcaca ccaggaacaa    420
catgcggcgt tataaaatca agcaccttag ctgcaagcat cccagccctt ctcatacagg    480
caaaatcctc tttggagtgg atggttattg taccccgccc cataaaaacc ccctaaattc    540
ctagagccaa tctgttagga tcttctatgt actgcttcac tcttaccaaa aacgtcacag    600
caccttgccc gtcaactatt ctatgatcat atgatagcgc caaatacatc ataggcctta    660
tctctacctt accatctact gccacaggac gctgctgtat agcatgcata cccaagattc    720
cagattgagg agggttgatt ataggggtag acaatagcga cccatacaca ccaccattgg    780
taatagtaaa ggttgcacca gacatatcag aaacagagag cttgccactt cttgcttttg    840
```

-continued

```
tacttaagtc aacaagtgct tgctccattt cagcaagtga catagtttcc gctcttctga    900

taacaggcac cactaacccc ttatcggtac ctaccgcgac tccaatgtta caatagtccc    960

tgtagactat atcatcgcct gaaatctccg cattcagcac aggaatttcg gaaaggacta   1020

gcacaaccgc tctgataaag aaggacataa acccaagctt aacatcatac ctcttcacaa   1080

aggcatcttt gtacttagct ctgagctcca tcactttgct catatcaact tcattaaagg   1140

tgctgagtgt agcagaggta ttttgtgact ccttaagcct agcagctata acttggcgga   1200

ttttgctcat cttcacgcgt ctttcaccca ccacgtcgcc atggcaactc atcagatcct   1260

tagacggctg gctagcaact atcttcttgt cttgttcact cttagcactc atacccaaag   1320

ctctagaagt aggagttgtg ttgattcctg caacaaaatc ttctacagta ggagttacta   1380

gacctttgcc ttcaataatt gtcttttcct gcggtttttg agtgctcact gcctgtgcaa   1440

caacgggttg agcaagcacc tcctccttgc tctctggctc cttattaaca ccctctgcag   1500

tagcctcacc ctgtggccgt atgatagcca agacctgccc ttggtaatca cttcttcatc   1560

tgcaactctc aactctgtga gaacaccagc aacaggggct gatatttcaa gagaagtctt   1620

gtctgtttca acaatgaaga gcacatcttc tgcagataca gtatctccca ccttttttcat   1680

tacccgaatc ggagcttcta gaatggattc gccaccaaga ttctcagccc taacttctac   1740

agcatcaccc ataaatacaa accagaacta aaacaaaaaa cacagattga aaggcagtgt   1800

aatcaccaaa agacactaat gtcaaaccat agatgaatac cttgttataa gtatccacgc   1860

gataacgcta tgtaattttc agcagatttt tgtaggtata aaatctcctc ttcagtcatc   1920

atacgtagaa attttgcagg cctacctgcc cataactctc cagattttac aatcttaccc   1980

ctagtgagca gtgaacctgc agctaacatg ctgccctctt ccatcactgc acgatccata   2040

acgattgatc ccatacccac aaaggcgtta ttcccaagag tacaagcatg caatatgcag   2100

ctatggccaa tagtaacgaa tttacctatt acagtatcac catgcatgct atctgtatgt   2160

actactgtat tatcttgaat gtttgtacct tcacccactt caattttatc cacatcgccc   2220

ctgagtacgg ttccatacca tatgctggca ttcttaccta tacaaacatc tcctatgata   2280

cgggcataac ctgcgataaa tgcagtgcta tctacagacg gtgatactcc tgcataaggc   2340

accagaactt ccctcataac ttcacaacct ccagtgttct ttaaacggca cagcatgata   2400

gtgtttttag cacaccataa cggagtacac caccactctt aacagatttg gctctggcac   2460

actagatgca cacatatctt gtataggact tatatattgt tgttcatgaa acgtgcgtaa   2520

tgctatggga gattactatt cttatgtatg taaattaagc aaatttagca cgtgctactg   2580

cacccagcat gttctcattt tctttaaaag gcagaccttc ctttttcgaa atagcctttt   2640

ctttaggaag cgtaatgatg tctatggcta tagtcatggc tgggaatgat gtcagggctc   2700

atgatgacgt tagcgctttg gagactggtg gtgcgggata tttctatgtt ggtttggatt   2760

acagtccagc gtttagcaag ataagagatt ttagtataag ggagagtaac ggagagacta   2820

aggcagtata tccatactta aaggatggaa agagtgtaaa gctagagtct aacaagtttg   2880

actggaacac tcctgatcct cggattgggt ttaaggacaa catgcttgta gctatggaag   2940

gcagtgttgg ttatggtatt ggtggtgcca gggttgagct tgagattggt tacgagcgct   3000

tcaagaccaa gggtattaga gatagtggta gtaaggaaga tgaagctgat acagtatatc   3060

tactagctaa gga                                                      3073
```

<210> SEQ ID NO 42
<211> LENGTH: 3786

-continued

<212> TYPE: DNA
<213> ORGANISM: Ehrlichia sp.

<400> SEQUENCE: 42

```
aaaagcttaa ggaagatgtg gcttctatgt cggatgaggc tttgctgaag tttgccaata      60
ggctcagaag aggtgttcct atggctgctc cggtgtttga gggtccgaag gatgcgcaga     120
tttcccggct tttggaatta gcggatgttg atccgtctgg gcaggtggat ctttatgatg     180
ggcgttcagg gcagaagttt gatcgcaagg taactgttgg atacatttac atgttgaagc     240
tccatcactt ggtggatgac aagatacatg ctaggtctgt tggtccgtat ggtctggtta     300
ctcagcaacc tcttggagga aagtcgcact ttggtgggca gagatttggg gaaatggaat     360
gctgggcatt gcaggcctat ggtgctgctt atactttgca ggaaatgcta actgtcaaat     420
ctgacgatat cgtaggtagg gtaacaatct atgaatccat aattaagggg gatagcaact     480
tcgagtgtgg tattcctgag tcgtttaatg tcatggtcaa ggagttacgc tcgctgtgcc     540
ttgatgttgt tctaaagcag gataaagagt ttactagtag caaggtggag tagggattta     600
caattatgaa gacgttggat ttgtatggct ataccagtat agcacagtcg ttcgataaca     660
tttgcatatc catatctagt ccacaaagta taagggctat gtcctatgga gaaatcaagg     720
atatctctac tactatctat cgtaccttta aggtggagaa ggggggcta ttctgtccta     780
agatctttgg tccggttaat gatgacgagt gtctttgtgg taagtatagg aaaaagcgct     840
acaggggcat tgtctgtgag aaatgcggag tggaggtaac ttcttctaaa gttagaagag     900
agagaatggg gcacatagag ttggtctcac ctgttgctca tatttggttt cttaaatccc     960
tgccgtcacg tataggtgct ctgctagaca tgcctttaaa ggctatagag aatatactat    1020
atagtggaga ttttgtagta attgatccgg tagctactcc ttttgctaag gggaagtaa    1080
tcagtgaggt agtttataat caggcgcggg atgcctatgg tgaggatgga ttttttgcgc    1140
tcactggtgt tgaagctata aaggagttgc taactcgcct tgatttggag gctatcaggg    1200
ctactttgag gaatgagctt gagtcaactt cttcggaaat gaagcgtaag aaggttgtta    1260
agaggctcag gcttgttgag aattttatta agtctggtaa taggccggag tggatgatct    1320
tgactgtaat tcctgttctt ccaccggatt tgaggccgtt ggtatcactg gaaaatggta    1380
gacctgcggt atcagattta aatcaccatt acaggactat aataaaccgt aataacagat    1440
tggaaaagct actcaagctg aatcctcctg cgatcatgat acgcaatgaa aagaggatgt    1500
tgcaagaagc ggtagatgct ctgtttgaca gcagtcggcg tagttacgtt tccagtagag    1560
ttggaagcat gggctataag aagtctctta gcgacatgct aaagggtaag cagggtaggt    1620
ttaggcagaa cttgcttggt aaaagggttg actattctgg taggtcagta atagttgtgg    1680
gccctagttt gaagctgcat cagtgtggtt tgcccaagaa gatggctctt gagctgttca    1740
agccgttcat ttgttctaag ctgaagatgt acggtattgc tccgactgtg aagttggcta    1800
acaagatgat tcagagtgag aagcctgatg tttgggatgt tttggatgaa gtgattaaag    1860
agcatcctat tctccttaat agggctccta cactgcatag attgggtctt caggcgtttg    1920
atcctgtatt gatagaaggt aaggcaatac agttgcatcc gttggtatgt agtgcgttta    1980
atgccgattt cgatggtgat cagatggcgg tacacgtgcc attgtctcaa gaggcgcagc    2040
ttgaggcgcg cgtgttgatg atgtctacaa ataacatctt gagtccttct aacggtaggc    2100
caattatagt tccgtctaag gatatcgttc ttgggatata ctatttaacg ttgttggaag    2160
aagatcctga agtgcgtgaa gtgcagactt ttgcggagtt cagccacgtg gagtacgcat    2220
```

-continued

```
tgcatgaggg gattgtgcat acgtgctcaa ggataaagta cagaatgcag aagagtgcag   2280

ctgatggtac tgtatctagc gaaatagttg agactacgcc tggtaggttg atattgtggc   2340

agatattccc gcagcataag gatttgactt ttgacttgat caaccaagtg cttacggtta   2400

aggaaatcac ctccattgtg gatcttgtct atagaagttg tggtcagagg gagacggtag   2460

agttctctga caaactgatg tattggggat tcaagtatgc ttcgcaatca ggtatttctt   2520

ttggttgtaa ggatatgatt attcctgata ctaaggctgc gcacgttgaa gatgctagcg   2580

aaaagatcag ggaattctct atacagtatc aggatggttt gataaccaag agcgagcgct   2640

ataacaaagt ggttgatgag tggtctaagt gtaccgattt gattgctagg gatatgatga   2700

aggctatatc tttatgtgat gagccagcgc gttcaggcgc tcctgatacg taaccttgtc   2760

gccaagtgca acttttccta aactaaagcc tcaaatcttt attatattct gttaatgact   2820

cagtggactt ttggcagaaa gagctagttt cctttggtac aaacactttt atagagggtt   2880

ctgattaatc tatccgatgg tctaaaatca aaataacata tgcaatcgtt ggctgaaaaa   2940

gctcacccgt ggtgttataa caataattcc tctccttgtt ttcatatata accttttgga   3000

aacattcctg ttggagccaa aatttctata ttttggaaac ttggcatatg gatggatgat   3060

ggctgaagta tgccatttat tttccttttg gggaggacta gagaaagcag aatagttgtt   3120

acactacttt tgaaagtaaa gtttgtagga caacccagtt taatgtggaa taaagccctg   3180

ttctttagtt ttcatgtcat aacacatatt catttctaaa catttttcct gaccacccaa   3240

tttaaagtag ttgacatccc cagaagtcac tttctctaac agaggtcaac acacttttct   3300

gtgtactgcc agacagtaaa cattttggac tttgtatgtt atatggtctc tttctgttgc   3360

aactactgaa ctcttccatt gtagcacgaa ggcggctgca gacaatatgt aaacagatga   3420

gcatgactct gatccattac agctctattt atggacactg aaatttaaat ttgctaaaat   3480

tttcacatca caaaatatta tcctactttt gatatttttc taacacttaa aaaatgtaaa   3540

aaacaattcc taactcacag accaaacaca accaggcagt agacagaatt tgaccagtga   3600

gctatcattt gagaccctca gttccacatt acttttagag aggtttttta aatgtcactt   3660

cttagcatct aaacaaatct atttacatat ttatattact tctatagtgt catgtgctaa   3720

aatttaagct cttgtattag tccgttctca cactgctata aagacatacc tgagactggg   3780

tttcac                                                              3786
```

```
<210> SEQ ID NO 43
<211> LENGTH: 3735
<212> TYPE: DNA
<213> ORGANISM: Ehrlichia sp.

<400> SEQUENCE: 43

aatgcgctcc acataactag cataacgttt tcagcaacgg cagatcttca tatataagca     60

ctgaacacct acgttccaag atcatgctct tcgcgcctgt ttacttggtg gctcagagtc    120

atcatcacta ggagttcgtg gtctgtgaga gctaacttgt gcttcttcca gcgtataact    180

agcacctccc aatcctgatg ctgaaggttg atcccacgaa taaggcataa tcccttgatc    240

ctgaggtggc acatagggag cttgtgatct tcccattcca gtactagtac ctcctagccc    300

agatgttgag aattggctag atggataagg aacattctct aggacacgta gtataatatg    360

aggggggggg ggaacgagtt gagctccctg tccggcagta cctcccaatc ctgatgttga    420

gggttgatcc catgatgttg agggttgatc ccacgatgtt gaaggttgtg catacgaata    480

gggcatcatc cctggatcat gtggtggaat atgcgaagct tgttgacttc ccattccagc    540
```

-continued

```
ggcacttcct aaccctgatg ttgagggttg atcccacgat gttgaaggtt gtgcatacga    600
atagggcatc atccctggat catgtggtgg aatatgcgaa gcttgttgac ttcccattcc    660
agcggcactt cctaaccctg atgttgaggg ttgatcccac gatgttgaag gttgtgcata    720
cgaatagggc atcatccctg gatcatgtgg tggaatatgc gaagcttgtt gacttcccgt    780
tccagcggca cttcctaacc ctgatgttga gggttgatcc cacaatgttg aaggttgtgc    840
atacgaatag ggcatcatcc ctggatcatg tggtggaata tgcgaagctt gttgacttcc    900
cgttccagca gtaccccca ttcctgatgt tgagggttga tcccacggcg caccataggg    960
tatgggtata cgctcaagaa cacgtagtgg gacactgata gcttgtgctc cttccactcc   1020
agcactagta ctccctaatc ctgatgtcga gggttgacta ggtgcagcac cggtctgctc   1080
aacagcattg aaatatcttc cgtatttctt gtcacaaata ttcatcatta ctgaaagata   1140
ccgcaatgct gtattgcgcc acttgacttc tatctgtgga attaatagcg catcttccgt   1200
aatatgctca ttgatctcct catagacatg gcacatgtct aaaaatgatt tgcgagccct   1260
gtatgccccg agctcccttc ttctgctata taaagcacac aaaatctgga gacaatgccc   1320
aatcctacct gcaacaacat gatctacatt accggtggaa gcgtatactc tatacatcaa   1380
gaacaaacca cctactgcat gcactaaagc accaccccga tacctttctc gcttgagtcg   1440
taaatcaaaa ctgtgaactc ctaaaccttc aacatatgcc tctaaatagt agagaaaatt   1500
tgccatcgct cttctagaga gtcctagacg caggcgtgca ctttcattat tacgtaccat   1560
cgcttcacat gcagctgcac tagtctcaat agcatcaata acactgtcca agcaagcctc   1620
tgtacgatga cggaaaaaac gcggtgtatt aggctcaact aactcagcaa ccttactgca   1680
aagctctatg ttatgccgca ctacgcgcaa aatcgccttt atattctctg tttcctcaga   1740
atccaaagaa gaatttaagc atctacttaa ggctgaaaat tttacatagc agtatgcact   1800
taaagctgtc actgtatgag atgcactacc atctctacgc tcactactca ctgcaccagt   1860
aaacctcgtg gcaatagttc tggcacagca gttcactata gcaataacat tcactatgat   1920
agcacatgcc ttgcctattt gtaggtgtgc cttacgctta ataaagtctt gatccatgaa   1980
cagcggcact tctttgttgc actgcgccgt gatgcagtcc tgcaacgcgt cgtacaaccg   2040
attgatcaaa ctatacaaca cccccggttc tgcgcttgaa gcaccttctg cagcagttat   2100
acagctgtta atactgtcta tcttatcagc tgccgcaaac acgacatcta caccccggag   2160
cttgacaaac gtatcgcgca attccagcat acattgacgt atagcctgca ggcatgcagc   2220
atatggcctg gaattagtca ttattgaatt acatacagtt tctttatatt ccgcagaaga   2280
gcaaccactg taggcatatc cagacataac tggagtagtg aatatacgag gcatatgcat   2340
ctaattaacc actggaacaa cttcacacct tgaaagtgta gcataccggt gtgacgcagc   2400
tcaatattaa agattatgca cttcgtgatc gtctactagg aggctcaagt tcatcatcac   2460
taggagtttg tgatctagga gagactacct gtgctccttc cagcgtagaa ctagcacctc   2520
ctaatcctga tgttgagggt tgtgcatacg aataatcttg caacggacca caaggtgcct   2580
gagcttgcag tgctccctgt ccagcaggat tacctcccaa tcccgatgtt gagggttgac   2640
taggtgaaga gggcatatgc cctggatcat gaggtagcgt ataggaagct tgtgatcctc   2700
ctattccagc cccagcactt cctagtctag atgttgaggg ttgactaggc gaaccctcag   2760
tctgcctaat attattgaaa tatctctcgt acttcttttc ccaaatacca atcattgccg   2820
aaagataccc caacatagca ctacagaacc caacttctgt ctggggattt aatagtagac   2880
```

```
ctcgcgtaac gcattcctga atctcatcat agacagtaca catgtccaaa tataattctt   2940
gtgccgtata ttctgaagct cccgctcttc tgaccttata tttatagaga gtaagcaaca   3000
tttgaagaca atgctcaatt ttactcgcaa caacatgccc tgtattaccc gtggaagcat   3060
atactctgtg cattgagaat aaactaccaa ttgcatacac taaagcttgc acatacttgt   3120
catgcctgaa acttttaaaa gcaacgctca gtcctaaact tttatatgtc ttgaaatggt   3180
gtaaaaaacc tgttctcgct tttttagcga gagctaggcg gttctttgca ctatcgttat   3240
cactcaccat ctcttcgcat tcagccgagg tagacccaac tgcatcaagc atactgttta   3300
agcaactcac cgtacgatca cggaaacaat atggaatctc cggatcaact agctcagcaa   3360
ccttattaca aagctctatg ttatgcctca ccacacgtag aatagccttt ctacgcttag   3420
tttcctcagg acccggagaa taatttaaac atctgcttaa agctgaaaat tttgcattta   3480
cgtatgcact taaagccatg ttggcatgat acgcactatg ctcatcagcc tcacctattg   3540
cactgtcaga cgcctcggtt aaggttgtga caaagcagct tgccatggta atagcattca   3600
ccaggatagc acataccta gcgatttgta ggtgtacttc acgcctcgtg aagtctggat    3660
ccatgaaccg cggcacttct ttgttgcact gcgccgtggc acagtcatgc agcatattat   3720
atgcactatg gatta                                                    3735
```

```
<210> SEQ ID NO 44
<211> LENGTH: 2322
<212> TYPE: DNA
<213> ORGANISM: Ehrlichia sp.

<400> SEQUENCE: 44

aatgtataca gtctcagatt cagaatctat aacttctttc gttactccac caatgttaat     60
ggcgaatatc tcatcgacta agcgttcagg atacttgcta tcattgtcgg tagagccatc    120
tgactttttt accgtgacat tctttttaaa agaaactcca tttacaacgg acaattcagt    180
gccattttgt agcttcgagc gcaactccac agcaaattca cgtattttct tcatacgtaa    240
tgcactcttc cattcttcag taagaataga cctgctttct tcaagtgtcc ttggtcttgg    300
aggcactact tcagtaacaa gaacgccgaa ataagcgtca ccattgctaa ccagatgaga    360
cggttttcct acggcagatg aaaacgccaa agtagtaaag gcgtttatac caagctgcaa    420
cggaaagtct ttcactaagt tgccagattt atcgagccca tgcatatcaa aattcgtcaa    480
aacaccactg atccgcgcac caaacatatc ctttagttca ttcagcaatg ccccgcggct    540
gatcatatcg tttgcttttt tcacattgct aactagcaac tcacctgcct tttgccttct    600
aatatttgaa gatatcttct ctttcagctt ttctaggtct tccttagtga tctcatgctt    660
ccttattacc ttcatgatat gccagccgac aacgctacgg aacatttcac tgacttctcc    720
ttcatttagt gcaaacacca catttcgcac acctaccgga agaacatcct tagagatatt    780
attgagtgca atatcctcta tggtgtagcc agcatcacta accaattcct caaaagactt    840
accctcttgg taagctttgt aagctagctc agcttcattt ttgtctgtaa atactaaatt    900
tagaacatct ctttgatcat gtagttcact gtttttaatc tcaacgtcta cctcttgatc    960
cgaaacaatg acatcagcaa gcaagtcgtc ttctgccatg attatataat cagcactgcg   1020
atattcaggg aaatttagag aattcttgta ctgctcctca aacaattttt gcaattcatc   1080
atcagatata tcacttcctg aaatgtctac ggcatcagaa gatatttcca ctatgtctgc   1140
cacacgatgc tgcagcaatc ccaacacaac atcttttgct aatgcatcat aataaggaat   1200
atgtaattcc gccctattag ggaataaaca ctccattaga atagtagaag gtaaagcatt   1260
```

-continued

```
gcgaatttta ttcacatagg acgactcagt cattccgctg tcagccaata cggcttcata   1320
tctctcctgg tcgaagacac cattagcatc ctgaaatatt cttatatttt tgatcagact   1380
ccgtaagcta tttgagccaa cacgtatgcc taagtcatga gcaaactttt caacgaccat   1440
gtcggctatc atgttcttga ggacaacttc cttaatacca aactgattaa tttgagcatc   1500
agacaatttg tgttgtaaca tcttctctag ttctgccaac tcgttgcggt acattatacg   1560
gtaatcccgc aatggtagac atttattacc caacattgca acgcactgtc cgttgccaga   1620
attagacaac ttacccattg gtatcatgct tccaaaagtg acaaaagcca tggcacctaa   1680
aaccgttgcc atgaccaccc aaacataaat cttccttgat cgcataacag aacgcccata   1740
gctggtcaga ttcccgaagg aatatagtaa tcagaaaaaa tctgcaagac tttttctagt   1800
tgtttatggg caatattctg aattttgcat agtagccatt acgtaatgta tggatagacc   1860
cgtattaatt tgtttcggta cgatatatga agttctaaaa agctatagaa ccttgccatg   1920
caaagcttaa gagcccttac ccatcccata tacatccgtg ttaatgaaag caccattctg   1980
ctgcttgtgc agaattctac ataagcatct cgtgccgctc gtgccgaatt cggcacgagg   2040
aattagattt aatagcagaa gagcagaggc actgtggtga ctgaagcagc aattaaagta   2100
atgtggccac agctaagtaa tatcagcaga cactgaagtg ggggaaggaa ggaacagatt   2160
gttacctggg catgatcaaa tttctggatt cagaaaagtg tggatgaaat cctggcttta   2220
ttattgatca gtgctgtgtg atacagcacc tagtcctcaa actctttctt cttaagcatc   2280
cacacttgca aaatgtgcaa cttccaatat ccatctctaa gg                      2322
```

<210> SEQ ID NO 45
<211> LENGTH: 2373
<212> TYPE: DNA
<213> ORGANISM: Ehrlichia sp.

<400> SEQUENCE: 45

```
gcaaatattt ttcttggtgc cgccctaaaa gcctgaaaaa tttaaagaaa tgttactgct     60
ctagtcattc ataaaatgca aatagcctac agaaggagta tttactgcta taggcttgaa    120
agtgcaatcg ttatttacta ttttttatac atatcgcagt acagagattt tacgcgctac    180
gcctgtgcat catagccgta ttgcatcaat aaattgtcgt tgctacgcgg gaaagctgct    240
tagcgcttga ccatttttca tacacattgt accatcatag cgagtgtggt gctcatgaga    300
gtgcgtagtg ttgccgccgg tttctcatgt tataatcttg ctgccgtttt gtgcagaagg    360
aggagtagtc tcgttttttt ccaaaagaca atgtgctgga gtgtcccggt gagcctcaag    420
gttcttgtgg gatttgtgtg ggctgttgta taaataccac gttcgaagct gtcctagtgt    480
aattcagcat atgttgagga agttgttgct atgaggttga tggtatggcg aaaagattct    540
taaacgacac agaaaagaaa ttactatctc tgctcaagtc ggtaatgcag cattataagc    600
ctcgtaccgg ttttgtcagg gctttgctaa gtgccctgcg ttctataagt gtagggaatc    660
cgagacaaac agcacatgat ctatctgtgt tggttacaca ggatttcctt gtcgaggtta    720
ttggctcttt cagtacgcaa gctatcgctc cttccttcct caacatcatg gccctggtag    780
atgaggaggc attaaatcac tacgaccgcc ctgggcgtgc tccaatgttt gcagacatgt    840
tgaggtatgc gcaagagcaa attcgtagag gtaatctgct tcagcataga tggaatgagg    900
agacatttgc atcttttgcg gatagttacc tcaggagaag gcacgagcgt gtcagtgcgg    960
agcatcttcg ccaggcgatg cagatcttgc atgcaccggc tagttatcgc gtcctgtcta   1020
```

-continued

```
caaattggtt tttgctgcgt ttgattgctg cagggtacgt gaggaatgca gttgatgtgg   1080

tcgatgcgga aagtgcaggg cttacttctc ctcggagctc cagtgagcgt actgctattg   1140

aatcgctcct gaaggattat gatgaagagg gtctcagcga gatgctcgag accgaaaaag   1200

gtgtcatgac gagcctcttc ggtactgtgt tactctcgtg ccgaattcgg cacgagttga   1260

aaagcagcct ttttaaggta gacatcctgt atatgattta agtctcacct cccaatggaa   1320

tcatgaaaca gttagaaaaa taatgaacta cgtcttatat aatctttatc gctactttaa   1380

aaatgagtaa tatattcaga tttagtagaa acatccctga ggaacaattt gttttcacaa   1440

attacattgg ttcctcacat gcaagattat taagcattaa ggaggaggat attggacatt   1500

gtataccctg taggaatagt tttttatttt cagaaataag ctcagcttac tgattgatgg   1560

caaagatagt tgatgataaa atagaaaaaa acaaagttac tcttcttaat tttgtactct   1620

tcttacctcc tttcattttt aattggttat aagtaggtga aagttaaaac ttggcaatgt   1680

ttgctttagg agttattaca attactcagg ttagtagtat agttatacgg tcatctttag   1740

taaaacatca ttcggagtca tagtcacact tatgaatatc acagaatgga tatgtgactt   1800

tggggttttt ttgtgggata ttttttgaga tatttaaggc agaagtgcca cctttacttc   1860

atttattttt atccgccccc cccccacccc accgtttctc agaaaggata aggttttcac   1920

agtaccagag acatttatct actaaaactt tgaactaatt aaaatatata gggccgggtg   1980

cagtggctca cgcctgtaat cccagcactt tgggaggccg aggcgggcgg atcacgaggt   2040

ccggagatgg agaccatcct ggctaacacg gtgaaacccc gtctctacta aaaacacaaa   2100

aaattagccg ggcgaggtgg cgggcacctg gggtcccagc tactggggag gctgaggcag   2160

aagaatggcg tgaacccagg aggcggatct tgcagtgagc caagatcgcg ccactgcact   2220

ccagcctggg cgacagaaca agactccatc tcaataaata aataaataaa taaaatatta   2280

tttaatttaa gagagttgaa atcattgaat tgattcattt aaacaaggta atttgcaatg   2340

ggtctatttt taggctattt tctttatagt agt                                2373
```

```
<210> SEQ ID NO 46
<211> LENGTH: 7091
<212> TYPE: DNA
<213> ORGANISM: Ehrlichia sp.

<400> SEQUENCE: 46

cctatggcag ctctaaactc ggcacgactg gtttctacaa gagattggtc gacattaaac     60

catgcgaaat cattgcgatc aattcttcct tctttttcct gtatagcact acagacttcc    120

tctgcactag aagccactcg tgtcccgatg cgtacgtcac ggatgcaaag ccccaggtct    180

tttacgctgc cgggtgtgtc tatatcttcc acaacataat caacgcaagc gtgaatatgg    240

ataccagaaa cagaggtaac cctgtatact aaatgctctt ccaaaacatg ttgattaaca    300

ggtaagcgcc tagcactatc accattatca gcaacaacgc cttcatgcgc aacgtaatga    360

gcagcgagct caactggcag agatgaccca ctactgttac tcaagatact agataagagt    420

acccggagat ttctgtgttt tacaccagtt ttctccacaa tatttgcagc atgcttcggc    480

tgtgacctta agatttcacg tatttcatcg gagtgttgta tgaaaatacc acagtcccca    540

cgcacaggta cagagtgaga tgcccagcga tggcgcttcc ccagatcttc ccatagcgaa    600

aggccgtgag ctactatttc ctcagcaaga ttgaaaatgt ggcctccggc aaaatctgta    660

tcttttgcac tgccagcgag gaaatctcta agtgatatac cgcctccaag tgtaagtaca    720

ttgccaaatg tattcacagt taccgccaca tgacggagaa tagtggcgca tgcatcgtgc    780
```

-continued

```
gcctgagagg ccacaaagga catgcagacc cccattttgg atacagcatc cctgccatga    840
gaaacagcgc cctgctgtac tacactagat ttatcgtatc ctaccagacc aacaacgcct    900
cgtacaacta ctcggaatac accgctcgct tcttgactga ttactgtatt acaaaaagaa    960
agctctagga cttctagcgg cataccgcta ataacgctgt aagctcttag gatgcattca   1020
tcaatatcgc ttacatcgta aaaaacccta cgagccatgt aacgtgggtt atgcctctgc   1080
agattacacg cgctgtacaa tacatgagta ggcttctcag ggactctcac atagtgtttt   1140
gccagagctt tgggaatatt gtgccaagaa catacagatc caggctcgcc ttgcctaacg   1200
tcgcggcaat ctctctcagt aagcacgagc tttacttttt tcacagctgt acggtaaaca   1260
ccctccgcct ttgtcgatgg agcaatgtca tactctaccc acatcttaac tttggctatg   1320
ggtacaccac tgttgtcctg aatactaaat atgcatgatt cgtgtactgt cagagcaccg   1380
ttcttgtagc tactaggtgc tgaagccaat aaagaatgca ccctggagaa agtagtataa   1440
ctctgaactt caaatgtggt agagtcctct tctctgacta ttgtcatatc ttcagacacc   1500
ccatccaggc atccaagaac aaaattagtt aaatcctctt cctggttttt tcctggcaag   1560
ctgttatagg caagtgcaag ggcatgccac agctggaaag gtacttgttg gaaggcagta   1620
ctgttactcg ctgtcttatg cagagctctt gctaataaat ctggggaagt tagattctca   1680
tgtatgagtg caggaggtac cgcactgccc tcacgtagag taaacccctc tgctaagagt   1740
atgaccattc tgcgtcgtgc aggatgactg ttccgatcac gacataaaaa gaaatctatc   1800
gcgctaccaa gcagtgcaac ggacgctttc gatgggtttt gcttaagcag cagagtcatg   1860
ggtgcctcat cttagttact tctagtgaca aagcggtact tttattcctg taaggacaga   1920
aaggcctgtt tttttccaga aatctacgcc ttacatgtat ggaaacctgc gcatccagct   1980
atagatatcg caaggcatag tgtgcagaat acggagctgt agcaggcgct cttacccccc   2040
agcaaagtac gcaaacctag cgacgactcg ttctcacacg ttgtgaacat acgtagtaac   2100
acaccttgac gtacctagcc tacaccacta gacatatagt gtaaaacaaa aagtaccaga   2160
tccccgtctc aggggttgta aaagtagcac attggaaacg gactgttaag tatttatatt   2220
actacttagg ttcagaataa acattcgaat tgtaatgcac cataggttag taatgcacta   2280
tgagtgagaa attacgcgaa ttggtactgt gcgatgatct tgaaatttac agttgtagac   2340
acggcgcatg cggaagatat aacctctcaa accctgcaga ggttttacta atcatatgtt   2400
ttgtctaata cctgcccaca aaaaacatat gaaagccttc gtagctcagg tcggttctct   2460
ggctgttttc atctctaggt tttaattccc aagaattcga cttttcgcgc tacctaagca   2520
tttttaatca ccgttgacta ttagagacga tataataagc tacattgatt atctgaaata   2580
tgtgatcctt ctaaaaatct ttaggtgctt tagaagaagt acatattacc ctctatggca   2640
acaacattga taatttaggt gaagtgtcac agcgtttcat tatgaaaaaa agggatactt   2700
atttatgggg aatggcacct tatgcaatat gagccttagg gattgccaca gtgttttggt   2760
ttcacagcat gagtaaggac gtggtttttt agcaagtatt tattgtgcta tgtgtgtaaa   2820
aagtaacata tgaagatcgc taaagaattc acactagaaa taagttgata cctgatgatg   2880
tagtataaag gttgagcaat agtctttttt tgactgtaaa tcccgcatgc agctttatgt   2940
gtgtttatcg caaaaagtgg gcgtttgttg caataaaaat tgaaatgcca actattattg   3000
cacataccgt gctcataccc ttaatcttgt agatgcgctg taatcacaat tcgcatgtgc   3060
agcaaaactg taatagatag cttagcacag ggacgaataa tccctagatt ctacgctgcg   3120
```

-continued

```
ggctagtgct ttttttagca tctatacggg agtatctttg atatgataaa cacacaacag   3180

catgatgctg tgcttatata gcattggtat atattctgcg atgcggacta atcaatgttg   3240

taatcaagta aaaaatgctt ttttgaaccg tatattgttc gtaaggcatg tattactcag   3300

ttgtcgtact acaaattcct cttcctctag agcatgcaag tatgaataca gcttatgtgt   3360

gcgatgcgta gattactaat gcatgattag tgtagggtat gctgtatttt ttgcatgcgt   3420

tttagatatg ttacgcaaca catgtttttc aaggacgctg tggctatcac ggatatgata   3480

gccacaatgc gctgctctta ggtcaactag gatgggctgt gggtttatgc atattaagca   3540

gtggctcctg cattcaaagc tattctttgt tgtggttaac aatcaaaaat agagagtagt   3600

ttgtttataa gaagatatgc aaaaaacctt tttatccaca gtaagcccca ggcgtatcga   3660

tgcacaagga tccaccatgg ctatgtctta aggatgtacc cagaatatga tcgtatctca   3720

ttggctaagc agagcgtcct ccagtttctg attctacaga tagtacatcc tgtaatgaag   3780

aaatggatcc ttcatcaagt gtcgttgatg gagcatcatc cggacagtac tttgtagtag   3840

tgctctcgga gttcagatca tcgcttgtac ttacatcatc atatgacgaa gaaacatcaa   3900

tcgtagcatg ttcgggttga ggctctgcca gatgcacttc ctgagagagg aggtcatgat   3960

ataaatccca cagatagtgc tgtttttaac caggtccctg aaaaactctt ctggagaaac   4020

tggcagagga gccattgcgt actgcagttt ggtaatattc atgcctatgc aagggatgcg   4080

ttgaacgcga acaagtgtag gatctggtac gcgcgtatct tgaggagtaa agactttccg   4140

tttatagaac cgatgcttca atctgagtag aagacgtcct aacggaggac atactctaaa   4200

cagtaatggt ggtgaggtct ttatattgca gtctggtgga gtgatgattg tcaggtttaa   4260

tgaacagtta tcatagagaa ctcgtccctc tccttgtata gagatctcgt atttcagtgc   4320

tgtgtttact ttgaacgcag gagtcttttc tccctctgta gactgcggca ctttcaggag   4380

aaagtccaaa ttctcgcaga ctgcaatacg ctctggtgtt attgcatcta cctgttttat   4440

attgctacac gctgatacat agatgcgatt tagtagattt agcgtggcac ctgcatcgct   4500

aaagaagtat tctttatcca aagcatgttt tataggccaa attacatcga aacataccca   4560

ggctgacagc cctccttgat ggcaatggct tgctatttca tcaagcagtc taatgtctgg   4620

gacgacccca tgacgatcat ctcggaacat tttttgcagc atggctatcg cgagacttct   4680

ttcacgatag cggcgcaaaa atacccctct acttactcca tatgttctct gacatacaag   4740

attaaggtta gtgatgctcg acgattttat gctcctttct agtcttgcaa tatgagcact   4800

tacattttgt ctagggtaaa atgttttatt gatgcaccag tcacatctat gcatatcgat   4860

tagaaactga tggccgtaca agttagactt gtttttatac gaatcgcaaa gtgcgctgtg   4920

gaaggaaaac cccgatgcac cttccagcca tttttttcttt tgagaatact ttaaacttac   4980

atctatagaa gggcgatgat ccttatgctt agctttacta tccttacttg cgtcagagct   5040

attgtgtgtg cagatatgta ctgaattagc ctcatcttct gccttagaga cagcactact   5100

agatgttgaa aaaattgaga ttatcctaaa aaacagtgct ctcaaatagt tcaggatacc   5160

actgacagtt cttctagatc cattgtgagt attcttttta cgcaacttaa acctccatgt   5220

tacacaatat gcagctttgc tattttcctt tctcatgtgg atgcgctaat ctgcgtttga   5280

tcagtagtaa cgacgcgcgc tgtagtgtag ttgttccaac aatgaacatg caaaattgct   5340

gcaatactta acttcctcct tctgaaatgc atttcccaca tttcaggctt ttactatttc   5400

atgctttaca tcgtgtagcg catttttgaa aaaacaagat attagtacag catttctggt   5460

aaaccagtaa ttgttcctat tcaaggtctc tgaatcatga cgaccacttt ctttgcggca   5520
```

```
attgagaaat tcctcacata tttgatatac accgcacttt ttgtttttgc tccatgaatg   5580
gattaccgga tccaagggca ttgctatact tcactgtgca acactactgt aagtgtcgtt   5640
agcatatcat gaaattatta aataatatgt agaatatgtt gtgcaaaaga cgcttataac   5700
aacttaatag tgaatttcat gaaatttgtg agtagttttc tatcggaata cgtgttttag   5760
caacgctata gatggggtaa gatcgctttt atgttcagaa attcgcaacc atactatttt   5820
ctctgtatgc gaagacatgt cttagcgtca agccacatat gtggggtact taagcgttgc   5880
cttgcacgca acagctccac attgcctgga tttttcttaa catcagctaa ttatatacca   5940
gactcacaga tatactacgc gtaaccagtc atattatgca gcacctgtac atgttctctg   6000
gggagttcct ttatgaaacg agacattttc atggattggc tccagttatt gatttctctc   6060
attgcagcac atgatatgta tagctgctct ctagctcttg ttatgccaac ataggctaag   6120
cgcctctctt cttccagagc gtttccagtt atgtcattca tggatttttc gtgtgggaag   6180
actccttcct cccatccggg gaggaaaacc aacgggaact ccaacccctt tgcggcatgt   6240
aatgtcataa cgtgtacgta gttattgtct tcttctaaag aatcattttc tgccactaag   6300
ctaatgtgtt ctaaaaactt cgacacatca tcgaatcctg atacggctga gaagagttcc   6360
tttatgttct ctattcttga tagacctgat tccccgtctt tttttagaga ttctatatat   6420
ccagagtcat gagcaatagc ttttagtaca ttgacggatg aatctctact taacatttct   6480
ctccaatcat caaactgctt gagaagatct tgcagaatgt tggatgtatt atcagatagt   6540
aatccatctt ttatcattga gtgtccggct tcagttaggg aaatactgtg ctttctccca   6600
tatgcacgaa gcttattgac agtagaagtt ccgagcttgc gtttgggctt atttataatt   6660
ttctcaaacg ctatgtcgtt attggggttg actactactt tgagatatgc aacaagatcg   6720
cggatttcta ccctatcata gaacttggtt ccgccgataa ttttgtaagg tataccatat   6780
cttacgaaga actcctcgaa gactctagtc tgaaagctgg ctcttactag aacagcagtt   6840
tcactaaatt tataatcgta agagctctta atatgctcac taatgtattg agcttcgagc   6900
cgtccatcga agaacttcat taaaccaact ttttgtcctg cctgattgtg cgtccataat   6960
gttttttaa ggcgggattt attattatca attatcgctg atgctgaggc taatatgtta   7020
gacgttgacc tataattaca ttccagcctt attactttag cgtctgggaa atcatctgaa   7080
aatctgagta t                                                          7091
```

```
<210> SEQ ID NO 47
<211> LENGTH: 3947
<212> TYPE: DNA
<213> ORGANISM: Ehrlichia sp.

<400> SEQUENCE: 47
```

```
ggtatatcga tagcctacgt agtcactcct tattattaaa aaggaagacc aagggtatta     60
gagatagtgg aagtaaggaa gatgaagcag atacagtata tctactagct aaggagttag    120
cttatgatgt tgttactggg cagactgata accttgccgc tgctcttgcc aaaacctccg    180
gtaaggactt tgttaaattt gccaatgctg ttgttggaat ttctcacccc gatgttaata    240
agaaggtttg tgcgacgagg aaggacagtg gtggtactag atatgcgaag tatgctgcca    300
cgactaataa gagcagcaac cctgaaacct cactgtgtgg agacgaaggt ggctcgagcg    360
gcacgaataa tacacaagag tttcttaagg aatttgtagc caaaacccta gtagaaaatg    420
aaagtaaaaa ctggcctact tcaagcggga ctgggttgaa gactaacgac aacgccaaag    480
```

-continued

```
ccgtagccac ggacctagta gcgcttaatc gtgacgaaaa aaccatagta gctgggctac    540
tagctaaaac tattgaaggg ggtgaggttg ttgaaataag ggcagtttct tctacttctg    600
tgatggcgct tgaactccgg gtatgctggt gattttgagg tattgggagt tataccgcaa    660
gtatataact taaatactgc atcgtaagga tatccttctg tttctgagac actggtaagt    720
atgcccatta cctatgaatc tctatgtaga tgtaataaga gcatacacag taactcttat    780
tattaaaaac aagaccaatg gtataaggga tagaagaaga gtattattag agaggatgaa    840
gtagatacag tatatctact agctaaggag ttagcttatg atgttgttac tggacagact    900
gataagctta ctgctgctct tgccaaaacc tccggtaaag acatcgttca gtttgctaag    960
gcggttgggg tttctcatcc cagtattgat gggaaggttt gtaggacgaa gcggaaggct   1020
ggtgacagta gcggcaccta tgccaagtat ggggaagaaa cggataataa tactagcggt   1080
caaagtacgg ttgcggtttg tggagagaag gctggacaca acgccaatgg gtcgggtacc   1140
gtgcagtctt taaaagactt tgtaagagag acgctaaaag cggatggtaa taggaattgg   1200
cctacttcaa gggagaaatc gggaaatact aacacaaagc ctcaacctaa cgacaacgcc   1260
aaagctgtag ctaaagacct agtacaagag cttaatcatg atgaaaaaac catagtagct   1320
gggttactag ctaaaactat tgaaggtggg gaagtggttg agattagggc ggtttcttct   1380
acttctgtga tggtcaatgc ttgttatgat cttcttagtg aaggtttagg tgttgttcct   1440
tatgcttgcg tcgggctcgg tggtaacttc gtgggcgtgg ttgatgggca tatcacaatc   1500
cgttgggctt cgaccctata tgctcacagc aagtcactag gcaaaattgg agctgcatca   1560
ctccgaaaca gactacgatc agcgattctc catacctagt agatcagtac agtggcttta   1620
tactcttacc cagcatgaaa tacttgctat ctaagaatct cctctaaaac tttccagagg   1680
ttatctgtac ttcgagagga agctaatctg cgactaatac ggatggtgtt tataatatca   1740
ctcctaaact tgcttatagg ttaaaagctg ggttgagtta tcagctttct catgaaatct   1800
cggcttttgc gggtggcttc taccatcgtg ttgttggtga tggtgtttat gatgatcttc   1860
cggctcaact acctacaaat tgataggtac actaaaagcc cacgtaataa ctctcattat   1920
taaaatgagg aagatgaagc agatacagta tatctactag ctaaggagtt agcttatgat   1980
gttgttactg gcagactgta taaccttgct gctgctcttg ccaaaacttc cggtaaagac   2040
tttgttcagt ttgcgaatgc tgtgaaaatt tctgccccta atactcgtgc cgaattcggc   2100
acgagcggca cgagctatat ttaacttata agaaatcagc agactatttt tcaaattgat   2160
tgtacaattt accttacctg ggaatatatg tgagaaccct ggcttctcta ccttttaaca   2220
atatttgcta ttattatttt taaagtatta gctattgtgg ttatgtggaa ttaaatatca   2280
acttggtttc aatttgcatt ttcctaatga ggaatgctgt tgactacgtt ttgcatgtgc   2340
ttgtgggcca tttatgtatc ttcattacat ttgttaaggg atcgtgtgag acattcattc   2400
atttttattt tattgtcatt ccattacttg ttaactcttt ctactagtct tttaaaataa   2460
tgtttaattt atcacctttt tatttatggc tttcttttct tggccttgtt ggacagatat   2520
ttttcctacc ccacatcatg aagacagtcc cctatgttct tgtttgtttg ataaaatacg   2580
tagactttaa ctcttgaatg agatgcataa cttacctcaa attaagtttg tgaatgttag   2640
taggtagagg gcaacataca aattgtatat gaatatattg ttgttccatc atcattggtt   2700
taaaaaattc ttaattctcc tgatgaaatt acttgggatg tctgtcaaat aaatcttaaa   2760
atactttttg ttaattttta ttaagtagtg tactgaaatt aaattggaac tggttaaatc   2820
tatagattgt taaattgaat atataaaggt taaattgaaa ttcattcaat tcatgtactt   2880
```

-continued

```
cttaaatttc tatcagctaa cttttataat ttttggtata gaaatcatac acaacataaa   2940
aaaatactaa gtattttatc tatttttgat acaaatgtaa attaaaattt aattttttac   3000
tgctaatatt acttatttaa aattttaact cttaatcatt aaatatctct aatatcacat   3060
atatatttca atgtatataa ttataaagta acacttcttc cttgtcaatt tgtgtggctt   3120
gtactaaatt gtattaattt ttctttattt aagatgtctt tatttcctct ttattcttca   3180
ataatatgtt ctctggaatc aaaatcaaga tttacatttc ttttatttct acacttgaga   3240
gatatggtgt cagttcttcc tggtttccat gatttccata gttcccactg ttttcatgaa   3300
atccactgtt aagcaattta tcccctttat ataaagtgtc atttttttgt tgttactttc   3360
tttgttgtat ttagttttta gaaatttgat tatgatatgt tgtagtgtag atttcccagg   3420
tgttttcttg tttgatgttc tctagtttgg tggctacctt gttgaatcta taggtttttt   3480
tatttacact taactaaatt tgagaagttg tcagccatta ttttcttaaa ttacttttga   3540
ctttttttagc ctctactatt tctatttctt tttttgaggc tctgatgaca tggatatgag   3600
gtcttttgtt ttagttccac aactcgtgcc gctcgtgccg aattcggcac gagaaaagga   3660
caaatgttgt acagtttcac ttacatgaga tacctagcac aggccttttc atagggaaag   3720
tggaatagag gttaccagag ctcagggcat tgggaaatgg ggagtattgt ttaatgggca   3780
cggagtttct gtttgagatg aggaaaaagt tctggaaatg tgcagtattg tacaagctca   3840
caaattgtac taagctcatc aatttaatgt taatgccact gaattgtcta cttaaaaatt   3900
gttaaaatgt taattttcat attgtgtata tttgaccaca gtttaaa                  3947
```

<210> SEQ ID NO 48
<211> LENGTH: 5521
<212> TYPE: DNA
<213> ORGANISM: Ehrlichia sp.

<400> SEQUENCE: 48

```
ttcacctggc caaatcttat tggatcttca ggacaaagac caagaatctg cttctccaag     60
aagcattctc tgacccccac ctacctatct gactcttagc ttagattcct aatggtgtga    120
gtgtgtcaga gcctttactt agtctaagcg taactgtaaa aacatctttt caaaagtctc    180
tgcatgactg tctaggtctc acctatcaca ctgtaagcat ctggaaaaca aagccactga    240
gtcttccttt taccaaaaag gcctagcctt gtttttgaca aatggcaaga acacattaga    300
tgtttgttga gagaacaaaa ggagagaact cattatgaaa ctctggacaa catttatata    360
cctctctaca ttttttgtgt tggaggttag ttttcttttc taataatttg atttctttgg    420
atacatcgag gcaatacact taagaagcaa gaagattggg gccagccttc tagactgttc    480
aaagggttac acccaacaga agggaaatat tcccgagatg accttggtgc ctgttggggt    540
gatcaagccc aacaccaggc cgtcggggct acaaagtcca gtggggtcaa aggaatgaga    600
aaagacaagt taagagtgca taaagtgtat ccaggggggct aacgctagat tggaggctgt   660
gaaggcccgg agctctggga gcccacacta tttattgctg gagtagaaag gtagcagtgc    720
atcaagtgta gctgtgacag tttagcattt tctttgacac atatagaata tgctctgctg    780
cttgatataa tggagagcat gtttatgagc ctgggagagc aaccaacaag tctgtgcaca    840
ttccagaggc tacgaggggc tttatgccct gagccctgga ttccatccaa gccgcaaggg    900
gttttatgcc ctgggcttag atttgtggcg tggcagtgca gccttccacc ctttggcaca    960
gagcttggtg ttccaaaggc cacgaggggt tttagaccct ggaccccgga catcctccaa   1020
```

-continued

```
ggatctttta tattacgaca aacaagccag tcctgcctca gctcttctac caacaggtac   1080
ctttggccaa atgtctgaaa tagggttaca gattctataa ctgatggatc tcctaacagg   1140
ataattgagt gtcttatagg gaagttgaca ttttttggt tactctactc caaggcattg   1200
aattgtttac agtttttatt tgttcatggt ggaaactgtg gctgtatatt atttcttatt   1260
ggtgtaggct agtatgataa actttgctta tcttttagtt tgttatcaac ccatagtagc   1320
acatcaaact gaatctacaa aaaaaactat ggaaaaccct tatgtatgtg tttcatgagc   1380
aaaattacct ttgcttcaaa ttccaacctt ggaaatgttt cttgagtttc tacaggtagt   1440
ctaataccag attctatgta ccttgttgta acctcgtgcc gaattcggca cgagctcgtg   1500
ccgtgctgag tcattatttc ctctcataga tatagtgctt tctgaaggag gaatatccta   1560
ccaaaattta actgacattg cagtaataat aggccctgga agctttactg ggttaagagt   1620
atctctggca acagcacaag gttttgagct tgcttctagt gttgctgttc atgggatcag   1680
tcttcttgaa ctacaagcat attcaatttt gtgtgcttct gaacaaactg aagaagatat   1740
agttgctgtg atagaatcta caaaagccga ttttgtctat tatcaaatgt tcaataactc   1800
cctcattccc ctaacaggtg tgcatttagt gcctctaaat gaagtgcctc aaggcaaaat   1860
attgaagggc tcccctgcta tagctttgga taccaagtct attgggttgt accttattta   1920
taaactatca aatcgacttc cgaaaactac acttgccccc atttattcgc gcttttacca   1980
ctagagtgtc catgataatt taactgataa catcaatcgg gctagatatg tgtctagctt   2040
ttgtgcgtaa gctcttatgg aaataagtgt gatattttgc gagcacatgg tgatggagag   2100
ctcatctaag gcagcctcag taacatgccc cgcgtctatg aattgtgatt gtaatgcgta   2160
ttaaggattc cacaatttcc tgtgacaacc actaaaagta gtctacaagc tataaactct   2220
taaatctata gattgctagg gctgataaag aacctttagc attagaagcg tagagagaca   2280
ctgatgggtt agaatttgat acaaaaacat gaccttatta ctacaatagt ttacttgtga   2340
gcagtgcaca ccaagaatat aacattaagc ttctgagagg atacactcac tgagactctg   2400
tgagatctga cgtaccctta cccaatctac tacactctac ctctggcaac gcattctaca   2460
gagcacgttt tagcgtgaaa atcttcacac gaagataccg ttgtattgtg gctccagtta   2520
gcgtcactaa gtattgagct agcagttcca ccttgattaa aaggtactgc atcttataca   2580
gactttagca gtcccattac atactcacct tgatctagaa aacaatgatc tagccgcacc   2640
taacatttct atcttcaaaa aaccacttat agcgtttttc tctccaactt ctaaaacata   2700
ctctatatac tttaaaggtt ttattgagga aatcagaaaa gatttttcaa gtaacactga   2760
gctttctttt aaacatctgg tgcagagata tgtactacac aaactgaaat ataaacgttt   2820
tggaaaatat ctataaatat gaaacattaa gttttaagca taatatgctt taaaactagc   2880
agaatatatt gcaacacata ttctatacat tcttgcttgc attagaataa aaatagattg   2940
ctcaaggaaa ctgctaggta tacatatacc ttttcaccaa attagcagtg tataccttct   3000
ggaatactca taagcgtctt gtgaatacga tgtttttcta cactgcaggt aagatgacgt   3060
ttggcctatt tttcgtatca gcagggctca ggtaaatgat gtatgtgcgg tgttattatc   3120
tatcaacaaa tgcgtatggt gtatttttga tgccgaaaat tgtctccatc tcacaggcag   3180
catatcttac tcttgtaagc atataaaatt ttagttcaca gtgttaagaa acactgttat   3240
ttgatccctt gaaggtatgc ttaaacggtt tgaaaatgca cgtcctgcag tgtgtttgta   3300
atacctgttc taacaaccaa gagctttaag catctcgaaa aagcttttaa gaaattgatg   3360
cgtcccctag tagtgccgcg gtaagcatta ttatgaacgc tcaaaggtat agtattttgg   3420
```

-continued

```
catattgaat attacagtac agcatcaata tacagtttaa aactcaagta tcacatctcc   3480
tactgctatc atctatgctg gaaaaactca tttataccct gtgatgcgct tttaagagtg   3540
ttacactgtt aattctttcc tctgtttaaa tgttatgcag aacatgagta ataaaactaa   3600
tagaagatat gtgagaagag gcattcagcc cattacttac tcatggatta gataagaaac   3660
tagagccacg tttgcttctg tttttcgtga catgcttatg tagaattctg cacaagcagc   3720
agaatggtgc tttcattaac acggatgtat atgggatggg taagggctct taagctttgc   3780
atggcaaggt tctatagctt tttagaactt catatatcgt accgaaacaa attaatacgg   3840
gtctatccat acattacgta atggctacta tgcaaaattc agaatattgc ccataaacaa   3900
ctagaaaaag tcttgcagat tttttctgat tactatattc cttcgggaat ctgaccagct   3960
atgggcgttc tgttatgcga tcaaggaaga tttatgtttg ggtggtcatg gcaacggttt   4020
taggtgccat ggcttttgtc acttttggaa gcatgatacc aatgggtaag ttgtctaatt   4080
ctggcaacgg acagtgcgtt gcaatgttgg gtaataaatg tctaccattg cgggattacc   4140
gtataatgta ccgcaacgag ttggcagaac tagagaagat gttacaacac aaattgtctg   4200
atgctcaaat taatcagttt ggtattaagg aagttgtcct caagaacatg atagccgaca   4260
tggtcgttga aaagtttgct catgacttag gcatacgtgt tggctcaaat agcttacgga   4320
gtctgatcaa aaatataaga atatttcagg atgctaatgg tgtcttcgac caggagagat   4380
atgaagccgt attggctgac agcggaatga ctgagtcgtc ctatgtgaat aaaattcgca   4440
atgctttacc ttctactatt ctaatggagt gtttattccc taatagggcg gaattacata   4500
ttccttatta tgatgcatta gcaaaagatg ttgtgttggg attgctgcag catcgtgtgg   4560
cagacatagt ggaaatatct tctgatgccg tagacatttc aggaagtgat atatctgatg   4620
atgaattgca aaaattgttt gaggagcagt acaagaattc tctaaatttc cctgaatatc   4680
gcagtgctga ttatataatc atggcagaag acgacttgct tgctgatgtc attgtttcgg   4740
atcaagaggt agacgttgag attaaaaaca gtgaactaca tgatcaaaga gatgttctaa   4800
atttagtatt tacagacaaa aatgaagctg agctagctta caaagcttac caagagggta   4860
agtcttttga ggaattggtt agtgatgctg gctacaccat agaggatatt gcactcaata   4920
atatctctaa ggatgttctt ccggtaggtg tgcgaaatgt ggtgtttgca ctaaatgaag   4980
gagaagtcag tgaaatgttc cgtagcgttg tcggctggca tatcatgaag gtaataagga   5040
agcatgagat cactaaggaa gacctagaaa agctgaaaga gaagatatct tcaaatatta   5100
gaaggcaaaa ggcaggtgag ttgctagtta gcaatgtgaa aaaagcaaac gatatgatca   5160
gccgcggggc attgctgaat gaactaaagg atatgtttgg tgcgcggatc agtggtgttt   5220
tgacgaattt tgatatgcat gggctcgata aatctggcaa cttagtgaaa gactttccgt   5280
tgcagcttgg tataaacgcc tttactactt tggcgttttc atctgccgta ggaaaaccgt   5340
ctcatctggt tagcaatggt gacgcttatt tcggcgttct tgttactgaa gtagtgcctc   5400
caagaccaag gacacttgaa gaaagcaggt ctattcttac tgaagaatgg aagagtgcat   5460
tacgtatgaa gaaaatacgt gaatttgctg tggagttgcg ctcgaagcta caaaatggca   5520
c                                                                   5521
```

<210> SEQ ID NO 49
<211> LENGTH: 1938
<212> TYPE: DNA
<213> ORGANISM: Ehrlichia sp.

-continued

<400> SEQUENCE: 49

```
ttgaggagta ttaagcaagt ctccgaaaga tgagtttgac aaatgctttc gagactcttt     60
aagcatcttt aaaaagcatt tttctgtaac cttatcagaa tataaagcct catgtaacgc    120
tgtatctccc atatgagaaa ggagtgcttg acagctatct gggcattttt tcgcaattta    180
cttatatagc ttaccgtcac cattagcagc tgctatatgt aaagccgtct taccataagc    240
atctctctgc gttgctggag cccctttatc caagagcaac ctagcagtct tctggttgcc    300
agcagctgtt gctaaatgca aggctggagt tccagtgtga tccgtagacg aaagatctgc    360
acccctctgt aaaaggaaat ttacaatcct attagcctct ttaaggttac ttgcctcatt    420
tgccacttga actgcagcag ctaaagggct catagatccg gtaggagtat ttatatgtgc    480
cccagcttct acaacacgct ttaaatgctt tatagcttta ccccccctgaa agcaccctcc    540
ttgtataccc acagaaatag ctggttctgg agacgcattt acatcagcac tgtttttaat    600
taacgtcttc actgcagcat attgaccact agttagtgct tcagcggtca aagttgtctt    660
ttttccttca ggagttgtaa tttcttcatt tacactaatc acttcagtgg taataagatg    720
cctcaataca tctgctgcac cttttcttac tgcctcgaca gcaacatgct gcgggtaagg    780
ctcatatctc attaacatgt caagtgctgg tagcgatact tttccaccac ttgcttcacg    840
aatcgcatat acacctggag taggaacacc atcctttaca ggaaacttag aataactact    900
cttccttcca agagcctgct gcaatatctc taaatttcca tcctttgctg cgtaatgtat    960
tatagttcca ccatcatgtg accgagcatc tacgtccatg ctattacagc gtaacatagt   1020
cttaacaccc tcagtgttgc cccctttata cgcagctacc acaggcgttt cacctgtcac   1080
tggagatggt acattgattg atggaatatt acgcacattc tcaatcaaca tctgcaattt   1140
aacgcttacg cctttatggc ttggctcatc ctcaactatc atgtgaatag gcgctttgcc   1200
attcggtgct aattgattta caacagactc aggagtgcat cttaccacct gctcaaaaac   1260
ccccactgtt gatttttgtg ctgcagcatg tataggtgca ttacctgcaa tatctaaatt   1320
agtaaaaggt tcctctccat acctatgata tgcttcctcc aataccottt tcgcaagagg   1380
atcaaaattt ggggtcccat tagaagatac aaaatgcacc agcgttgatg cgtcctctgg   1440
attaggacat gtaaagagag attttacttc tgaagaagct gagccataca ctttatctgc   1500
aatgttcatg gccttctcga agatcttctc agcctccggt atagccttct aatagcatac   1560
tgtactgcac tcatcccttt tttatccggg aatattagtg cctctgcaca ctgcgattgc   1620
cctcaatatt tgacgacacc gcttcttgca tcttgtcaat gtatgataaa acatcccgcc   1680
ttggccattg ctttgcaaca atgtggcaaa cggtttcacc agcatcattt gcaacgctaa   1740
tatcacttaa ccttgagaga agatgcttta ctttctggtg atccatacgc tccgtagcaa   1800
tatgaagcgg agtgtttcca cccggtccct tagcattaac atctgctata agagctttgt   1860
cgcatagtac atcaagattg cctaaagcat tttgcctac tgaagatgca gctgtatgta   1920
atggcgtatt accatcta                                                  1938
```

<210> SEQ ID NO 50
<211> LENGTH: 578
<212> TYPE: PRT
<213> ORGANISM: Ehrlichia sp.

<400> SEQUENCE: 50

```
Met Tyr Gly Ile Asp Ile Glu Leu Ser Asp Tyr Arg Ile Gly Ser Glu
 1               5                  10                  15
```

-continued

```
Thr Ile Ser Ser Gly Asp Asp Gly Tyr Tyr Glu Gly Cys Ala Cys Asp
            20                  25                  30

Lys Asp Ala Ser Thr Asn Ala Tyr Ser Tyr Asp Lys Cys Arg Val Val
        35                  40                  45

Arg Gly Thr Trp Arg Pro Ser Glu Leu Val Leu Tyr Val Gly Asp Glu
    50                  55                  60

His Val Ala Cys Arg Asp Val Ala Ser Gly Met His His Gly Asn Leu
65                  70                  75                  80

Pro Gly Lys Val Tyr Phe Ile Glu Ala Glu Ala Gly Arg Ala Ala Thr
                85                  90                  95

Ala Glu Gly Gly Val Tyr Thr Thr Val Val Glu Ala Leu Ser Leu Val
            100                 105                 110

Gln Glu Glu Glu Gly Thr Gly Met Tyr Leu Ile Asn Ala Pro Glu Lys
        115                 120                 125

Ala Val Val Arg Phe Phe Lys Ile Glu Lys Ser Ala Ala Glu Glu Pro
    130                 135                 140

Gln Thr Val Asp Pro Ser Val Val Glu Ser Ala Thr Gly Ser Gly Val
145                 150                 155                 160

Asp Thr Gln Glu Glu Gln Glu Ile Asp Gln Glu Ala Pro Ala Ile Glu
                165                 170                 175

Glu Val Glu Thr Glu Glu Gln Glu Val Ile Leu Glu Glu Gly Thr Leu
            180                 185                 190

Ile Asp Leu Glu Gln Pro Val Ala Gln Val Pro Val Val Ala Glu Ala
        195                 200                 205

Glu Leu Pro Gly Val Glu Ala Ala Glu Ala Ile Val Pro Ser Leu Glu
    210                 215                 220

Glu Asn Lys Leu Gln Glu Val Val Val Ala Pro Glu Ala Gln Gln Leu
225                 230                 235                 240

Glu Ser Ala Pro Glu Val Ser Ala Pro Ala Gln Pro Glu Ser Thr Val
                245                 250                 255

Leu Gly Val Ala Glu Gly Asp Leu Lys Ser Glu Val Ser Val Glu Ala
            260                 265                 270

Asn Ala Asp Val Ala Gln Lys Glu Val Ile Ser Gly Gln Gln Glu Gln
        275                 280                 285

Glu Ile Ala Glu Ala Leu Glu Gly Thr Glu Ala Pro Val Glu Val Lys
    290                 295                 300

Glu Glu Thr Glu Val Leu Leu Lys Glu Asp Thr Leu Ile Asp Leu Glu
305                 310                 315                 320

Gln Pro Val Ala Gln Val Pro Val Val Ala Glu Ala Glu Leu Pro Gly
                325                 330                 335

Val Glu Ala Ala Glu Ala Ile Val Pro Ser Leu Glu Glu Asn Lys Leu
            340                 345                 350

Gln Glu Val Val Val Ala Pro Glu Ala Gln Gln Leu Glu Ser Ala Pro
        355                 360                 365

Glu Val Ser Ala Pro Ala Gln Pro Glu Ser Thr Val Leu Gly Val Thr
    370                 375                 380

Glu Gly Asp Leu Lys Ser Glu Val Ser Val Glu Ala Asp Ala Gly Met
385                 390                 395                 400

Gln Gln Glu Ala Gly Ile Ser Asp Gln Glu Thr Gln Ala Thr Glu Glu
                405                 410                 415

Val Glu Lys Val Glu Val Ser Val Glu Thr Lys Thr Glu Glu Pro Glu
            420                 425                 430

Val Ile Leu Glu Glu Gly Thr Leu Ile Asp Leu Glu Gln Pro Val Ala
```

-continued

```
        435                 440                 445

Gln Val Pro Val Val Ala Glu Ala Glu Leu Pro Gly Val Glu Ala Ala
    450                 455                 460

Glu Ala Ile Val Pro Ser Leu Glu Glu Asn Lys Leu Gln Glu Val Val
465                 470                 475                 480

Val Ala Pro Glu Ala Gln Gln Leu Glu Ser Ala Pro Glu Val Ser Ala
                485                 490                 495

Pro Val Gln Pro Glu Ser Thr Val Leu Gly Val Thr Glu Gly Asp Leu
            500                 505                 510

Lys Ser Glu Val Ser Val Glu Ala Asp Ala Gly Met Gln Gln Glu Ala
        515                 520                 525

Gly Ile Ser Asp Gln Glu Thr Gln Ala Thr Glu Glu Val Glu Lys Val
    530                 535                 540

Glu Val Ser Val Glu Ala Asp Ala Gly Met Gln Gln Glu Leu Val Asp
545                 550                 555                 560

Val Pro Thr Ala Leu Pro Leu Lys Asp Pro Asp Asp Glu Asp Val Leu
                565                 570                 575

Ser Tyr
```

```
<210> SEQ ID NO 51
<211> LENGTH: 125
<212> TYPE: PRT
<213> ORGANISM: Ehrlichia sp.
<220> FEATURE:
<221> NAME/KEY: VARIANT
<222> LOCATION: (1)...(1)
<223> OTHER INFORMATION: Xaa = Threonine or Lysine
<221> NAME/KEY: VARIANT
<222> LOCATION: (4)...(4)
<223> OTHER INFORMATION: Xaa = Glutamine, Threonine or Proline
<221> NAME/KEY: VARIANT
<222> LOCATION: (7)...(7)
<223> OTHER INFORMATION: Xaa = Isoleucine or Leucine
<221> NAME/KEY: VARIANT
<222> LOCATION: (9)...(9)
<223> OTHER INFORMATION: Xaa = Glutamic Acid or Lysine
<221> NAME/KEY: VARIANT
<222> LOCATION: (11)...(11)
<223> OTHER INFORMATION: Xaa = Glycine or Aspartic Acid
<221> NAME/KEY: VARIANT
<222> LOCATION: (71)...(71)
<223> OTHER INFORMATION: Xaa = Alanine or Valine
<221> NAME/KEY: VARIANT
<222> LOCATION: (81)...(81)
<223> OTHER INFORMATION: Xaa = Alanine or Threonine
<221> NAME/KEY: VARIANT
<222> LOCATION: (94)...(94)
<223> OTHER INFORMATION: Xaa = Asparigine or Aspartic Acid
<221> NAME/KEY: VARIANT
<222> LOCATION: (96)...(96)
<223> OTHER INFORMATION: Xaa = Aspartic Acid or Glycine
<221> NAME/KEY: VARIANT
<222> LOCATION: (97)...(97)
<223> OTHER INFORMATION: Xaa = Valine or Methionine
<221> NAME/KEY: VARIANT
<222> LOCATION: (98)...(98)
<223> OTHER INFORMATION: Xaa = Alanine or Glutamine
<221> NAME/KEY: VARIANT
<222> LOCATION: (100)...(100)
<223> OTHER INFORMATION: Xaa = Lysine or Glutamine
<221> NAME/KEY: VARIANT
<222> LOCATION: (101)...(101)
<223> OTHER INFORMATION: Xaa = Glutamic Acid or Alanine
<221> NAME/KEY: VARIANT
<222> LOCATION: (102)...(102)
<223> OTHER INFORMATION: Xaa = Valine or Glycine
<221> NAME/KEY: VARIANT
<222> LOCATION: (105)...(105)
<223> OTHER INFORMATION: Xaa = Glycine or Aspartic Acid
```

-continued

```
<221> NAME/KEY: VARIANT
<222> LOCATION: (107)...(107)
<223> OTHER INFORMATION: Xaa = Glutamine or Glutamic Acid
<221> NAME/KEY: VARIANT
<222> LOCATION: (108)...(108)
<223> OTHER INFORMATION: Xaa = Glutamic Acid or Threonine
<221> NAME/KEY: VARIANT
<222> LOCATION: (110)...(110)
<223> OTHER INFORMATION: Xaa = Glutamic Acid or Alanine
<221> NAME/KEY: VARIANT
<222> LOCATION: (112)...(112)
<223> OTHER INFORMATION: Xaa = Alanine or Threonine
<221> NAME/KEY: VARIANT
<222> LOCATION: (114)...(114)
<223> OTHER INFORMATION: Xaa = Alanine or Glutamic Acid
<221> NAME/KEY: VARIANT
<222> LOCATION: (115)...(115)
<223> OTHER INFORMATION: Xaa = Leucine or Valine
<221> NAME/KEY: VARIANT
<222> LOCATION: (117)...(117)
<223> OTHER INFORMATION: Xaa = Glycine or Lysine
<221> NAME/KEY: VARIANT
<222> LOCATION: (118)...(118)
<223> OTHER INFORMATION: Xaa = Threonine or Valine
<221> NAME/KEY: VARIANT
<222> LOCATION: (120)...(120)
<223> OTHER INFORMATION: Xaa = Alanine or Valine
<221> NAME/KEY: VARIANT
<222> LOCATION: (121)...(121)
<223> OTHER INFORMATION: Xaa = Proline or Serine
<221> NAME/KEY: VARIANT
<222> LOCATION: (124)...(124)
<223> OTHER INFORMATION: Xaa = Valine, Threonine or Alanine

<400> SEQUENCE: 51

Xaa Glu Glu Xaa Glu Val Xaa Leu Xaa Glu Xaa Thr Leu Ile Asp Leu
 1               5                  10                  15

Glu Gln Pro Val Ala Gln Val Pro Val Val Ala Glu Ala Glu Leu Pro
            20                  25                  30

Gly Val Glu Ala Ala Glu Ala Ile Val Pro Ser Leu Glu Glu Asn Lys
        35                  40                  45

Leu Gln Glu Val Val Val Ala Pro Glu Ala Gln Gln Leu Glu Ser Ala
    50                  55                  60

Pro Glu Val Ser Ala Pro Xaa Gln Pro Glu Ser Thr Val Leu Gly Val
65                  70                  75                  80

Xaa Glu Gly Asp Leu Lys Ser Glu Val Ser Val Glu Ala Xaa Ala Xaa
                85                  90                  95

Xaa Xaa Gln Xaa Xaa Xaa Ile Ser Xaa Xaa Gln Glu Xaa Xaa Xaa Xaa
            100                 105                 110

Glu Xaa Xaa Glu Xaa Xaa Glu Xaa Xaa Val Glu Xaa Xaa
        115                 120                 125


<210> SEQ ID NO 52
<211> LENGTH: 253
<212> TYPE: PRT
<213> ORGANISM: Ehrlichia sp.

<400> SEQUENCE: 52

Ala Val Lys Ile Thr Asn Ser Thr Ile Asp Gly Lys Val Cys Asn Gly
 1               5                  10                  15

Ser Arg Glu Lys Gly Asn Ser Ala Gly Asn Asn Asn Ser Ala Val Ala
            20                  25                  30

Thr Tyr Ala Gln Thr His Thr Ala Asn Thr Ser Thr Ser Gln Cys Ser
        35                  40                  45

Gly Leu Gly Thr Thr Val Val Lys Gln Gly Tyr Gly Ser Leu Asn Lys
    50                  55                  60
```

-continued

```
Phe Val Ser Leu Thr Gly Val Gly Glu Gly Lys Asn Trp Pro Thr Gly
65                  70                  75                  80

Lys Ile His Asp Gly Ser Ser Gly Val Lys Asp Gly Glu Gln Asn Gly
                85                  90                  95

Asn Ala Lys Ala Val Ala Lys Asp Leu Val Asp Leu Asn Arg Asp Glu
            100                 105                 110

Lys Thr Ile Val Ala Gly Leu Leu Ala Lys Thr Ile Glu Gly Gly Glu
        115                 120                 125

Val Val Glu Ile Arg Ala Val Ser Ser Thr Ser Val Met Val Asn Ala
    130                 135                 140

Cys Tyr Asp Leu Leu Ser Glu Gly Leu Gly Val Val Pro Tyr Ala Cys
145                 150                 155                 160

Val Gly Leu Gly Gly Asn Phe Val Gly Val Val Asp Gly His Ile Thr
                165                 170                 175

Pro Lys Leu Ala Tyr Arg Leu Lys Ala Gly Leu Ser Tyr Gln Leu Ser
            180                 185                 190

Pro Glu Ile Ser Ala Phe Ala Gly Gly Phe Tyr His Arg Val Val Gly
        195                 200                 205

Asp Gly Val Tyr Asp Asp Leu Pro Ala Gln Arg Leu Val Asp Asp Thr
    210                 215                 220

Ser Pro Ala Gly Arg Thr Lys Asp Thr Ala Val Ala Asn Phe Ser Met
225                 230                 235                 240

Ala Tyr Val Gly Gly Glu Phe Gly Val Arg Phe Ala Phe
                245                 250
```

<210> SEQ ID NO 53
<211> LENGTH: 366
<212> TYPE: PRT
<213> ORGANISM: Ehrlichia sp.

<400> SEQUENCE: 53

```
Tyr Met Arg Ser Arg Ser Lys Leu Leu Leu Gly Ser Val Met Met Ser
 1               5                  10                  15

Met Ala Ile Val Met Ala Gly Asn Asp Val Arg Ala His Asp Asp Val
            20                  25                  30

Ser Ala Leu Glu Thr Gly Gly Ala Gly Tyr Phe Tyr Val Gly Leu Asp
        35                  40                  45

Tyr Ser Pro Ala Phe Ser Lys Ile Arg Asp Phe Ser Ile Arg Glu Ser
    50                  55                  60

Asn Gly Glu Thr Lys Ala Val Tyr Pro Tyr Leu Lys Asp Gly Lys Ser
65                  70                  75                  80

Val Lys Leu Glu Ser His Lys Phe Asp Trp Asn Thr Pro Asp Pro Arg
                85                  90                  95

Ile Gly Phe Lys Asp Asn Met Leu Val Ala Met Glu Gly Ser Val Gly
            100                 105                 110

Tyr Gly Ile Gly Gly Ala Arg Val Glu Leu Glu Ile Gly Tyr Glu Arg
        115                 120                 125

Phe Lys Thr Lys Gly Ile Arg Asp Ser Gly Ser Lys Glu Asp Glu Ala
    130                 135                 140

Asp Thr Val Tyr Leu Leu Ala Lys Glu Leu Ala Tyr Asp Val Val Thr
145                 150                 155                 160

Gly Gln Thr Asp Asn Leu Ala Ala Ala Leu Ala Lys Thr Ser Gly Lys
                165                 170                 175

Asp Ile Val Gln Phe Ala Asn Ala Val Lys Ile Thr Asn Ser Ala Ile
```

-continued

```
            180                 185                 190

Asp Gly Lys Ile Cys Asn Arg Gly Lys Ala Ser Gly Gly Ser Lys Gly
        195                 200                 205

Leu Ser Ser Ser Lys Ala Gly Ser Cys Asp Ser Ile Asp Lys Gln Ser
    210                 215                 220

Gly Ser Leu Glu Gln Ser Leu Thr Ala Ala Leu Gly Asp Lys Gly Ala
225                 230                 235                 240

Glu Lys Trp Pro Lys Ile Asn Asn Gly Thr Ser Asp Thr Thr Leu Asn
                245                 250                 255

Gly Asn Asp Thr Ser Ser Thr Pro Tyr Thr Lys Asp Ala Ser Ala Thr
            260                 265                 270

Val Ala Lys Asp Leu Val Ala Leu Asn His Asp Glu Lys Thr Ile Val
        275                 280                 285

Ala Gly Leu Leu Ala Lys Thr Ile Glu Gly Gly Glu Val Val Glu Ile
    290                 295                 300

Arg Ala Val Ser Ser Thr Ser Val Met Val Asn Ala Cys Tyr Asp Leu
305                 310                 315                 320

Leu Ser Glu Gly Leu Gly Val Val Pro Tyr Ala Cys Val Gly Leu Gly
                325                 330                 335

Gly Asn Phe Val Gly Val Val Asp Gly His Ile Thr Pro Lys Leu Ala
            340                 345                 350

Tyr Arg Leu Lys Ala Gly Leu Ser Tyr Gln Leu Ser Pro Glu
        355                 360                 365


<210> SEQ ID NO 54
<211> LENGTH: 340
<212> TYPE: PRT
<213> ORGANISM: Ehrlichia sp.

<400> SEQUENCE: 54

Arg Ser Asp Tyr Gln Gly Gln Val Leu Ala Ile Ile Arg Pro Gln Gly
 1               5                  10                  15

Glu Ala Thr Ala Glu Gly Val Asn Lys Glu Pro Glu Ser Lys Glu Glu
            20                  25                  30

Val Leu Ala Gln Pro Val Val Ala Gln Ala Val Ser Thr Gln Lys Pro
        35                  40                  45

Gln Glu Lys Thr Ile Ile Glu Gly Lys Gly Leu Val Thr Pro Thr Val
    50                  55                  60

Glu Asp Phe Val Ala Gly Ile Asn Thr Thr Pro Thr Ser Arg Ala Leu
65                  70                  75                  80

Gly Met Ser Ala Lys Ser Glu Gln Asp Lys Lys Ile Val Ala Ser Gln
                85                  90                  95

Pro Ser Lys Asp Leu Met Ser Cys His Gly Asp Val Val Gly Glu Arg
            100                 105                 110

Arg Val Lys Met Ser Lys Ile Arg Gln Val Ile Ala Ala Arg Leu Lys
        115                 120                 125

Glu Ser Gln Asn Thr Ser Ala Thr Leu Ser Thr Phe Asn Glu Val Asp
    130                 135                 140

Met Ser Lys Val Met Glu Leu Arg Ala Lys Tyr Lys Asp Ala Phe Val
145                 150                 155                 160

Lys Arg Tyr Asp Val Lys Leu Gly Phe Met Ser Phe Phe Ile Arg Ala
                165                 170                 175

Val Val Leu Val Leu Ser Glu Ile Pro Val Leu Asn Ala Glu Ile Ser
            180                 185                 190
```

-continued

```
Gly Asp Asp Ile Val Tyr Arg Asp Tyr Cys Asn Ile Gly Val Ala Val
        195                 200                 205

Gly Thr Asp Lys Gly Leu Val Val Pro Val Ile Arg Arg Ala Glu Thr
    210                 215                 220

Met Ser Leu Ala Glu Met Glu Gln Ala Leu Val Asp Leu Ser Thr Lys
225                 230                 235                 240

Ala Arg Ser Gly Lys Leu Ser Val Ser Asp Met Ser Gly Ala Thr Phe
                245                 250                 255

Thr Ile Thr Asn Gly Gly Val Tyr Gly Ser Leu Leu Ser Thr Pro Ile
            260                 265                 270

Ile Asn Pro Pro Gln Ser Gly Ile Leu Gly Met His Ala Ile Gln Gln
        275                 280                 285

Arg Pro Val Ala Val Asp Gly Lys Val Glu Ile Arg Pro Met Met Tyr
    290                 295                 300

Leu Ala Leu Ser Tyr Asp His Arg Ile Val Asp Gly Gln Gly Ala Val
305                 310                 315                 320

Thr Phe Leu Val Arg Val Lys Gln Tyr Ile Glu Asp Pro Asn Arg Leu
                325                 330                 335

Ala Leu Gly Ile
            340


<210> SEQ ID NO 55
<211> LENGTH: 177
<212> TYPE: PRT
<213> ORGANISM: Ehrlichia sp.

<400> SEQUENCE: 55

Gly Val Phe Met Gly Arg Gly Thr Ile Thr Ile His Ser Lys Glu Asp
 1               5                  10                  15

Phe Ala Cys Met Arg Arg Ala Gly Met Leu Ala Ala Lys Val Leu Asp
            20                  25                  30

Phe Ile Thr Pro His Val Val Pro Gly Val Thr Thr Asn Ala Leu Asn
        35                  40                  45

Asp Leu Cys His Asp Phe Ile Ile Ser Ala Gly Ala Ile Pro Ala Pro
    50                  55                  60

Leu Gly Tyr Arg Gly Tyr Pro Lys Ser Ile Cys Thr Ser Lys Asn Phe
65                  70                  75                  80

Val Val Cys His Gly Ile Pro Asp Asp Ile Ala Leu Lys Asn Gly Asp
                85                  90                  95

Ile Val Asn Ile Asp Val Thr Val Ile Leu Asp Gly Trp His Gly Asp
            100                 105                 110

Thr Asn Arg Met Tyr Trp Val Gly Asp Asn Val Ser Ile Lys Ala Lys
        115                 120                 125

Arg Ile Cys Glu Ala Ser Tyr Lys Ala Leu Met Ala Ala Ile Gly Val
    130                 135                 140

Ile Gln Pro Gly Lys Lys Leu Asn Ser Ile Gly Leu Ala Ile Glu Glu
145                 150                 155                 160

Glu Ile Arg Gly Tyr Gly Tyr Ser Ile Val Arg Asp Tyr Cys Gly His
                165                 170                 175

Gly


<210> SEQ ID NO 56
<211> LENGTH: 197
<212> TYPE: PRT
<213> ORGANISM: Ehrlichia sp.
```

<400> SEQUENCE: 56

```
Glu Trp Trp Cys Thr Pro Leu Trp Cys Ala Lys Asn Thr Ile Met Leu
 1               5                  10                  15

Cys Arg Leu Lys Asn Thr Gly Gly Cys Glu Val Met Arg Glu Val Leu
            20                  25                  30

Val Pro Tyr Ala Gly Val Ser Pro Ser Val Asp Ser Thr Ala Phe Ile
        35                  40                  45

Ala Gly Tyr Ala Arg Ile Ile Gly Asp Val Cys Ile Gly Lys Asn Ala
    50                  55                  60

Ser Ile Trp Tyr Gly Thr Val Leu Arg Gly Asp Val Asp Lys Ile Glu
65                  70                  75                  80

Val Gly Glu Gly Thr Asn Ile Gln Asp Asn Thr Val Val His Thr Asp
                85                  90                  95

Ser Met His Gly Asp Thr Val Ile Gly Lys Phe Val Thr Ile Gly His
            100                 105                 110

Ser Cys Ile Leu His Ala Cys Thr Leu Gly Asn Asn Ala Phe Val Gly
        115                 120                 125

Met Gly Ser Ile Val Met Asp Arg Ala Val Met Glu Glu Gly Ser Met
    130                 135                 140

Leu Ala Ala Gly Ser Leu Leu Thr Arg Gly Lys Ile Val Lys Ser Gly
145                 150                 155                 160

Glu Leu Trp Ala Gly Arg Pro Ala Lys Phe Leu Arg Met Met Thr Glu
                165                 170                 175

Glu Glu Ile Leu Tyr Leu Gln Lys Ser Ala Glu Asn Tyr Ile Ala Leu
            180                 185                 190

Ser Arg Gly Tyr Leu
        195
```

<210> SEQ ID NO 57
<211> LENGTH: 172
<212> TYPE: PRT
<213> ORGANISM: Ehrlichia sp.

<400> SEQUENCE: 57

```
Ala Asn Leu Ala Arg Ala Thr Ala Pro Ser Met Phe Ser Phe Ser Leu
 1               5                  10                  15

Lys Gly Arg Pro Ser Phe Phe Glu Ile Ala Phe Ser Leu Gly Ser Val
            20                  25                  30

Met Met Ser Met Ala Ile Val Met Ala Gly Asn Asp Val Arg Ala His
        35                  40                  45

Asp Asp Val Ser Ala Leu Glu Thr Gly Gly Ala Gly Tyr Phe Tyr Val
    50                  55                  60

Gly Leu Asp Tyr Ser Pro Ala Phe Ser Lys Ile Arg Asp Phe Ser Ile
65                  70                  75                  80

Arg Glu Ser Asn Gly Glu Thr Lys Ala Val Tyr Pro Tyr Leu Lys Asp
                85                  90                  95

Gly Lys Ser Val Lys Leu Glu Ser Asn Lys Phe Asp Trp Asn Thr Pro
            100                 105                 110

Asp Pro Arg Ile Gly Phe Lys Asp Asn Met Leu Val Ala Met Glu Gly
        115                 120                 125

Ser Val Gly Tyr Gly Ile Gly Gly Ala Arg Val Glu Leu Glu Ile Gly
    130                 135                 140

Tyr Glu Arg Phe Lys Thr Lys Gly Ile Arg Asp Ser Gly Ser Lys Glu
145                 150                 155                 160
```

```
Asp Glu Ala Asp Thr Val Tyr Leu Leu Ala Lys Glu
                165                 170


<210> SEQ ID NO 58
<211> LENGTH: 196
<212> TYPE: PRT
<213> ORGANISM: Ehrlichia sp.

<400> SEQUENCE: 58

Lys Leu Lys Glu Asp Val Ala Ser Met Ser Asp Glu Ala Leu Leu Lys
 1               5                  10                  15

Phe Ala Asn Arg Leu Arg Arg Gly Val Pro Met Ala Ala Pro Val Phe
            20                  25                  30

Glu Gly Pro Lys Asp Ala Gln Ile Ser Arg Leu Leu Glu Leu Ala Asp
        35                  40                  45

Val Asp Pro Ser Gly Gln Val Asp Leu Tyr Asp Gly Arg Ser Gly Gln
    50                  55                  60

Lys Phe Asp Arg Lys Val Thr Val Gly Tyr Ile Tyr Met Leu Lys Leu
65                  70                  75                  80

His His Leu Val Asp Asp Lys Ile His Ala Arg Ser Val Gly Pro Tyr
                85                  90                  95

Gly Leu Val Thr Gln Gln Pro Leu Gly Gly Lys Ser His Phe Gly Gly
            100                 105                 110

Gln Arg Phe Gly Glu Met Glu Cys Trp Ala Leu Gln Ala Tyr Gly Ala
        115                 120                 125

Ala Tyr Thr Leu Gln Glu Met Leu Thr Val Lys Ser Asp Asp Ile Val
    130                 135                 140

Gly Arg Val Thr Ile Tyr Glu Ser Ile Ile Lys Gly Asp Ser Asn Phe
145                 150                 155                 160

Glu Cys Gly Ile Pro Glu Ser Phe Asn Val Met Val Lys Glu Leu Arg
                165                 170                 175

Ser Leu Cys Leu Asp Val Val Leu Lys Gln Asp Lys Glu Phe Thr Ser
            180                 185                 190

Ser Lys Val Glu
        195


<210> SEQ ID NO 59
<211> LENGTH: 719
<212> TYPE: PRT
<213> ORGANISM: Ehrlichia sp.

<400> SEQUENCE: 59

Gly Phe Thr Ile Met Lys Thr Leu Asp Leu Tyr Gly Tyr Thr Ser Ile
 1               5                  10                  15

Ala Gln Ser Phe Asp Asn Ile Cys Ile Ser Ile Ser Ser Pro Gln Ser
            20                  25                  30

Ile Arg Ala Met Ser Tyr Gly Glu Ile Lys Asp Ile Ser Thr Thr Ile
        35                  40                  45

Tyr Arg Thr Phe Lys Val Glu Lys Gly Gly Leu Phe Cys Pro Lys Ile
    50                  55                  60

Phe Gly Pro Val Asn Asp Asp Glu Cys Leu Cys Gly Lys Tyr Arg Lys
65                  70                  75                  80

Lys Arg Tyr Arg Gly Ile Val Cys Glu Lys Cys Gly Val Glu Val Thr
                85                  90                  95

Ser Ser Lys Val Arg Arg Glu Arg Met Gly His Ile Glu Leu Val Ser
            100                 105                 110
```

-continued

```
Pro Val Ala His Ile Trp Phe Leu Lys Ser Leu Pro Ser Arg Ile Gly
        115                 120                 125

Ala Leu Leu Asp Met Pro Leu Lys Ala Ile Glu Asn Ile Leu Tyr Ser
    130                 135                 140

Gly Asp Phe Val Val Ile Asp Pro Val Ala Thr Pro Phe Ala Lys Gly
145                 150                 155                 160

Glu Val Ile Ser Glu Val Val Tyr Asn Gln Ala Arg Asp Ala Tyr Gly
                165                 170                 175

Glu Asp Gly Phe Phe Ala Leu Thr Gly Val Glu Ala Ile Lys Glu Leu
            180                 185                 190

Leu Thr Arg Leu Asp Leu Glu Ala Ile Arg Ala Thr Leu Arg Asn Glu
        195                 200                 205

Leu Glu Ser Thr Ser Ser Glu Met Lys Arg Lys Lys Val Val Lys Arg
    210                 215                 220

Leu Arg Leu Val Glu Asn Phe Ile Lys Ser Gly Asn Arg Pro Glu Trp
225                 230                 235                 240

Met Ile Leu Thr Val Ile Pro Val Leu Pro Pro Asp Leu Arg Pro Leu
                245                 250                 255

Val Ser Leu Glu Asn Gly Arg Pro Ala Val Ser Asp Leu Asn His His
            260                 265                 270

Tyr Arg Thr Ile Ile Asn Arg Asn Asn Arg Leu Glu Lys Leu Leu Lys
        275                 280                 285

Leu Asn Pro Pro Ala Ile Met Ile Arg Asn Glu Lys Arg Met Leu Gln
    290                 295                 300

Glu Ala Val Asp Ala Leu Phe Asp Ser Ser Arg Arg Ser Tyr Val Ser
305                 310                 315                 320

Ser Arg Val Gly Ser Met Gly Tyr Lys Lys Ser Leu Ser Asp Met Leu
                325                 330                 335

Lys Gly Lys Gln Gly Arg Phe Arg Gln Asn Leu Leu Gly Lys Arg Val
            340                 345                 350

Asp Tyr Ser Gly Arg Ser Val Ile Val Val Gly Pro Ser Leu Lys Leu
        355                 360                 365

His Gln Cys Gly Leu Pro Lys Lys Met Ala Leu Glu Leu Phe Lys Pro
    370                 375                 380

Phe Ile Cys Ser Lys Leu Lys Met Tyr Gly Ile Ala Pro Thr Val Lys
385                 390                 395                 400

Leu Ala Asn Lys Met Ile Gln Ser Glu Lys Pro Asp Val Trp Asp Val
                405                 410                 415

Leu Asp Glu Val Ile Lys Glu His Pro Ile Leu Leu Asn Arg Ala Pro
            420                 425                 430

Thr Leu His Arg Leu Gly Leu Gln Ala Phe Asp Pro Val Leu Ile Glu
        435                 440                 445

Gly Lys Ala Ile Gln Leu His Pro Leu Val Cys Ser Ala Phe Asn Ala
    450                 455                 460

Asp Phe Asp Gly Asp Gln Met Ala Val His Val Pro Leu Ser Gln Glu
465                 470                 475                 480

Ala Gln Leu Glu Ala Arg Val Leu Met Met Ser Thr Asn Asn Ile Leu
                485                 490                 495

Ser Pro Ser Asn Gly Arg Pro Ile Ile Val Pro Ser Lys Asp Ile Val
            500                 505                 510

Leu Gly Ile Tyr Tyr Leu Thr Leu Leu Glu Glu Asp Pro Glu Val Arg
        515                 520                 525

Glu Val Gln Thr Phe Ala Glu Phe Ser His Val Glu Tyr Ala Leu His
```

-continued

```
    530                 535                 540

Glu Gly Ile Val His Thr Cys Ser Arg Ile Lys Tyr Arg Met Gln Lys
545                 550                 555                 560

Ser Ala Ala Asp Gly Thr Val Ser Ser Glu Ile Val Glu Thr Thr Pro
                565                 570                 575

Gly Arg Leu Ile Leu Trp Gln Ile Phe Pro Gln His Lys Asp Leu Thr
            580                 585                 590

Phe Asp Leu Ile Asn Gln Val Leu Thr Val Lys Glu Ile Thr Ser Ile
        595                 600                 605

Val Asp Leu Val Tyr Arg Ser Cys Gly Gln Arg Glu Thr Val Glu Phe
    610                 615                 620

Ser Asp Lys Leu Met Tyr Trp Gly Phe Lys Tyr Ala Ser Gln Ser Gly
625                 630                 635                 640

Ile Ser Phe Gly Cys Lys Asp Met Ile Ile Pro Asp Thr Lys Ala Ala
                645                 650                 655

His Val Glu Asp Ala Ser Glu Lys Ile Arg Glu Phe Ser Ile Gln Tyr
            660                 665                 670

Gln Asp Gly Leu Ile Thr Lys Ser Glu Arg Tyr Asn Lys Val Val Asp
        675                 680                 685

Glu Trp Ser Lys Cys Thr Asp Leu Ile Ala Arg Asp Met Met Lys Ala
    690                 695                 700

Ile Ser Leu Cys Asp Glu Pro Ala Arg Ser Gly Ala Pro Asp Thr
705                 710                 715


<210> SEQ ID NO 60
<211> LENGTH: 439
<212> TYPE: PRT
<213> ORGANISM: Ehrlichia sp.

<400> SEQUENCE: 60

Ile His Ser Ala Tyr Asn Met Leu His Asp Cys Ala Thr Ala Gln Cys
 1               5                  10                  15

Asn Lys Glu Val Pro Arg Phe Met Asp Pro Asp Phe Thr Arg Arg Glu
            20                  25                  30

Val His Leu Gln Ile Ala Lys Val Cys Ala Ile Leu Val Asn Ala Ile
        35                  40                  45

Thr Met Ala Ser Cys Phe Val Thr Thr Leu Thr Glu Ala Ser Asp Ser
    50                  55                  60

Ala Ile Gly Glu Ala Asp Glu His Ser Ala Tyr His Ala Asn Met Ala
65                  70                  75                  80

Leu Ser Ala Tyr Val Asn Ala Lys Phe Ser Ala Leu Ser Arg Cys Leu
                85                  90                  95

Asn Tyr Ser Pro Gly Pro Glu Glu Thr Lys Arg Arg Lys Ala Ile Leu
            100                 105                 110

Arg Val Val Arg His Asn Ile Glu Leu Cys Asn Lys Val Ala Glu Leu
        115                 120                 125

Val Asp Pro Glu Ile Pro Tyr Cys Phe Arg Asp Arg Thr Val Ser Cys
    130                 135                 140

Leu Asn Ser Met Leu Asp Ala Val Gly Ser Thr Ser Ala Glu Cys Glu
145                 150                 155                 160

Glu Met Val Ser Asp Asn Asp Ser Ala Lys Asn Arg Leu Ala Leu Ala
                165                 170                 175

Lys Lys Ala Arg Thr Gly Phe Leu His His Phe Lys Thr Tyr Lys Ser
            180                 185                 190
```

-continued

```
Leu Gly Leu Ser Val Ala Phe Lys Ser Phe Arg His Asp Lys Tyr Val
        195                 200                 205

Gln Ala Leu Val Tyr Ala Ile Gly Ser Leu Phe Ser Met His Arg Val
    210                 215                 220

Tyr Ala Ser Thr Gly Asn Thr Gly His Val Val Ala Ser Lys Ile Glu
225                 230                 235                 240

His Cys Leu Gln Met Leu Leu Thr Leu Tyr Lys Tyr Lys Val Arg Arg
                245                 250                 255

Ala Gly Ala Ser Glu Tyr Thr Ala Gln Glu Leu Tyr Leu Asp Met Cys
            260                 265                 270

Thr Val Tyr Asp Glu Ile Gln Glu Cys Val Thr Arg Gly Leu Leu Leu
        275                 280                 285

Asn Pro Gln Thr Glu Val Gly Phe Cys Ser Ala Met Leu Gly Tyr Leu
    290                 295                 300

Ser Ala Met Ile Gly Ile Trp Glu Lys Lys Tyr Glu Arg Tyr Phe Asn
305                 310                 315                 320

Asn Ile Arg Gln Thr Glu Gly Ser Pro Ser Gln Pro Ser Thr Ser Arg
                325                 330                 335

Leu Gly Ser Ala Gly Ala Gly Ile Gly Gly Ser Gln Ala Ser Tyr Thr
            340                 345                 350

Leu Pro His Asp Pro Gly His Met Pro Ser Ser Pro Ser Gln Pro Ser
        355                 360                 365

Thr Ser Gly Leu Gly Gly Asn Pro Ala Gly Gln Gly Ala Leu Gln Ala
    370                 375                 380

Gln Ala Pro Cys Gly Pro Leu Gln Asp Tyr Ser Tyr Ala Gln Pro Ser
385                 390                 395                 400

Thr Ser Gly Leu Gly Gly Ala Ser Ser Thr Leu Glu Gly Ala Gln Val
                405                 410                 415

Val Ser Pro Arg Ser Gln Thr Pro Ser Asp Asp Glu Leu Glu Pro Pro
            420                 425                 430

Ser Arg Arg Ser Arg Ser Ala
        435


<210> SEQ ID NO 61
<211> LENGTH: 752
<212> TYPE: PRT
<213> ORGANISM: Ehrlichia sp.

<400> SEQUENCE: 61

Met His Met Pro Arg Ile Phe Thr Thr Pro Val Met Ser Gly Tyr Ala
 1               5                  10                  15

Tyr Ser Gly Cys Ser Ser Ala Glu Tyr Lys Glu Thr Val Cys Asn Ser
            20                  25                  30

Ile Met Thr Asn Ser Arg Pro Tyr Ala Ala Cys Leu Gln Ala Ile Arg
        35                  40                  45

Gln Cys Met Leu Glu Leu Arg Asp Thr Phe Val Lys Leu Arg Gly Val
    50                  55                  60

Asp Val Val Phe Ala Ala Ala Asp Lys Ile Asp Ser Ile Asn Ser Cys
65                  70                  75                  80

Ile Thr Ala Ala Glu Gly Ala Ser Ser Ala Glu Pro Gly Val Leu Tyr
                85                  90                  95

Ser Leu Ile Asn Arg Leu Tyr Asp Ala Leu Gln Asp Cys Ile Thr Ala
            100                 105                 110

Gln Cys Asn Lys Glu Val Pro Leu Phe Met Asp Gln Asp Phe Ile Lys
        115                 120                 125
```

-continued

```
Arg Lys Ala His Leu Gln Ile Gly Lys Ala Cys Ala Ile Ile Val Asn
    130                 135                 140

Val Ile Ala Ile Val Asn Cys Cys Ala Arg Thr Ile Ala Thr Arg Phe
145                 150                 155                 160

Thr Gly Ala Val Ser Ser Glu Arg Arg Asp Gly Ser Ala Ser His Thr
                165                 170                 175

Val Thr Ala Leu Ser Ala Tyr Cys Tyr Val Lys Phe Ser Ala Leu Ser
            180                 185                 190

Arg Cys Leu Asn Ser Ser Leu Asp Ser Glu Glu Thr Glu Asn Ile Lys
        195                 200                 205

Ala Ile Leu Arg Val Val Arg His Asn Ile Glu Leu Cys Ser Lys Val
    210                 215                 220

Ala Glu Leu Val Glu Pro Asn Thr Pro Arg Phe Phe Arg His Arg Thr
225                 230                 235                 240

Glu Ala Cys Leu Asp Ser Val Ile Asp Ala Ile Glu Thr Ser Ala Ala
                245                 250                 255

Ala Cys Glu Ala Met Val Arg Asn Asn Glu Ser Ala Arg Leu Arg Leu
            260                 265                 270

Gly Leu Ser Arg Arg Ala Met Ala Asn Phe Leu Tyr Tyr Leu Glu Ala
        275                 280                 285

Tyr Val Glu Gly Leu Gly Val His Ser Phe Asp Leu Arg Leu Lys Arg
    290                 295                 300

Glu Arg Tyr Arg Gly Gly Ala Leu Val His Ala Val Gly Gly Leu Phe
305                 310                 315                 320

Leu Met Tyr Arg Val Tyr Ala Ser Thr Gly Asn Val Asp His Val Val
                325                 330                 335

Ala Gly Arg Ile Gly His Cys Leu Gln Ile Leu Cys Ala Leu Tyr Ser
            340                 345                 350

Arg Arg Arg Glu Leu Gly Ala Tyr Arg Ala Arg Lys Ser Phe Leu Asp
        355                 360                 365

Met Cys His Val Tyr Glu Glu Ile Asn Glu His Ile Thr Glu Asp Ala
    370                 375                 380

Leu Leu Ile Pro Gln Ile Glu Val Lys Trp Arg Asn Thr Ala Leu Arg
385                 390                 395                 400

Tyr Leu Ser Val Met Met Asn Ile Cys Asp Lys Lys Tyr Gly Arg Tyr
                405                 410                 415

Phe Asn Ala Val Glu Gln Thr Gly Ala Ala Pro Ser Gln Pro Ser Thr
            420                 425                 430

Ser Gly Leu Gly Ser Thr Ser Ala Gly Val Glu Gly Ala Gln Ala Ile
        435                 440                 445

Ser Val Pro Leu Arg Val Leu Glu Arg Ile Pro Ile Pro Tyr Gly Ala
    450                 455                 460

Pro Trp Asp Gln Pro Ser Thr Ser Gly Met Gly Gly Thr Ala Gly Thr
465                 470                 475                 480

Gly Ser Gln Gln Ala Ser His Ile Pro Pro His Asp Pro Gly Met Met
                485                 490                 495

Pro Tyr Ser Tyr Ala Gln Pro Ser Thr Leu Trp Asp Gln Pro Ser Thr
            500                 505                 510

Ser Gly Leu Gly Ser Ala Ala Gly Thr Gly Ser Gln Gln Ala Ser His
        515                 520                 525

Ile Pro Pro His Asp Pro Gly Met Met Pro Tyr Ser Tyr Ala Gln Pro
    530                 535                 540
```

-continued

```
Ser Thr Ser Trp Asp Gln Pro Ser Thr Ser Gly Leu Gly Ser Ala Ala
545                 550                 555                 560

Gly Met Gly Ser Gln Gln Ala Ser His Ile Pro Pro His Asp Pro Gly
                565                 570                 575

Met Met Pro Tyr Ser Tyr Ala Gln Pro Ser Thr Ser Trp Asp Gln Pro
            580                 585                 590

Ser Thr Ser Gly Leu Gly Ser Ala Ala Gly Met Gly Ser Gln Gln Ala
        595                 600                 605

Ser His Ile Pro Pro His Asp Pro Gly Met Met Pro Tyr Ser Tyr Ala
    610                 615                 620

Gln Pro Ser Thr Ser Trp Asp Gln Pro Ser Thr Ser Trp Asp Gln Pro
625                 630                 635                 640

Ser Thr Ser Gly Leu Gly Gly Thr Ala Gly Gln Gly Ala Gln Leu Val
                645                 650                 655

Pro Pro Pro Pro His Ile Ile Leu Arg Val Leu Glu Asn Val Pro Tyr
            660                 665                 670

Pro Ser Ser Gln Phe Ser Thr Ser Gly Leu Gly Gly Thr Ser Thr Gly
        675                 680                 685

Met Gly Arg Ser Gln Ala Pro Tyr Val Pro Pro Gln Asp Gln Gly Ile
    690                 695                 700

Met Pro Tyr Ser Trp Asp Gln Pro Ser Ala Ser Gly Leu Gly Gly Ala
705                 710                 715                 720

Ser Tyr Thr Leu Glu Glu Ala Gln Val Ser Ser His Arg Pro Arg Thr
                725                 730                 735

Pro Ser Asp Asp Asp Ser Glu Pro Pro Ser Lys Gln Ala Arg Arg Ala
            740                 745                 750


<210> SEQ ID NO 62
<211> LENGTH: 110
<212> TYPE: PRT
<213> ORGANISM: Ehrlichia sp.

<400> SEQUENCE: 62

Met Tyr Thr Val Ser Asp Ser Glu Ser Ile Thr Ser Phe Val Thr Pro
 1               5                  10                  15

Pro Met Leu Met Ala Asn Ile Ser Ser Thr Lys Arg Ser Gly Tyr Leu
            20                  25                  30

Leu Ser Leu Ser Val Glu Pro Ser Asp Phe Phe Thr Val Thr Phe Phe
        35                  40                  45

Leu Lys Glu Thr Pro Phe Thr Thr Asp Asn Ser Val Pro Phe Cys Ser
    50                  55                  60

Phe Glu Arg Asn Ser Thr Ala Asn Ser Arg Ile Phe Phe Ile Arg Asn
65                  70                  75                  80

Ala Leu Phe His Ser Ser Val Arg Ile Asp Leu Leu Ser Ser Ser Val
                85                  90                  95

Leu Gly Leu Gly Gly Thr Thr Ser Val Thr Arg Thr Pro Lys
            100                 105                 110


<210> SEQ ID NO 63
<211> LENGTH: 149
<212> TYPE: PRT
<213> ORGANISM: Ehrlichia sp.

<400> SEQUENCE: 63

Asp Gly Phe Pro Thr Ala Asp Glu Asn Ala Lys Val Val Lys Ala Phe
 1               5                  10                  15
```

-continued

```
Ile Pro Ser Cys Asn Gly Lys Ser Phe Thr Lys Leu Pro Asp Leu Ser
            20                  25                  30

Ser Pro Cys Ile Ser Lys Phe Val Lys Thr Pro Leu Ile Arg Ala Pro
        35                  40                  45

Asn Ile Ser Phe Ser Ser Phe Ser Asn Ala Pro Arg Leu Ile Ile Ser
    50                  55                  60

Phe Ala Phe Phe Thr Leu Leu Thr Ser Asn Ser Pro Ala Phe Cys Leu
65                  70                  75                  80

Leu Ile Phe Glu Asp Ile Phe Ser Phe Ser Phe Ser Arg Ser Ser Leu
                85                  90                  95

Val Ile Ser Cys Phe Leu Ile Thr Phe Met Ile Cys Gln Pro Thr Thr
            100                 105                 110

Leu Arg Asn Ile Ser Leu Thr Ser Pro Ser Phe Ser Ala Asn Thr Thr
        115                 120                 125

Phe Arg Thr Pro Thr Gly Arg Thr Ser Leu Glu Ile Leu Leu Ser Ala
    130                 135                 140

Ile Ser Ser Met Val
145


<210> SEQ ID NO 64
<211> LENGTH: 590
<212> TYPE: PRT
<213> ORGANISM: Ehrlichia sp.

<400> SEQUENCE: 64

Leu Leu Tyr Ser Phe Gly Asn Leu Thr Ser Tyr Gly Arg Ser Val Met
 1               5                  10                  15

Arg Ser Arg Lys Ile Tyr Val Trp Val Val Met Ala Thr Val Leu Gly
            20                  25                  30

Ala Met Ala Phe Val Thr Phe Gly Ser Met Ile Pro Met Gly Lys Leu
        35                  40                  45

Ser Asn Ser Gly Asn Gly Gln Cys Val Ala Met Leu Gly Asn Lys Cys
    50                  55                  60

Leu Pro Leu Arg Asp Tyr Arg Ile Met Tyr Arg Asn Glu Leu Ala Glu
65                  70                  75                  80

Leu Glu Lys Met Leu Gln His Lys Leu Ser Asp Ala Gln Ile Asn Gln
                85                  90                  95

Phe Gly Ile Lys Glu Val Val Leu Lys Asn Met Ile Ala Asp Met Val
            100                 105                 110

Val Glu Lys Phe Ala His Asp Leu Gly Ile Arg Val Gly Ser Asn Ser
        115                 120                 125

Leu Arg Ser Leu Ile Lys Asn Ile Arg Ile Phe Gln Asp Ala Asn Gly
    130                 135                 140

Val Phe Asp Gln Glu Arg Tyr Glu Ala Val Leu Ala Asp Ser Gly Met
145                 150                 155                 160

Thr Glu Ser Ser Tyr Val Asn Lys Ile Arg Asn Ala Leu Pro Ser Thr
                165                 170                 175

Ile Leu Met Glu Cys Leu Phe Pro Asn Arg Ala Glu Leu His Ile Pro
            180                 185                 190

Tyr Tyr Asp Ala Leu Ala Lys Asp Val Val Leu Gly Leu Leu Gln His
        195                 200                 205

Arg Val Ala Asp Ile Val Glu Ile Ser Ser Asp Ala Val Asp Ile Ser
    210                 215                 220

Gly Ser Asp Ile Ser Asp Asp Glu Leu Gln Lys Leu Phe Glu Glu Gln
225                 230                 235                 240
```

```
Tyr Lys Asn Ser Leu Asn Phe Pro Glu Tyr Arg Ser Ala Asp Tyr Ile
            245                 250                 255

Ile Met Ala Glu Asp Asp Leu Leu Ala Asp Val Ile Val Ser Asp Gln
        260                 265                 270

Glu Val Asp Val Glu Ile Lys Asn Ser Glu Leu His Asp Gln Arg Asp
    275                 280                 285

Val Leu Asn Leu Val Phe Thr Asp Lys Asn Glu Ala Glu Leu Ala Tyr
290                 295                 300

Lys Ala Tyr Gln Glu Gly Lys Ser Phe Glu Glu Leu Val Ser Asp Ala
305                 310                 315                 320

Gly Tyr Thr Ile Glu Asp Ile Ala Leu Asn Asn Ile Ser Lys Asp Val
            325                 330                 335

Leu Pro Val Gly Val Arg Asn Val Val Phe Ala Leu Asn Glu Gly Glu
        340                 345                 350

Val Ser Glu Met Phe Arg Ser Val Val Gly Trp His Ile Met Lys Val
    355                 360                 365

Ile Arg Lys His Glu Ile Thr Lys Glu Asp Leu Glu Lys Leu Lys Glu
    370                 375                 380

Lys Ile Ser Ser Asn Ile Arg Arg Gln Lys Ala Gly Glu Leu Leu Val
385                 390                 395                 400

Ser Asn Val Lys Lys Ala Asn Asp Met Ile Ser Arg Gly Ala Leu Leu
            405                 410                 415

Asn Glu Leu Lys Asp Met Phe Gly Ala Arg Ile Ser Gly Val Leu Thr
        420                 425                 430

Asn Phe Asp Met His Gly Leu Asp Lys Ser Gly Asn Leu Val Lys Asp
    435                 440                 445

Phe Pro Leu Gln Leu Gly Ile Asn Ala Phe Thr Thr Leu Ala Phe Ser
    450                 455                 460

Ser Ala Val Gly Lys Pro Ser His Leu Val Ser Asn Gly Asp Ala Tyr
465                 470                 475                 480

Phe Gly Val Leu Val Thr Glu Val Val Pro Pro Arg Pro Arg Thr Leu
            485                 490                 495

Glu Glu Ser Arg Ser Ile Leu Thr Glu Glu Trp Lys Ser Ala Leu Arg
        500                 505                 510

Met Lys Lys Ile Arg Glu Phe Ala Val Glu Leu Arg Ser Lys Leu Gln
    515                 520                 525

Asn Gly Thr Glu Leu Ser Val Val Asn Gly Val Ser Phe Lys Lys Asn
    530                 535                 540

Val Thr Val Lys Lys Ser Asp Gly Ser Thr Asp Asn Asp Ser Lys Tyr
545                 550                 555                 560

Pro Glu Arg Leu Val Asp Glu Ile Phe Ala Ile Asn Ile Gly Gly Val
            565                 570                 575

Thr Lys Glu Val Ile Asp Ser Glu Ser Glu Thr Val Tyr Ile
        580                 585                 590


<210> SEQ ID NO 65
<211> LENGTH: 245
<212> TYPE: PRT
<213> ORGANISM: Ehrlichia sp.

<400> SEQUENCE: 65

Gly Ser Cys Cys Tyr Glu Val Asp Gly Met Ala Lys Arg Phe Leu Asn
 1               5                  10                  15

Asp Thr Glu Lys Lys Leu Leu Ser Leu Leu Lys Ser Val Met Gln His
```

-continued

```
            20                  25                  30

Tyr Lys Pro Arg Thr Gly Phe Val Arg Ala Leu Leu Ser Ala Leu Arg
        35                  40                  45

Ser Ile Ser Val Gly Asn Pro Arg Gln Thr Ala His Asp Leu Ser Val
    50                  55                  60

Leu Val Thr Gln Asp Phe Leu Val Glu Val Ile Gly Ser Phe Ser Thr
65                  70                  75                  80

Gln Ala Ile Ala Pro Ser Phe Leu Asn Ile Met Ala Leu Val Asp Glu
                85                  90                  95

Glu Ala Leu Asn His Tyr Asp Arg Pro Gly Arg Ala Pro Met Phe Ala
            100                 105                 110

Asp Met Leu Arg Tyr Ala Gln Glu Gln Ile Arg Arg Gly Asn Leu Leu
        115                 120                 125

Gln His Arg Trp Asn Glu Glu Thr Phe Ala Ser Phe Ala Asp Ser Tyr
    130                 135                 140

Leu Arg Arg Arg His Glu Arg Val Ser Ala Glu His Leu Arg Gln Ala
145                 150                 155                 160

Met Gln Ile Leu His Ala Pro Ala Ser Tyr Arg Val Leu Ser Thr Asn
                165                 170                 175

Trp Phe Leu Leu Arg Leu Ile Ala Ala Gly Tyr Val Arg Asn Ala Val
            180                 185                 190

Asp Val Val Asp Ala Glu Ser Ala Gly Leu Thr Ser Pro Arg Ser Ser
        195                 200                 205

Ser Glu Arg Thr Ala Ile Glu Ser Leu Leu Lys Asp Tyr Asp Glu Glu
    210                 215                 220

Gly Leu Ser Glu Met Leu Glu Thr Glu Lys Gly Val Met Thr Ser Leu
225                 230                 235                 240

Phe Gly Thr Val Leu
                245


<210> SEQ ID NO 66
<211> LENGTH: 456
<212> TYPE: PRT
<213> ORGANISM: Ehrlichia sp.

<400> SEQUENCE: 66

Lys Ala Ile Pro Glu Ala Glu Lys Ile Phe Glu Lys Ala Met Asn Ile
 1               5                  10                  15

Ala Asp Lys Val Tyr Gly Ser Ala Ser Ser Glu Val Lys Ser Leu Phe
            20                  25                  30

Thr Cys Pro Asn Pro Glu Asp Ala Ser Thr Leu Val His Phe Val Ser
        35                  40                  45

Ser Asn Gly Thr Pro Asn Phe Asp Pro Leu Ala Lys Arg Val Leu Glu
    50                  55                  60

Glu Ala Tyr His Arg Tyr Gly Glu Glu Pro Phe Thr Asn Leu Asp Ile
65                  70                  75                  80

Ala Gly Asn Ala Pro Ile His Ala Ala Ala Gln Lys Ser Thr Val Gly
                85                  90                  95

Val Phe Glu Gln Val Val Arg Cys Thr Pro Glu Ser Val Val Asn Gln
            100                 105                 110

Leu Ala Pro Asn Gly Lys Ala Pro Ile His Met Ile Val Glu Asp Glu
        115                 120                 125

Pro Ser His Lys Gly Val Ser Val Lys Leu Gln Met Leu Ile Glu Asn
    130                 135                 140
```

-continued

```
Val Arg Asn Ile Pro Ser Ile Asn Val Pro Ser Pro Val Thr Gly Glu
145                 150                 155                 160

Thr Pro Val Val Ala Ala Tyr Lys Gly Gly Asn Thr Glu Gly Val Lys
                165                 170                 175

Thr Met Leu Arg Cys Asn Ser Met Asp Val Asp Ala Arg Ser His Asp
            180                 185                 190

Gly Gly Thr Ile Ile His Tyr Ala Ala Lys Asp Gly Asn Leu Glu Ile
        195                 200                 205

Leu Gln Gln Ala Leu Gly Arg Lys Ser Ser Tyr Ser Lys Phe Pro Val
    210                 215                 220

Lys Asp Gly Val Pro Thr Pro Gly Val Tyr Ala Ile Arg Glu Ala Ser
225                 230                 235                 240

Gly Gly Lys Val Ser Leu Pro Ala Leu Asp Met Leu Met Arg Tyr Glu
                245                 250                 255

Pro Tyr Pro Gln His Val Ala Val Glu Ala Val Arg Lys Gly Ala Ala
            260                 265                 270

Asp Val Leu Arg His Leu Ile Thr Thr Glu Val Ile Ser Val Asn Glu
        275                 280                 285

Glu Ile Thr Thr Pro Glu Gly Lys Lys Thr Thr Leu Thr Ala Glu Ala
    290                 295                 300

Leu Thr Ser Gly Gln Tyr Ala Ala Val Lys Thr Leu Ile Lys Asn Ser
305                 310                 315                 320

Ala Asp Val Asn Ala Ser Pro Glu Pro Ala Ile Ser Val Gly Ile Gln
                325                 330                 335

Gly Gly Cys Phe Gln Gly Gly Lys Ala Ile Lys His Leu Lys Arg Val
            340                 345                 350

Val Glu Ala Gly Ala His Ile Asn Thr Pro Thr Gly Ser Met Ser Pro
        355                 360                 365

Leu Ala Ala Ala Val Gln Val Ala Asn Glu Ala Ser Asn Leu Lys Glu
    370                 375                 380

Ala Asn Arg Ile Val Asn Phe Leu Leu Gln Arg Gly Ala Asp Leu Ser
385                 390                 395                 400

Ser Thr Asp His Thr Gly Thr Pro Ala Leu His Leu Ala Thr Ala Ala
                405                 410                 415

Gly Asn Gln Lys Thr Ala Arg Leu Leu Leu Asp Lys Gly Ala Pro Ala
            420                 425                 430

Thr Gln Arg Asp Ala Tyr Gly Lys Thr Ala Leu His Ile Ala Ala Ala
        435                 440                 445

Asn Gly Asp Gly Lys Leu Tyr Lys
    450                 455


<210> SEQ ID NO 67
<211> LENGTH: 113
<212> TYPE: PRT
<213> ORGANISM: Ehrlichia sp.

<400> SEQUENCE: 67

Asp Gly Asn Thr Pro Leu His Thr Ala Ala Ser Ser Val Gly Lys Asn
 1               5                  10                  15

Ala Leu Gly Asn Leu Asp Val Leu Cys Asp Lys Ala Leu Ile Ala Asp
            20                  25                  30

Val Asn Ala Lys Gly Pro Gly Gly Asn Thr Pro Leu His Ile Ala Thr
        35                  40                  45

Glu Arg Met Asp His Gln Lys Val Lys His Leu Leu Ser Arg Leu Ser
    50                  55                  60
```

-continued

```
Asp Ile Ser Val Ala Asn Asp Ala Gly Glu Thr Val Cys His Ile Val
65                  70                  75                  80

Ala Lys Gln Trp Pro Arg Arg Asp Val Leu Ser Tyr Ile Asp Lys Met
                85                  90                  95

Gln Glu Ala Val Ser Ser Asn Ile Glu Gly Asn Arg Ser Val Gln Arg
            100                 105                 110

His


<210> SEQ ID NO 68
<211> LENGTH: 623
<212> TYPE: PRT
<213> ORGANISM: Ehrlichia sp.

<400> SEQUENCE: 68

Asp Glu Ala Pro Met Thr Leu Leu Leu Lys Gln Asn Pro Ser Lys Ala
 1               5                  10                  15

Ser Val Ala Leu Leu Gly Ser Ala Ile Asp Phe Phe Leu Cys Arg Asp
            20                  25                  30

Arg Asn Ser His Pro Ala Arg Arg Arg Met Val Ile Leu Leu Ala Glu
        35                  40                  45

Gly Phe Thr Leu Arg Glu Gly Ser Ala Val Pro Pro Ala Leu Ile His
    50                  55                  60

Glu Asn Leu Thr Ser Pro Asp Leu Leu Ala Arg Ala Leu His Lys Thr
65                  70                  75                  80

Ala Ser Asn Ser Thr Ala Phe Gln Gln Val Pro Phe Gln Leu Trp His
                85                  90                  95

Ala Leu Ala Leu Ala Tyr Asn Ser Leu Pro Gly Lys Asn Gln Glu Glu
            100                 105                 110

Asp Leu Thr Asn Phe Val Leu Gly Cys Leu Asp Gly Val Ser Glu Asp
        115                 120                 125

Met Thr Ile Val Arg Glu Glu Asp Ser Thr Thr Phe Glu Val Gln Ser
    130                 135                 140

Tyr Thr Thr Phe Ser Arg Val His Ser Leu Leu Ala Ser Ala Pro Ser
145                 150                 155                 160

Ser Tyr Lys Asn Gly Ala Leu Thr Val His Glu Ser Cys Ile Phe Ser
                165                 170                 175

Ile Gln Asp Asn Ser Gly Val Pro Ile Ala Lys Val Lys Met Trp Val
            180                 185                 190

Glu Tyr Asp Ile Ala Pro Ser Thr Lys Ala Glu Gly Val Tyr Arg Thr
        195                 200                 205

Ala Val Lys Lys Val Lys Leu Val Leu Thr Glu Arg Asp Cys Arg Asp
    210                 215                 220

Val Arg Gln Gly Glu Pro Gly Ser Val Cys Ser Trp His Asn Ile Pro
225                 230                 235                 240

Lys Ala Leu Ala Lys His Tyr Val Arg Val Pro Glu Lys Pro Thr His
                245                 250                 255

Val Leu Tyr Ser Ala Cys Asn Leu Gln Arg His Asn Pro Arg Tyr Met
            260                 265                 270

Ala Arg Arg Val Phe Tyr Asp Val Ser Asp Ile Asp Glu Cys Ile Leu
        275                 280                 285

Arg Ala Tyr Ser Val Ile Ser Gly Met Pro Leu Glu Val Leu Glu Leu
    290                 295                 300

Ser Phe Cys Asn Thr Val Ile Ser Gln Glu Ala Ser Gly Val Phe Arg
305                 310                 315                 320
```

-continued

```
Val Val Val Arg Gly Val Val Gly Leu Val Gly Tyr Asp Lys Ser Ser
                325                 330                 335

Val Val Gln Gln Gly Ala Val Ser His Gly Arg Asp Ala Val Ser Lys
            340                 345                 350

Met Gly Val Cys Met Ser Phe Val Ala Ser Gln Ala His Asp Ala Cys
        355                 360                 365

Ala Thr Ile Leu Arg His Val Ala Val Thr Val Asn Thr Phe Gly Asn
    370                 375                 380

Val Leu Thr Leu Gly Gly Gly Ile Ser Leu Arg Asp Phe Leu Ala Gly
385                 390                 395                 400

Ser Ala Lys Asp Thr Asp Phe Ala Gly Gly His Ile Phe Asn Leu Ala
                405                 410                 415

Glu Glu Ile Val Ala His Gly Leu Ser Leu Trp Glu Asp Leu Gly Lys
            420                 425                 430

Arg His Arg Trp Ala Ser His Ser Val Pro Val Arg Gly Asp Cys Gly
        435                 440                 445

Ile Phe Ile Gln His Ser Asp Glu Ile Arg Glu Ile Leu Arg Ser Gln
    450                 455                 460

Pro Lys His Ala Ala Asn Ile Val Glu Lys Thr Gly Val Asn Thr Glu
465                 470                 475                 480

Asn Leu Arg Val Leu Leu Ser Ser Ile Leu Ser Asn Ser Ser Gly Ser
                485                 490                 495

Ser Leu Pro Val Glu Leu Ala Ala His Tyr Val Ala His Glu Gly Val
            500                 505                 510

Val Ala Asp Asn Gly Asp Ser Ala Arg Arg Leu Pro Val Asn Gln His
        515                 520                 525

Val Leu Glu Glu His Leu Val Tyr Arg Val Thr Ser Val Ser Gly Ile
    530                 535                 540

His Ile His Ala Cys Val Asp Tyr Val Val Glu Asp Ile Asp Thr Pro
545                 550                 555                 560

Gly Ser Val Lys Asp Leu Gly Leu Cys Ile Arg Asp Val Arg Ile Gly
                565                 570                 575

Thr Arg Val Ala Ser Ser Ala Glu Glu Val Cys Ser Ala Ile Gln Glu
            580                 585                 590

Lys Glu Gly Arg Ile Asp Arg Asn Asp Phe Ala Trp Phe Asn Val Asp
        595                 600                 605

Gln Ser Leu Val Glu Thr Ser Arg Ala Glu Phe Arg Ala Ala Ile
    610                 615                 620


<210> SEQ ID NO 69
<211> LENGTH: 464
<212> TYPE: PRT
<213> ORGANISM: Ehrlichia sp.

<400> SEQUENCE: 69

Arg Ile His Met Arg Lys Glu Asn Ser Lys Ala Ala Tyr Cys Val Thr
 1               5                  10                  15

Trp Arg Phe Lys Leu Arg Lys Lys Asn Thr His Asn Gly Ser Arg Arg
            20                  25                  30

Thr Val Ser Gly Ile Leu Asn Tyr Leu Arg Ala Leu Phe Phe Arg Ile
        35                  40                  45

Ile Ser Ile Phe Ser Thr Ser Ser Ser Ala Val Ser Lys Ala Glu Asp
    50                  55                  60

Glu Ala Asn Ser Val His Ile Cys Thr His Asn Ser Ser Asp Ala Ser
```

-continued

```
65                  70                  75                  80

Lys Asp Ser Lys Ala Lys His Lys Asp His Arg Pro Ser Ile Asp Val
                85                  90                  95

Ser Leu Lys Tyr Ser Gln Lys Lys Lys Trp Leu Glu Gly Ala Ser Gly
            100                 105                 110

Phe Ser Phe His Ser Ala Leu Cys Asp Ser Tyr Lys Asn Lys Ser Asn
        115                 120                 125

Leu Tyr Gly His Gln Phe Leu Ile Asp Met His Arg Cys Asp Trp Cys
    130                 135                 140

Ile Asn Lys Thr Phe Tyr Pro Arg Gln Asn Val Ser Ala His Ile Ala
145                 150                 155                 160

Arg Leu Glu Arg Ser Ile Lys Ser Ser Ser Ile Thr Asn Leu Asn Leu
                165                 170                 175

Val Cys Gln Arg Thr Tyr Gly Val Ser Arg Gly Val Phe Leu Arg Arg
            180                 185                 190

Tyr Arg Glu Arg Ser Leu Ala Ile Ala Met Leu Gln Lys Met Phe Arg
        195                 200                 205

Asp Asp Arg His Gly Val Val Pro Asp Ile Arg Leu Leu Asp Glu Ile
    210                 215                 220

Ala Ser His Cys His Gln Gly Gly Leu Ser Ala Trp Val Cys Phe Asp
225                 230                 235                 240

Val Ile Trp Pro Ile Lys His Ala Leu Asp Lys Glu Tyr Phe Phe Ser
                245                 250                 255

Asp Ala Gly Ala Thr Leu Asn Leu Leu Asn Arg Ile Tyr Val Ser Ala
            260                 265                 270

Cys Ser Asn Ile Lys Gln Val Asp Ala Ile Thr Pro Glu Arg Ile Ala
        275                 280                 285

Val Cys Glu Asn Leu Asp Phe Leu Leu Lys Val Pro Gln Ser Thr Glu
    290                 295                 300

Gly Glu Lys Thr Pro Ala Phe Lys Val Asn Thr Ala Leu Lys Tyr Glu
305                 310                 315                 320

Ile Ser Ile Gln Gly Glu Gly Arg Val Leu Tyr Asp Asn Cys Ser Leu
                325                 330                 335

Asn Leu Thr Ile Ile Thr Pro Pro Asp Cys Asn Ile Lys Thr Ser Pro
            340                 345                 350

Pro Leu Leu Phe Arg Val Cys Pro Pro Leu Gly Arg Leu Leu Leu Arg
        355                 360                 365

Leu Lys His Arg Phe Tyr Lys Arg Lys Val Phe Thr Pro Gln Asp Thr
    370                 375                 380

Arg Val Pro Asp Pro Thr Leu Val Arg Val Gln Arg Ile Pro Cys Ile
385                 390                 395                 400

Gly Met Asn Ile Thr Lys Leu Gln Tyr Ala Met Ala Pro Leu Pro Val
                405                 410                 415

Ser Pro Glu Glu Phe Phe Arg Asp Leu Val Lys Asn Ser Thr Ile Cys
            420                 425                 430

Gly Ile Tyr Ile Met Thr Ser Ser Leu Arg Lys Cys Ile Trp Gln Ser
        435                 440                 445

Leu Asn Pro Asn Met Leu Arg Leu Met Phe Leu Arg His Met Met Met
    450                 455                 460
```

<210> SEQ ID NO 70
<211> LENGTH: 378
<212> TYPE: PRT
<213> ORGANISM: Ehrlichia sp.

<400> SEQUENCE: 70

```
Ile Leu Arg Phe Ser Asp Asp Phe Pro Asp Ala Lys Val Ile Arg Leu
 1               5                  10                  15

Glu Cys Asn Tyr Arg Ser Thr Ser Asn Ile Leu Ala Ser Ala Ser Ala
            20                  25                  30

Ile Ile Asp Asn Asn Lys Ser Arg Leu Lys Lys Thr Leu Trp Thr His
        35                  40                  45

Asn Gln Ala Gly Gln Lys Val Gly Leu Met Lys Phe Phe Asp Gly Arg
    50                  55                  60

Leu Glu Ala Gln Tyr Ile Ser Glu His Ile Lys Ser Ser Tyr Asp Tyr
65                  70                  75                  80

Lys Phe Ser Glu Thr Ala Val Leu Val Arg Ala Ser Phe Gln Thr Arg
                85                  90                  95

Val Phe Glu Glu Phe Phe Val Arg Tyr Gly Ile Pro Tyr Lys Ile Ile
            100                 105                 110

Gly Gly Thr Lys Phe Tyr Asp Arg Val Glu Ile Arg Asp Leu Val Ala
        115                 120                 125

Tyr Leu Lys Val Val Val Asn Pro Asn Asn Asp Ile Ala Phe Glu Lys
    130                 135                 140

Ile Ile Asn Lys Pro Lys Arg Lys Leu Gly Thr Ser Thr Val Asn Lys
145                 150                 155                 160

Leu Arg Ala Tyr Gly Arg Lys His Ser Ile Ser Leu Thr Glu Ala Gly
                165                 170                 175

His Ser Met Ile Lys Asp Gly Leu Leu Ser Asp Asn Thr Ser Asn Ile
            180                 185                 190

Leu Gln Asp Leu Leu Lys Gln Phe Asp Asp Trp Arg Glu Met Leu Ser
        195                 200                 205

Arg Asp Ser Ser Val Asn Val Leu Lys Ala Ile Ala His Asp Ser Gly
    210                 215                 220

Tyr Ile Glu Ser Leu Lys Lys Asp Gly Glu Ser Gly Leu Ser Arg Ile
225                 230                 235                 240

Glu Asn Ile Lys Glu Leu Phe Ser Ala Val Ser Gly Phe Asp Asp Val
                245                 250                 255

Ser Lys Phe Leu Glu His Ile Ser Leu Val Ala Glu Asn Asp Ser Leu
            260                 265                 270

Glu Glu Asp Asn Asn Tyr Val His Val Met Thr Leu His Ala Ala Lys
        275                 280                 285

Gly Leu Glu Phe Pro Leu Val Phe Leu Pro Gly Trp Glu Glu Gly Val
    290                 295                 300

Phe Pro His Glu Lys Ser Met Asn Asp Ile Thr Gly Asn Ala Leu Glu
305                 310                 315                 320

Glu Glu Arg Arg Leu Ala Tyr Val Gly Ile Thr Arg Ala Arg Glu Gln
                325                 330                 335

Leu Tyr Ile Ser Cys Ala Ala Met Arg Glu Ile Asn Asn Trp Ser Gln
            340                 345                 350

Ser Met Lys Met Ser Arg Phe Ile Lys Glu Leu Pro Arg Glu His Val
        355                 360                 365

Gln Val Leu His Asn Met Thr Gly Tyr Ala
    370                 375
```

<210> SEQ ID NO 71
<211> LENGTH: 209
<212> TYPE: PRT

-continued

<213> ORGANISM: Ehrlichia sp.

<400> SEQUENCE: 71

```
Tyr Ile Asp Ser Leu Arg Ser His Ser Leu Leu Leu Lys Arg Lys Thr
 1               5                  10                  15

Lys Gly Ile Arg Asp Ser Gly Ser Lys Glu Asp Glu Ala Asp Thr Val
            20                  25                  30

Tyr Leu Leu Ala Lys Glu Leu Ala Tyr Asp Val Val Thr Gly Gln Thr
        35                  40                  45

Asp Asn Leu Ala Ala Ala Leu Ala Lys Thr Ser Gly Lys Asp Phe Val
    50                  55                  60

Lys Phe Ala Asn Ala Val Val Gly Ile Ser His Pro Asp Val Asn Lys
65                  70                  75                  80

Lys Val Cys Ala Thr Arg Lys Asp Ser Gly Gly Thr Arg Tyr Ala Lys
                85                  90                  95

Tyr Ala Ala Thr Thr Asn Lys Ser Ser Asn Pro Glu Thr Ser Leu Cys
            100                 105                 110

Gly Asp Glu Gly Gly Ser Ser Gly Thr Asn Asn Thr Gln Glu Phe Leu
        115                 120                 125

Lys Glu Phe Val Ala Lys Thr Leu Val Glu Asn Glu Ser Lys Asn Trp
    130                 135                 140

Pro Thr Ser Ser Gly Thr Gly Leu Lys Thr Asn Asp Asn Ala Lys Ala
145                 150                 155                 160

Val Ala Thr Asp Leu Val Ala Leu Asn Arg Asp Glu Lys Thr Ile Val
                165                 170                 175

Ala Gly Leu Leu Ala Lys Thr Ile Glu Gly Gly Glu Val Val Glu Ile
            180                 185                 190

Arg Ala Val Ser Ser Thr Ser Val Met Ala Leu Glu Leu Arg Val Cys
        195                 200                 205

Trp
```

<210> SEQ ID NO 72
<211> LENGTH: 261
<212> TYPE: PRT
<213> ORGANISM: Ehrlichia sp.

<400> SEQUENCE: 72

```
Lys Lys Ser Ile Ile Arg Glu Asp Glu Val Asp Thr Val Tyr Leu Leu
 1               5                  10                  15

Ala Lys Glu Leu Ala Tyr Asp Val Val Thr Gly Gln Thr Asp Lys Leu
            20                  25                  30

Thr Ala Ala Leu Ala Lys Thr Ser Gly Lys Asp Ile Val Gln Phe Ala
        35                  40                  45

Lys Ala Val Gly Val Ser His Pro Ser Ile Asp Gly Lys Val Cys Arg
    50                  55                  60

Thr Lys Arg Lys Ala Gly Asp Ser Ser Gly Thr Tyr Ala Lys Tyr Gly
65                  70                  75                  80

Glu Glu Thr Asp Asn Asn Thr Ser Gly Gln Ser Thr Val Ala Val Cys
                85                  90                  95

Gly Glu Lys Ala Gly His Asn Ala Asn Gly Ser Gly Thr Val Gln Ser
            100                 105                 110

Leu Lys Asp Phe Val Arg Glu Thr Leu Lys Ala Asp Gly Asn Arg Asn
        115                 120                 125

Trp Pro Thr Ser Arg Glu Lys Ser Gly Asn Thr Asn Thr Lys Pro Gln
    130                 135                 140
```

```
Pro Asn Asp Asn Ala Lys Ala Val Ala Lys Asp Leu Val Gln Glu Leu
145                 150                 155                 160

Asn His Asp Glu Lys Thr Ile Val Ala Gly Leu Leu Ala Lys Thr Ile
                165                 170                 175

Glu Gly Gly Glu Val Val Glu Ile Arg Ala Val Ser Ser Thr Ser Val
            180                 185                 190

Met Val Asn Ala Cys Tyr Asp Leu Leu Ser Glu Gly Leu Gly Val Val
        195                 200                 205

Pro Tyr Ala Cys Val Gly Leu Gly Gly Asn Phe Val Gly Val Val Asp
    210                 215                 220

Gly His Ile Thr Ile Arg Trp Ala Ser Thr Leu Tyr Ala His Ser Lys
225                 230                 235                 240

Ser Leu Gly Lys Ile Gly Ala Ala Ser Leu Arg Asn Arg Leu Arg Ser
                245                 250                 255

Ala Ile Leu His Thr
            260


<210> SEQ ID NO 73
<211> LENGTH: 530
<212> TYPE: PRT
<213> ORGANISM: Ehrlichia sp.

<400> SEQUENCE: 73

Leu Leu Tyr Ser Phe Gly Asn Leu Thr Ser Tyr Gly Arg Ser Val Met
 1               5                  10                  15

Arg Ser Arg Lys Ile Tyr Val Trp Val Val Met Ala Thr Val Leu Gly
            20                  25                  30

Ala Met Ala Phe Val Thr Phe Gly Ser Met Ile Pro Met Gly Lys Leu
        35                  40                  45

Ser Asn Ser Gly Asn Gly Gln Cys Val Ala Met Leu Gly Asn Lys Cys
    50                  55                  60

Leu Pro Leu Arg Asp Tyr Arg Ile Met Tyr Arg Asn Glu Leu Ala Glu
65                  70                  75                  80

Leu Glu Lys Met Leu Gln His Lys Leu Ser Asp Ala Gln Ile Asn Gln
                85                  90                  95

Phe Gly Ile Lys Glu Val Val Leu Lys Asn Met Ile Ala Asp Met Val
            100                 105                 110

Val Glu Lys Phe Ala His Asp Leu Gly Ile Arg Val Gly Ser Asn Ser
        115                 120                 125

Leu Arg Ser Leu Ile Lys Asn Ile Arg Ile Phe Gln Asp Ala Asn Gly
    130                 135                 140

Val Phe Asp Gln Glu Arg Tyr Glu Ala Val Leu Ala Asp Ser Gly Met
145                 150                 155                 160

Thr Glu Ser Ser Tyr Val Asn Lys Ile Arg Asn Ala Leu Pro Ser Thr
                165                 170                 175

Ile Leu Met Glu Cys Leu Phe Pro Asn Arg Ala Glu Leu His Ile Pro
            180                 185                 190

Tyr Tyr Asp Ala Leu Ala Lys Asp Val Val Leu Gly Leu Leu Gln His
        195                 200                 205

Arg Val Ala Asp Ile Val Glu Ile Ser Ser Asp Ala Val Asp Ile Ser
    210                 215                 220

Gly Ser Asp Ile Ser Asp Asp Glu Leu Gln Lys Leu Phe Glu Glu Gln
225                 230                 235                 240

Tyr Lys Asn Ser Leu Asn Phe Pro Glu Tyr Arg Ser Ala Asp Tyr Ile
```

-continued

```
                245                 250                 255

Ile Met Ala Glu Asp Asp Leu Leu Ala Asp Val Ile Val Ser Asp Gln
            260                 265                 270

Glu Val Asp Val Glu Ile Lys Asn Ser Glu Leu His Asp Gln Arg Asp
        275                 280                 285

Val Leu Asn Leu Val Phe Thr Asp Lys Asn Glu Ala Glu Leu Ala Tyr
    290                 295                 300

Lys Ala Tyr Gln Glu Gly Lys Ser Phe Glu Glu Leu Val Ser Asp Ala
305                 310                 315                 320

Gly Tyr Thr Ile Glu Asp Ile Ala Leu Asn Asn Ile Ser Lys Asp Val
                325                 330                 335

Leu Pro Val Gly Val Arg Asn Val Val Phe Ala Leu Asn Glu Gly Glu
            340                 345                 350

Val Ser Glu Met Phe Arg Ser Val Val Gly Trp His Ile Met Lys Val
        355                 360                 365

Ile Arg Lys His Glu Ile Thr Lys Glu Asp Leu Glu Lys Leu Lys Glu
    370                 375                 380

Lys Ile Ser Ser Asn Ile Arg Arg Gln Lys Ala Gly Glu Leu Leu Val
385                 390                 395                 400

Ser Asn Val Lys Lys Ala Asn Asp Met Ile Ser Arg Gly Ala Leu Leu
                405                 410                 415

Asn Glu Leu Lys Asp Met Phe Gly Ala Arg Ile Ser Gly Val Leu Thr
            420                 425                 430

Asn Phe Asp Met His Gly Leu Asp Lys Ser Gly Asn Leu Val Lys Asp
        435                 440                 445

Phe Pro Leu Gln Leu Gly Ile Asn Ala Phe Thr Thr Leu Ala Phe Ser
    450                 455                 460

Ser Ala Val Gly Lys Pro Ser His Leu Val Ser Asn Gly Asp Ala Tyr
465                 470                 475                 480

Phe Gly Val Leu Val Thr Glu Val Val Pro Pro Arg Pro Arg Thr Leu
                485                 490                 495

Glu Glu Ser Arg Ser Ile Leu Thr Glu Glu Trp Lys Ser Ala Leu Arg
            500                 505                 510

Met Lys Lys Ile Arg Glu Phe Ala Val Glu Leu Arg Ser Lys Leu Gln
        515                 520                 525

Asn Gly
    530


<210> SEQ ID NO 74
<211> LENGTH: 25
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 74

aaaggggctc cagcaacgca gagag                                            25


<210> SEQ ID NO 75
<211> LENGTH: 32
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 75
```

```
catagaattc gatcgatcga gtagctggaa cc                                   32


<210> SEQ ID NO 76
<211> LENGTH: 28
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 76

caccgtcgat cgttctatat tggtttgg                                        28


<210> SEQ ID NO 77
<211> LENGTH: 32
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 77

cttgactcga gttaaagatg gtttgtgtaa tg                                   32


<210> SEQ ID NO 78
<211> LENGTH: 29
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 78

cttatcgatc ggagcttgag attggttac                                       29


<210> SEQ ID NO 79
<211> LENGTH: 31
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 79

caatgcgaat tcattaaaaa gcgagcctaa c                                    31


<210> SEQ ID NO 80
<211> LENGTH: 33
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 80

ctacatcacg tgttctatat tggtttggat tac                                  33


<210> SEQ ID NO 81
<211> LENGTH: 34
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 81
```

```
ggttaactcg agtactaaga tggtttgtgt aatg                                34


<210> SEQ ID NO 82
<211> LENGTH: 27
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 82

gagcttgaga ttggttacga gcgcttc                                        27


<210> SEQ ID NO 83
<211> LENGTH: 32
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 83

caattactcg agaattcatt aaaaagcgag cc                                  32


<210> SEQ ID NO 84
<211> LENGTH: 1980
<212> TYPE: DNA
<213> ORGANISM: Artificial Sequence
<220> FEATURE:
<223> OTHER INFORMATION: DNA fusion construct containing HGE-3 and HGE-1
      antigens

<400> SEQUENCE: 84

atgcagcatc accaccatca ccacgtgttc tatattggtt tggattacag tccagcgttt     60

agcaagataa gagattttag tataagggag agtaacggag agacaaaggc agtatatcca    120

tacttaaagg atggaaagag tgtaaagcta gagtcacaca agtttgactg gaacacacct    180

gatcctcgga ttgggtttaa ggacaacatg cttgtagcta tggaaggtag tgttggttat    240

ggtattggtg gtgccagggt tgagcttgag attggttacg agcgcttcaa gaccaagggt    300

attagagata gtggtagtaa ggaagatgaa gctgatacag tatatctact agctaaggag    360

ttagcttatg atgttgttac tggacagact gataaccttg ctgctgctct tgctaagacc    420

tcggggaaag acatcgttca gtttgctaag gcggttgggg tttctcatcc tagtattgat    480

gggaaggttt gtaagacgaa ggcggatagc tcgaagaaat ttccgttata tagtgacgaa    540

acgcacacga agggggcaaa tgaggggaga acgtctttgt gcggtgacaa tggtagttct    600

acgataacaa ccagtggtac gaatgtaagt gaaactgggc aggtttttag ggattttatc    660

agggcaacgc tgaaagagga tggtagtaaa aactggccaa cttcaagcgg cacgggaact    720

ccaaaacctg tcacgaacga caacgccaaa gccgtagcta aagacctagt acaggagcta    780

acccctgaag aaaaaaccat agtagcaggg ttactagcta agactattga agggggtgaa    840

gttgttgaga tcagggcggt ttcttctact tccgtaatgg tcaatgcttg ttatgatctt    900

cttagtgaag gtttaggtgt tgttccttat gcttgtgttg gtctcggtgg taacttcgtg    960

ggcgtggttg atggaattca ttacacaaac catcttagtg agcttgagat tggttacgag   1020

cgcttcaaga ccaagggtat tagagatagt ggtagtaagg aagatgaagc tgatacagta   1080

tatctactag ctaaggagtt agcttatgat gttgttactg gtcagactga taaccttgcc   1140

gctgctcttg ccaaaacctc cggtaaggat attgttcagt ttgctaaggc ggtggagatt   1200
```

-continued

```
tctcattccg agattgatgg caaggtttgt aagacgaagt cggcgggaac tggaaaaaat   1260

ccgtgtgatc atagccaaaa gccgtgtagt acgaatgcgt attatgcgag gagaacgcag   1320

aagagtagga gttcgggaaa aacgtcttta tgcggggaca gtgggtatag cgggcaggag   1380

ctaataacgg gtgggcatta tagcagtcca agcgtattcc ggaattttgt caaagacaca   1440

ctacaaggaa atggtagtga gaactggcct acatctactg gagaaggaag tgagagtaac   1500

gacaacgcca tagccgttgc taaggaccta gtaaatgaac ttactcctga agaacgaacc   1560

atagtggctg ggttacttgc taaaattatt gaaggaagcg aggttattga gattagggcc   1620

atctcttcga cttcagttac aatgaatatt tgctcagata tcacgataag taatatctta   1680

atgccgtatg tttgtgttgg tccagggatg agctttgtta gtgttgttga tggtcacact   1740

gctgcaaagt ttgcatatcg gttaaaggca ggtctgagtt ataaattttc gaaagaagtt   1800

acagcttttg caggtggttt ttaccatcac gttataggag atggtgttta tgatgatctg   1860

ccattgcggc atttatctga tgatattagt cctgtgaaac atgctaagga aaccgccatt   1920

gctagattcg tcatgaggta ctttggcggg gaatttggtg ttaggctcgc tttttaatga   1980
```

```
<210> SEQ ID NO 85
<211> LENGTH: 658
<212> TYPE: PRT
<213> ORGANISM: Artificial Sequence
<220> FEATURE:
<223> OTHER INFORMATION: Amino acid sequence of fusion protein
      containing HGE-3 and HGE-1 antigens

<400> SEQUENCE: 85

Met Gln His His His His His His Val Phe Tyr Ile Gly Leu Asp Tyr
 1               5                  10                  15

Ser Pro Ala Phe Ser Lys Ile Arg Asp Phe Ser Ile Arg Glu Ser Asn
            20                  25                  30

Gly Glu Thr Lys Ala Val Tyr Pro Tyr Leu Lys Asp Gly Lys Ser Val
        35                  40                  45

Lys Leu Glu Ser His Lys Phe Asp Trp Asn Thr Pro Asp Pro Arg Ile
    50                  55                  60

Gly Phe Lys Asp Asn Met Leu Val Ala Met Glu Gly Ser Val Gly Tyr
65                  70                  75                  80

Gly Ile Gly Gly Ala Arg Val Glu Leu Glu Ile Gly Tyr Glu Arg Phe
                85                  90                  95

Lys Thr Lys Gly Ile Arg Asp Ser Gly Ser Lys Glu Asp Glu Ala Asp
            100                 105                 110

Thr Val Tyr Leu Leu Ala Lys Glu Leu Ala Tyr Asp Val Val Thr Gly
        115                 120                 125

Gln Thr Asp Asn Leu Ala Ala Ala Leu Ala Lys Thr Ser Gly Lys Asp
    130                 135                 140

Ile Val Gln Phe Ala Lys Ala Val Gly Val Ser His Pro Ser Ile Asp
145                 150                 155                 160

Gly Lys Val Cys Lys Thr Lys Ala Asp Ser Ser Lys Lys Phe Pro Leu
                165                 170                 175

Tyr Ser Asp Glu Thr His Thr Lys Gly Ala Asn Glu Gly Arg Thr Ser
            180                 185                 190

Leu Cys Gly Asp Asn Gly Ser Ser Thr Ile Thr Thr Ser Gly Thr Asn
        195                 200                 205

Val Ser Glu Thr Gly Gln Val Phe Arg Asp Phe Ile Arg Ala Thr Leu
    210                 215                 220
```

-continued

```
Lys Glu Asp Gly Ser Lys Asn Trp Pro Thr Ser Ser Gly Thr Gly Thr
225                 230                 235                 240

Pro Lys Pro Val Thr Asn Asp Asn Ala Lys Ala Val Ala Lys Asp Leu
                245                 250                 255

Val Gln Glu Leu Thr Pro Glu Glu Lys Thr Ile Val Ala Gly Leu Leu
            260                 265                 270

Ala Lys Thr Ile Glu Gly Gly Glu Val Val Glu Ile Arg Ala Val Ser
        275                 280                 285

Ser Thr Ser Val Met Val Asn Ala Cys Tyr Asp Leu Leu Ser Glu Gly
    290                 295                 300

Leu Gly Val Val Pro Tyr Ala Cys Val Gly Leu Gly Gly Asn Phe Val
305                 310                 315                 320

Gly Val Val Asp Gly Ile His Tyr Thr Asn His Leu Ser Glu Leu Glu
                325                 330                 335

Ile Gly Tyr Glu Arg Phe Lys Thr Lys Gly Ile Arg Asp Ser Gly Ser
            340                 345                 350

Lys Glu Asp Glu Ala Asp Thr Val Tyr Leu Leu Ala Lys Glu Leu Ala
        355                 360                 365

Tyr Asp Val Val Thr Gly Gln Thr Asp Asn Leu Ala Ala Ala Leu Ala
    370                 375                 380

Lys Thr Ser Gly Lys Asp Ile Val Gln Phe Ala Lys Ala Val Glu Ile
385                 390                 395                 400

Ser His Ser Glu Ile Asp Gly Lys Val Cys Lys Thr Lys Ser Ala Gly
                405                 410                 415

Thr Gly Lys Asn Pro Cys Asp His Ser Gln Lys Pro Cys Ser Thr Asn
            420                 425                 430

Ala Tyr Tyr Ala Arg Arg Thr Gln Lys Ser Arg Ser Ser Gly Lys Thr
        435                 440                 445

Ser Leu Cys Gly Asp Ser Gly Tyr Ser Gly Gln Glu Leu Ile Thr Gly
    450                 455                 460

Gly His Tyr Ser Ser Pro Ser Val Phe Arg Asn Phe Val Lys Asp Thr
465                 470                 475                 480

Leu Gln Gly Asn Gly Ser Glu Asn Trp Pro Thr Ser Thr Gly Glu Gly
                485                 490                 495

Ser Glu Ser Asn Asp Asn Ala Ile Ala Val Ala Lys Asp Leu Val Asn
            500                 505                 510

Glu Leu Thr Pro Glu Glu Arg Thr Ile Val Ala Gly Leu Leu Ala Lys
        515                 520                 525

Ile Ile Glu Gly Ser Glu Val Ile Glu Ile Arg Ala Ile Ser Ser Thr
    530                 535                 540

Ser Val Thr Met Asn Ile Cys Ser Asp Ile Thr Ile Ser Asn Ile Leu
545                 550                 555                 560

Met Pro Tyr Val Cys Val Gly Pro Gly Met Ser Phe Val Ser Val Val
                565                 570                 575

Asp Gly His Thr Ala Ala Lys Phe Ala Tyr Arg Leu Lys Ala Gly Leu
            580                 585                 590

Ser Tyr Lys Phe Ser Lys Glu Val Thr Ala Phe Ala Gly Gly Phe Tyr
        595                 600                 605

His His Val Ile Gly Asp Gly Val Tyr Asp Asp Leu Pro Leu Arg His
    610                 615                 620

Leu Ser Asp Asp Ile Ser Pro Val Lys His Ala Lys Glu Thr Ala Ile
625                 630                 635                 640

Ala Arg Phe Val Met Arg Tyr Phe Gly Gly Glu Phe Gly Val Arg Leu
```

-continued 645 650 655

Ala Phe

<210> SEQ ID NO 86
<211> LENGTH: 3300
<212> TYPE: DNA
<213> ORGANISM: Ehrlichia (HGE)

<400> SEQUENCE: 86
taaaataatc tgccccttt agagcgttat gtactctaaa aggggtatta ttaaagtggc 60
gagatcatcg cctaaatact cagaagcgcg aattatattg atcaaagtac ctcagcgatt 120
tttcggtata attctaccta ccgcgacctc cttttacaga cttagggcct tcactttgag 180
gagcttctgg ttgagatcct ggggcaccag attccatgcc aagatcttgc tttgcctttg 240
cagctcctcc atcacccttc tgagcttctt caactgctcc ctgtaatcct tcggcagctt 300
ttgttagttc ctttttgaac tctttactgg agaatataga agtagctgtt ttgtctttgg 360
tagaatccgg agcacctccc ttcacaggac gcaatttacc cctttgtgct tgcagctcag 420
ctgcaaaaga gctactagtt cctgaactca ggtctttatc agaacctata ccttctttag 480
taggcaaact acttgtccta gctggaacct gaggtttcac tttcttctta atcacagtta 540
ttgttgagcc gactttttca gaagctgttc cttctttttg agaagtatca ctcttcttag 600
gacccttttt cactgttgca taaatcggct cttccttagg gccaaatgtc gttactccag 660
aagatgttcg ttccgcagca aatgggtcag catagataga ttcaggcctt tcctgcctag 720
gtttcactat atcaaatgga tcagcataaa tggattccgg cctttctccc ttagatgacg 780
ccgcatctga tgcttgcgcc tcggaagtaa ttgcagctcc cacagtagca tacagatctt 840
caccttctgg tgttctcgga ccttcagctc ctacagttgt atatgtgctt tcaacttccg 900
ttgtaccttt tgctgtatcc ttaatttctt cgtagataga ctcctcagct cctacagttg 960
tatatgtgct ttcaacttcc gttgtacctt ttgctgtatc cttaatttct tcgtagatag 1020
actcctcagc tcctgcagta tctaggccac tacccaagga tgatagcgca gagacactct 1080
caaaacttga aatagatcct aaagaaggag ttggactttc aggcggcaga tatggtggga 1140 atccccccttc aggaacttga acacgttcag ccatcattgt gacaacggac tttccaaaaa 1200
accacggacg agttttcaat gatggatccg caacatcgac cggtgttttt ccctctacat 1260
tcacgactga tactgacgcc ccagacttta gtagtatttt acatgcttta ccgaaaccac 1320
gcgatgcagc cagatgcagt aacgtgtcac catttgcttc ttgaggagta ttaagcaagt 1380
ctccgaaaga tgagtttgac aaatgctttc gagactcttt aagcatcttt aaaaagcatt 1440
tttctgtaac cttatcagaa tataaagcct catgtaacgc tgtatctccc atatgagaaa 1500
ggagtgcttg acagctatct gggcattttt tcgcaattaa cttatatagc ttaccgtcac 1560
cattagcagc tgctatatgt aaagccgtct taccataagc atctctctgc gttgctggag 1620
cccctttatc caagagcaac ctagcagtct tctggttgcc agcagctgtt gctaaatgca 1680
aggctggagt tccagtgtga tccgtagacg aaagatctgc acccctctgt aaaaggaaat 1740
ttacaatcct attagcctct ttaaggttac ttgcctcatt tgccacttga actgcagcag 1800
ctaaagggct catagatccg gtaggagtat ttatatgtgc cccagcttct acaacacgct 1860
ttaaatgctt tatagcttta cccccctgaa agcaccctcc ttgtataccc acagaaatag 1920
ctggttctgg agacgcattt acatcagcac tgtttttaat taacgtcttc actgcagcat 1980
attgaccact agttagtgct tcagcggtca aagttgtctt ttttccttca ggagttgtaa 2040

```
tttcttcatt tacactaatc acttcagtgg taataagatg cctcaataca tctgctgcac   2100

cttttcttac tgcctcgaca gcaacatgct gcgggtaagg ctcatatctc attaacatgt   2160

caagtgctgg tagcgatact tttccaccac ttgcttcacg aatcgcatat acacctggag   2220

taggaacacc atcctttaca ggaaacttag aataactact cttccttcca agagcctgct   2280

gcaatatctc taaatttcca tcctttgctg cgtaatgtat tatagttcca ccatcatgtg   2340

accgagcatc tacgtccatg ctattacagc gtaacatagt cttaacaccc tcagtgttgc   2400

ccctttata cgcagctacc acaggcgttt cacctgtcac tggagatggt acattgattg    2460

atggaatatt acgcacattc tcaatcaaca tctgcaattt aacgcttacg cctttatggc   2520

ttggctcatc ctcaactatc atgtgaatag gcgctttgcc attcggtgct aattgattta   2580

caacagactc aggagtgcat cttaccacct gctcaaaaac cccactgtt gatttttgtg    2640

ctgcagcatg tataggtgca ttacctgcaa tatctaaatt agtaaaaggt tcctctccat   2700

acctatgata tgcttcctcc aataccctt tcgcaagagg atcaaaattt ggggtcccat    2760

tagaagatac aaaatgcacc agcgttgatg cgtcctctgg attaggacat gtaaagagag   2820

attttacttc tgaagaagct gagccataca ctttatctgc aatgttcatg gccttctcga   2880

agatcttctc agcctccggt atatgccttc taatagcata ctgtactgca ctcatccctt   2940

ttttatccgg gaatattagt gcctctgcac actcgcgatt gccctcaata tttgacgaca   3000

ccgcttcttg catcttgtca atgtatgata aaacatcccg ccttggccat tgctttgcaa   3060

caatgtggca aacggtttca ccagcatcat ttgcaacgct aatatcactt aaccttgaga   3120

gaagatgctt tactttctgg tgatccatac gctccgtagc aatatgaagc ggagtgtttc   3180

cacccggtcc cttagcatta acatctgcta taagagcttt gtcgcatagt acatcaagat   3240

tgcctaaagc atttttgcct actgaagatg cagctgtatg taatggcgta ttaccatcta   3300
```

<210> SEQ ID NO 87
<211> LENGTH: 1054
<212> TYPE: PRT
<213> ORGANISM: Ehrlichia (HGE)

<400> SEQUENCE: 87

```
Asp Gly Asn Thr Pro Leu His Thr Ala Ala Ser Ser Val Gly Lys Asn
                5                   10                  15

Ala Leu Gly Asn Leu Asp Val Leu Cys Asp Lys Ala Leu Ile Ala Asp
            20                  25                  30

Val Asn Ala Lys Gly Pro Gly Gly Asn Thr Pro Leu His Ile Ala Thr
        35                  40                  45

Glu Arg Met Asp His Gln Lys Val Lys His Leu Leu Ser Arg Leu Ser
    50                  55                  60

Asp Ile Ser Val Ala Asn Asp Ala Gly Glu Thr Val Cys His Ile Val
65                  70                  75                  80

Ala Lys Gln Trp Pro Arg Arg Asp Val Leu Ser Tyr Ile Asp Lys Met
                85                  90                  95

Gln Glu Ala Val Ser Ser Asn Ile Glu Gly Asn Arg Glu Cys Ala Glu
            100                 105                 110

Ala Leu Ile Phe Pro Asp Lys Lys Gly Met Ser Ala Val Gln Tyr Ala
        115                 120                 125

Ile Arg Arg His Ile Pro Glu Ala Glu Lys Ile Phe Glu Lys Ala Met
    130                 135                 140

Asn Ile Ala Asp Lys Val Tyr Gly Ser Ala Ser Ser Glu Val Lys Ser
```

-continued

```
145                 150                 155                 160

Leu Phe Thr Cys Pro Asn Pro Glu Asp Ala Ser Thr Leu Val His Phe
                165                 170                 175

Val Ser Ser Asn Gly Thr Pro Asn Phe Asp Pro Leu Ala Lys Arg Val
            180                 185                 190

Leu Glu Glu Ala Tyr His Arg Tyr Gly Glu Glu Pro Phe Thr Asn Leu
        195                 200                 205

Asp Ile Ala Gly Asn Ala Pro Ile His Ala Ala Ala Gln Lys Ser Thr
    210                 215                 220

Val Gly Val Phe Glu Gln Val Val Arg Cys Thr Pro Glu Ser Val Val
225                 230                 235                 240

Asn Gln Leu Ala Pro Asn Gly Lys Ala Pro Ile His Met Ile Val Glu
                245                 250                 255

Asp Glu Pro Ser His Lys Gly Val Ser Val Lys Leu Gln Met Leu Ile
            260                 265                 270

Glu Asn Val Arg Asn Ile Pro Ser Ile Asn Val Pro Ser Pro Val Thr
        275                 280                 285

Gly Glu Thr Pro Val Val Ala Ala Tyr Lys Gly Gly Asn Thr Glu Gly
    290                 295                 300

Val Lys Thr Met Leu Arg Cys Asn Ser Met Asp Val Asp Ala Arg Ser
305                 310                 315                 320

His Asp Gly Gly Thr Ile Ile His Tyr Ala Ala Lys Asp Gly Asn Leu
                325                 330                 335

Glu Ile Leu Gln Gln Ala Leu Gly Arg Lys Ser Ser Tyr Ser Lys Phe
            340                 345                 350

Pro Val Lys Asp Gly Val Pro Thr Pro Gly Val Tyr Ala Ile Arg Glu
        355                 360                 365

Ala Ser Gly Gly Lys Val Ser Leu Pro Ala Leu Asp Met Leu Met Arg
    370                 375                 380

Tyr Glu Pro Tyr Pro Gln His Val Ala Val Glu Ala Val Arg Lys Gly
385                 390                 395                 400

Ala Ala Asp Val Leu Arg His Leu Ile Thr Thr Glu Val Ile Ser Val
                405                 410                 415

Asn Glu Glu Ile Thr Thr Pro Glu Gly Lys Lys Thr Thr Leu Thr Ala
            420                 425                 430

Glu Ala Leu Thr Ser Gly Gln Tyr Ala Ala Val Lys Thr Leu Ile Lys
        435                 440                 445

Asn Ser Ala Asp Val Asn Ala Ser Pro Glu Pro Ala Ile Ser Val Gly
    450                 455                 460

Ile Gln Gly Gly Cys Phe Gln Gly Gly Lys Ala Ile Lys His Leu Lys
465                 470                 475                 480

Arg Val Val Glu Ala Gly Ala His Ile Asn Thr Pro Thr Gly Ser Met
                485                 490                 495

Ser Pro Leu Ala Ala Ala Val Gln Val Ala Asn Glu Ala Ser Asn Leu
            500                 505                 510

Lys Glu Ala Asn Arg Ile Val Asn Phe Leu Leu Gln Arg Gly Ala Asp
        515                 520                 525

Leu Ser Ser Thr Asp His Thr Gly Thr Pro Ala Leu His Leu Ala Thr
    530                 535                 540

Ala Ala Gly Asn Gln Lys Thr Ala Arg Leu Leu Leu Asp Lys Gly Ala
545                 550                 555                 560

Pro Ala Thr Gln Arg Asp Ala Tyr Gly Lys Thr Ala Leu His Ile Ala
                565                 570                 575
```

```
Ala Ala Asn Gly Asp Gly Lys Leu Tyr Lys Leu Ile Ala Lys Lys Cys
            580                 585                 590

Pro Asp Ser Cys Gln Ala Leu Leu Ser His Met Gly Asp Thr Ala Leu
        595                 600                 605

His Glu Ala Leu Tyr Ser Asp Lys Val Thr Glu Lys Cys Phe Leu Lys
    610                 615                 620

Met Leu Lys Glu Ser Arg Lys His Leu Ser Asn Ser Ser Phe Gly Asp
625                 630                 635                 640

Leu Leu Asn Thr Pro Gln Glu Ala Asn Gly Asp Thr Leu Leu His Leu
                645                 650                 655

Ala Ala Ser Arg Gly Phe Gly Lys Ala Cys Lys Ile Leu Leu Lys Ser
            660                 665                 670

Gly Ala Ser Val Ser Val Val Asn Val Glu Gly Lys Thr Pro Val Asp
        675                 680                 685

Val Ala Asp Pro Ser Leu Lys Thr Arg Pro Trp Phe Phe Gly Lys Ser
    690                 695                 700

Val Val Thr Met Met Ala Glu Arg Val Gln Val Pro Glu Gly Gly Phe
705                 710                 715                 720

Pro Pro Tyr Leu Pro Pro Glu Ser Pro Thr Pro Ser Leu Gly Ser Ile
                725                 730                 735

Ser Ser Phe Glu Ser Val Ser Ala Leu Ser Ser Leu Gly Ser Gly Leu
            740                 745                 750

Asp Thr Ala Gly Ala Glu Glu Ser Ile Tyr Glu Glu Ile Lys Asp Thr
        755                 760                 765

Ala Lys Gly Thr Thr Glu Val Glu Ser Thr Tyr Thr Thr Val Gly Ala
    770                 775                 780

Glu Glu Ser Ile Tyr Glu Glu Ile Lys Asp Thr Ala Lys Gly Thr Thr
785                 790                 795                 800

Glu Val Glu Ser Thr Tyr Thr Thr Val Gly Ala Glu Gly Pro Arg Thr
                805                 810                 815

Pro Glu Gly Glu Asp Leu Tyr Ala Thr Val Gly Ala Ala Ile Thr Ser
            820                 825                 830

Glu Ala Gln Ala Ser Asp Ala Ala Ser Ser Lys Gly Glu Arg Pro Glu
        835                 840                 845

Ser Ile Tyr Ala Asp Pro Phe Asp Ile Val Lys Pro Arg Gln Glu Arg
    850                 855                 860

Pro Glu Ser Ile Tyr Ala Asp Pro Phe Ala Ala Glu Arg Thr Ser Ser
865                 870                 875                 880

Gly Val Thr Thr Phe Gly Pro Lys Glu Glu Pro Ile Tyr Ala Thr Val
                885                 890                 895

Lys Lys Gly Pro Lys Lys Ser Asp Thr Ser Gln Lys Glu Gly Thr Ala
            900                 905                 910

Ser Glu Lys Val Gly Ser Thr Ile Thr Val Ile Lys Lys Lys Val Lys
        915                 920                 925

Pro Gln Val Pro Ala Arg Thr Ser Ser Leu Pro Thr Lys Glu Gly Ile
    930                 935                 940

Gly Ser Asp Lys Asp Leu Ser Ser Gly Thr Ser Ser Ser Phe Ala Ala
945                 950                 955                 960

Glu Leu Gln Ala Gln Arg Gly Lys Leu Arg Pro Val Lys Gly Gly Ala
                965                 970                 975

Pro Asp Ser Thr Lys Asp Lys Thr Ala Thr Ser Ile Phe Ser Ser Lys
            980                 985                 990
```

-continued

```
Glu Phe Lys Lys Glu Leu Thr Lys Ala Ala Glu Gly Leu Gln Gly Ala
        995                 1000                1005

Val Glu Glu Ala Gln Lys Gly Asp Gly Gly Ala Ala Lys Ala Lys Gln
    1010                1015                1020

Asp Leu Gly Met Glu Ser Gly Ala Pro Gly Ser Gln Pro Glu Ala Pro
1025                1030                1035                1040

Gln Ser Glu Gly Pro Lys Ser Val Lys Gly Gly Arg Gly Arg
                1045                1050


<210> SEQ ID NO 88
<211> LENGTH: 3735
<212> TYPE: DNA
<213> ORGANISM: Ehrlichia

<400> SEQUENCE: 88

aatgcgctcc acataactag cataacgttt tcagcaacgg cagatcttca tatataagca     60

ctgaacacct acgttccaag atcatgctct tcgcgcctgt ttacttggtg gctcagagtc    120

atcatcacta ggagttcgtg gtctgtgaga gctaacttgt gcttcttcca gcgtagaact    180

agcacctccc aatcctgatg ctgaaggttg atcccacgaa taaggcataa tcccttgatc    240

ctgaggtggc acatagggag cttgtgatct tcccattcca gtactagtac ctcctagccc    300

agatgttgag aattggctag atggataagg aacattctct aggacacgta gtagaatatg    360

aggggggggg ggaacgagtt gagctccctg tccggcagta cctcccaatc ctgatgttga    420

gggttgatcc catgatgttg agggttgatc ccacgatgtt gaaggttgtg catacgaata    480

gggcatcatc cctggatcat gtggtggaat atgcgaagct tgttgacttc ccattccagc    540

ggcacttcct aaccctgatg ttgagggttg atcccacgat gttgaaggtt gtgcatacga    600

atagggcatc atccctggat catgtggtgg aatatgcgaa gcttgttgac ttcccattcc    660

agcggcactt cctaaccctg atgttgaggg ttgatcccac gatgttgaag gttgtgcata    720

cgaatagggc atcatccctg gatcatgtgg tggaatatgc gaagcttgtt gacttcccgt    780

tccagcggca cttcctaacc ctgatgttga gggttgatcc cacaatgttg aaggttgtgc    840

atacgaatag ggcatcatcc ctggatcatg tggtggaata tgcgaagctt gttgacttcc    900

cgttccagca gtacccccca ttcctgatgt tgagggttga tcccacggcg caccataggg    960

tatgggtata cgctcaagaa cacgtagtgg gacactgata gcttgtgctc cttccactcc   1020

agcactagta ctccctaatc ctgatgtcga gggttgacta ggtgcagcac cggtctgctc   1080

aacagcattg aaatatcttc cgtatttctt gtcacaaata ttcatcatta ctgaaagata   1140

ccgcaatgct gtattgcgcc acttgacttc tatctgtgga attaatagcg catcttccgt   1200

aatatgctca ttgatctcct catagacatg gcacatgtct aaaaatgatt tgcgagccct   1260

gtatgccccg agctcccttc ttctgctata taaagcacac aaaatctgga gacaatgccc   1320

aatcctacct gcaacaacat gatctacatt accggtggaa gcgtatactc tatacatcaa   1380

gaacaaacca cctactgcat gcactaaagc accaccccga tacctttctc gcttgagtcg   1440

taaatcaaaa ctgtgaactc ctaaaccttc aacatatgcc tctaaatagt agagaaaatt   1500

tgccatcgct cttctagaga gtcctagacg caggcgtgca ctttcattat tacgtaccat   1560

cgcttcacat gcagctgcac tagtctcaat agcatcaata acactgtcca agcaagcctc   1620

tgtacgatga cggaaaaaac gcggtgtatt aggctcaact aactcagcaa ccttactgca   1680

aagctctatg ttatgccgca ctacgcgcaa aatcgccttt atattctctg tttcctcaga   1740

atccaaagaa gaatttaagc atctacttaa ggctgaaaat tttacatagc agtatgcact   1800
```

-continued

```
taaagctgtc actgtatgag atgcactacc atctctacgc tcactactca ctgcaccagt   1860
aaacctcgtg gcaatagttc tggcacagca gttcactata gcaataacat tcactatgat   1920
agcacatgcc ttgcctattt gtaggtgtgc cttacgctta ataaagtctt gatccatgaa   1980
cagcggcact tctttgttgc actgcgccgt gatgcagtcc tgcaacgcgt cgtacaaccg   2040
attgatcaaa ctatacaaca cccccggttc tgcgcttgaa gcaccttctg cagcagttat   2100
acagctgtta atactgtcta tcttatcagc tgccgcaaac acgacatcta caccccggag   2160
cttgacaaac gtatcgcgca attccagcat acattgacgt atagcctgca ggcatgcagc   2220
atatggcctg gaattagtca ttattgaatt acatacagtt tctttatatt ccgcagaaga   2280
gcaaccactg taggcatatc cagacataac tggagtagtg aatatacgag gcatatgcat   2340
ctaattaacc actggaacaa cttcacacct tgaaagtgta gcataccggt gtgacgcagc   2400
tcaatattaa agattatgca cttcgtgatc gtctactagg aggctcaagt tcatcatcac   2460
taggagtttg tgatctagga gagactacct gtgctccttc cagcgtagaa ctagcacctc   2520
ctaatcctga tgttgagggt tgtgcatacg aataatcttg caacggacca caaggtgcct   2580
gagcttgcag tgctccctgt ccagcaggat tacctcccaa tcccgatgtt gagggttgac   2640
taggtgaaga gggcatatgc cctggatcat gaggtagcgt ataggaagct tgtgatcctc   2700
ctattccagc cccagcactt cctagtctag atgttgaggg ttgactaggc gaaccctcag   2760
tctgcctaat attattgaaa tatctctcgt acttcttttc ccaaatacca atcattgccg   2820
aaagataccc caacatagca ctacagaacc caacttctgt ctggggattt aatagtagac   2880
ctcgcgtaac gcattcctga atctcatcat agacagtaca catgtccaaa tataattctt   2940
gtgccgtata ttctgaagct cccgctcttc tgaccttata tttatagaga gtaagcaaca   3000
tttgaagaca atgctcaatt ttactcgcaa caacatgccc tgtattaccc gtggaagcat   3060
atactctgtg cattgagaat aaactaccaa ttgcatacac taaagcttgc acatacttgt   3120
catgcctgaa acttttaaaa gcaacgctca gtcctaaact tttatatgtc ttgaaatggt   3180
gtaaaaaacc tgttctcgct tttttagcga gagctaggcg gttctttgca ctatcgttat   3240
cactcaccat ctcttcgcat tcagccgagg tagacccaac tgcatcaagc atactgttta   3300
agcaactcac cgtacgatca cggaaacaat atggaatctc cggatcaact agctcagcaa   3360
ccttattaca aagctctatg ttatgcctca ccacacgtag aatagccttt ctacgcttag   3420
tttcctcagg acccggagaa taatttaaac atctgcttaa agctgaaaat tttgcattta   3480
cgtatgcact taaagccatg ttggcatgat acgcactatg ctcatcagcc tcacctattg   3540
cactgtcaga cgcctcggtt aaggttgtga caaagcagct tgccatggta atagcattca   3600
ccaggatagc acatacctta gcgatttgta ggtgtacttc acgcctcgtg aagtctggat   3660
ccatgaaccg cggcacttct ttgttgcact gcgccgtggc acagtcatgc agcatattat   3720
atgcactatg gatta                                                    3735
```

<210> SEQ ID NO 89
<211> LENGTH: 752
<212> TYPE: PRT
<213> ORGANISM: Ehrlichia

<400> SEQUENCE: 89

```
Met His Met Pro Arg Ile Phe Thr Thr Pro Val Met Ser Gly Tyr Ala
                5                   10                  15

Tyr Ser Gly Cys Ser Ser Ala Glu Tyr Lys Glu Thr Val Cys Asn Ser
```

-continued

```
            20                  25                  30

Ile Met Thr Asn Ser Arg Pro Tyr Ala Ala Cys Leu Gln Ala Ile Arg
        35                  40                  45

Gln Cys Met Leu Glu Leu Arg Asp Thr Phe Val Lys Leu Arg Gly Val
    50                  55                  60

Asp Val Val Phe Ala Ala Ala Asp Lys Ile Asp Ser Ile Asn Ser Cys
65                  70                  75                  80

Ile Thr Ala Ala Glu Gly Ala Ser Ser Ala Glu Pro Gly Val Leu Tyr
                85                  90                  95

Ser Leu Ile Asn Arg Leu Tyr Asp Ala Leu Gln Asp Cys Ile Thr Ala
            100                 105                 110

Gln Cys Asn Lys Glu Val Pro Leu Phe Met Asp Gln Asp Phe Ile Lys
        115                 120                 125

Arg Lys Ala His Leu Gln Ile Gly Lys Ala Cys Ala Ile Ile Val Asn
    130                 135                 140

Val Ile Ala Ile Val Asn Cys Cys Ala Arg Thr Ile Ala Thr Arg Phe
145                 150                 155                 160

Thr Gly Ala Val Ser Ser Glu Arg Arg Asp Gly Ser Ala Ser His Thr
                165                 170                 175

Val Thr Ala Leu Ser Ala Tyr Cys Tyr Val Lys Phe Ser Ala Leu Ser
            180                 185                 190

Arg Cys Leu Asn Ser Ser Leu Asp Ser Glu Glu Thr Glu Asn Ile Lys
        195                 200                 205

Ala Ile Leu Arg Val Val Arg His Asn Ile Glu Leu Cys Ser Lys Val
    210                 215                 220

Ala Glu Leu Val Glu Pro Asn Thr Pro Arg Phe Phe Arg His Arg Thr
225                 230                 235                 240

Glu Ala Cys Leu Asp Ser Val Ile Asp Ala Ile Glu Thr Ser Ala Ala
                245                 250                 255

Ala Cys Glu Ala Met Val Arg Asn Asn Glu Ser Ala Arg Leu Arg Leu
            260                 265                 270

Gly Leu Ser Arg Arg Ala Met Ala Asn Phe Leu Tyr Tyr Leu Glu Ala
        275                 280                 285

Tyr Val Glu Gly Leu Gly Val His Ser Phe Asp Leu Arg Leu Lys Arg
    290                 295                 300

Glu Arg Tyr Arg Gly Gly Ala Leu Val His Ala Val Gly Gly Leu Phe
305                 310                 315                 320

Leu Met Tyr Arg Val Tyr Ala Ser Thr Gly Asn Val Asp His Val Val
                325                 330                 335

Ala Gly Arg Ile Gly His Cys Leu Gln Ile Leu Cys Ala Leu Tyr Ser
            340                 345                 350

Arg Arg Arg Glu Leu Gly Ala Tyr Arg Ala Arg Lys Ser Phe Leu Asp
        355                 360                 365

Met Cys His Val Tyr Glu Glu Ile Asn Glu His Ile Thr Glu Asp Ala
    370                 375                 380

Leu Leu Ile Pro Gln Ile Glu Val Lys Trp Arg Asn Thr Ala Leu Arg
385                 390                 395                 400

Tyr Leu Ser Val Met Met Asn Ile Cys Asp Lys Lys Tyr Gly Arg Tyr
                405                 410                 415

Phe Asn Ala Val Glu Gln Thr Gly Ala Ala Pro Ser Gln Pro Ser Thr
            420                 425                 430

Ser Gly Leu Gly Ser Thr Ser Ala Gly Val Glu Gly Ala Gln Ala Ile
        435                 440                 445
```

-continued

```
Ser Val Pro Leu Arg Val Leu Glu Arg Ile Pro Ile Pro Tyr Gly Ala
    450                 455                 460

Pro Trp Asp Gln Pro Ser Thr Ser Gly Met Gly Gly Thr Ala Gly Thr
465                 470                 475                 480

Gly Ser Gln Gln Ala Ser His Ile Pro Pro His Asp Pro Gly Met Met
                485                 490                 495

Pro Tyr Ser Tyr Ala Gln Pro Ser Thr Leu Trp Asp Gln Pro Ser Thr
            500                 505                 510

Ser Gly Leu Gly Ser Ala Ala Gly Thr Gly Ser Gln Gln Ala Ser His
        515                 520                 525

Ile Pro Pro His Asp Pro Gly Met Met Pro Tyr Ser Tyr Ala Gln Pro
    530                 535                 540

Ser Thr Ser Trp Asp Gln Pro Ser Thr Ser Gly Leu Gly Ser Ala Ala
545                 550                 555                 560

Gly Met Gly Ser Gln Gln Ala Ser His Ile Pro Pro His Asp Pro Gly
                565                 570                 575

Met Met Pro Tyr Ser Tyr Ala Gln Pro Ser Thr Ser Trp Asp Gln Pro
            580                 585                 590

Ser Thr Ser Gly Leu Gly Ser Ala Ala Gly Met Gly Ser Gln Gln Ala
        595                 600                 605

Ser His Ile Pro Pro His Asp Pro Gly Met Met Pro Tyr Ser Tyr Ala
    610                 615                 620

Gln Pro Ser Thr Ser Trp Asp Gln Pro Ser Thr Ser Trp Asp Gln Pro
625                 630                 635                 640

Ser Thr Ser Gly Leu Gly Gly Thr Ala Gly Gln Gly Ala Gln Leu Val
                645                 650                 655

Pro Pro Pro Pro His Ile Leu Leu Arg Val Leu Glu Asn Val Pro Tyr
            660                 665                 670

Pro Ser Ser Gln Phe Ser Thr Ser Gly Leu Gly Gly Thr Ser Thr Gly
        675                 680                 685

Met Gly Arg Ser Gln Ala Pro Tyr Val Pro Pro Gln Asp Gln Gly Ile
    690                 695                 700

Met Pro Tyr Ser Trp Asp Gln Pro Ser Ala Ser Gly Leu Gly Gly Ala
705                 710                 715                 720

Ser Ser Thr Leu Glu Glu Ala Gln Val Ser Ser His Arg Pro Arg Thr
                725                 730                 735

Pro Ser Asp Asp Asp Ser Glu Pro Pro Ser Lys Gln Ala Arg Arg Ala
            740                 745                 750
```

COMPOUNDS AND METHODS FOR THE DIAGNOSIS AND TREATMENT OF EHRLICHIA INFECTION

CROSS-REFERENCE TO RELATED APPLICATIONS

Figure 1:
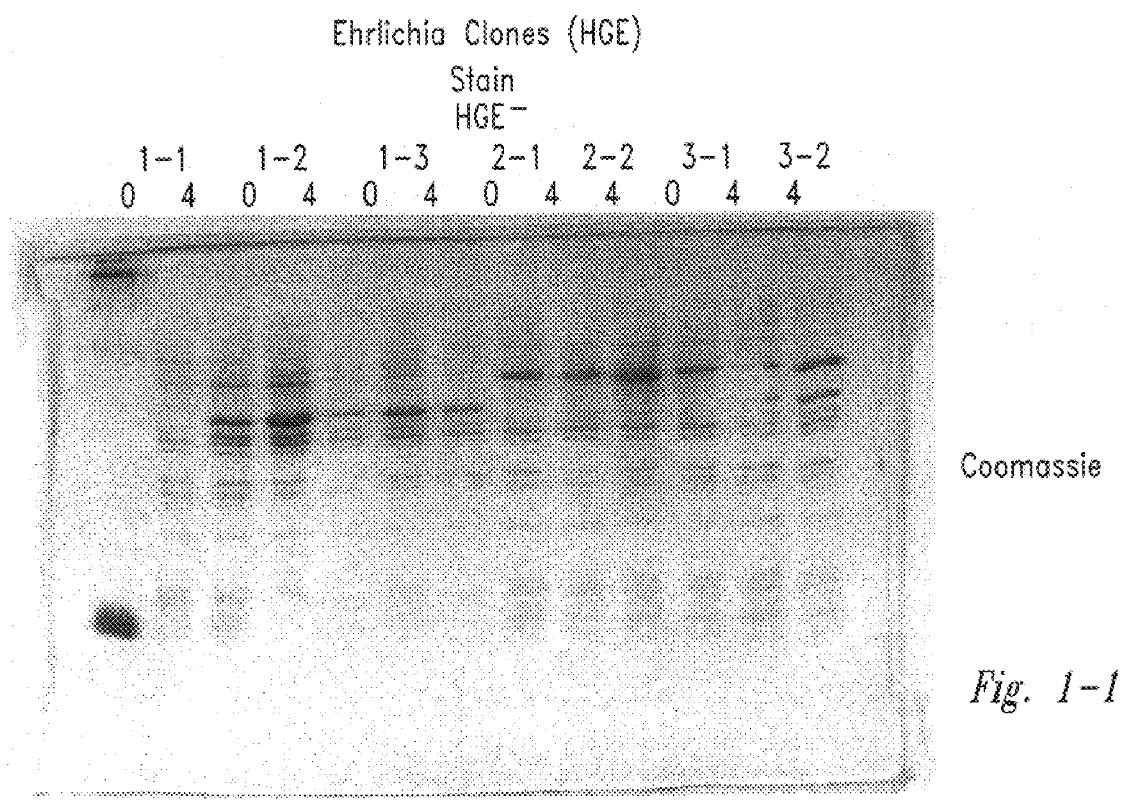
Figures 1, 2:
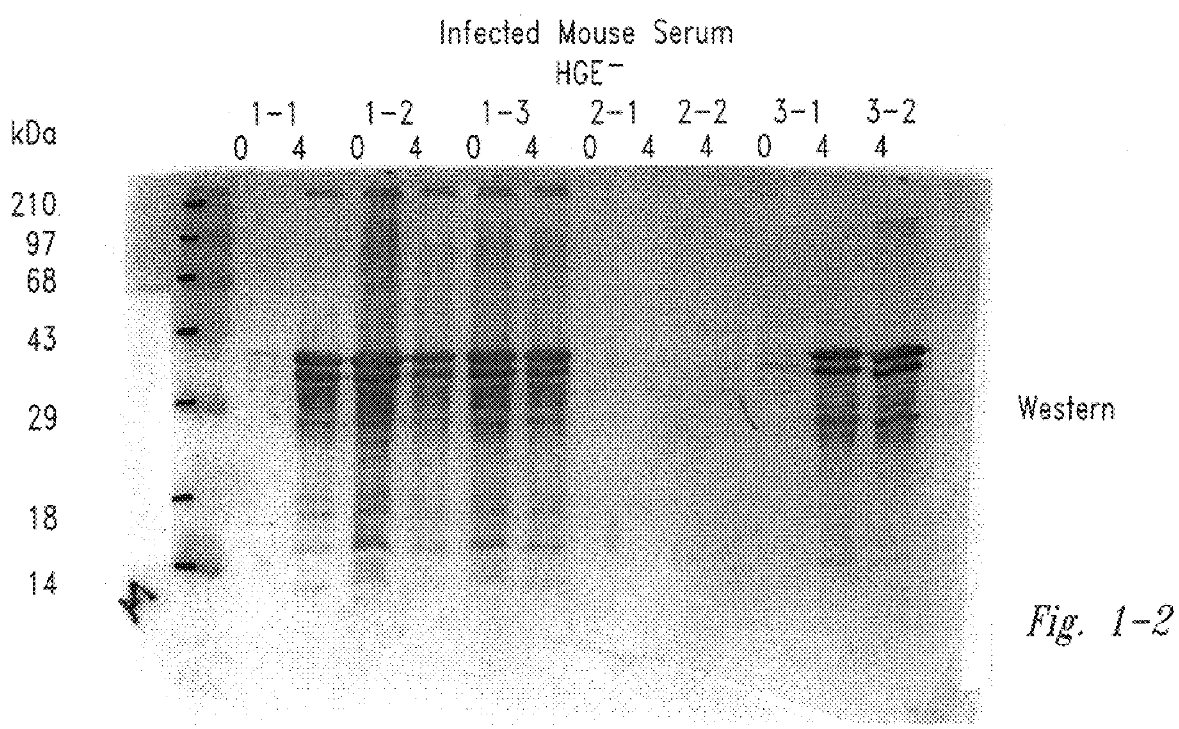
Figures 1, 2, 3:
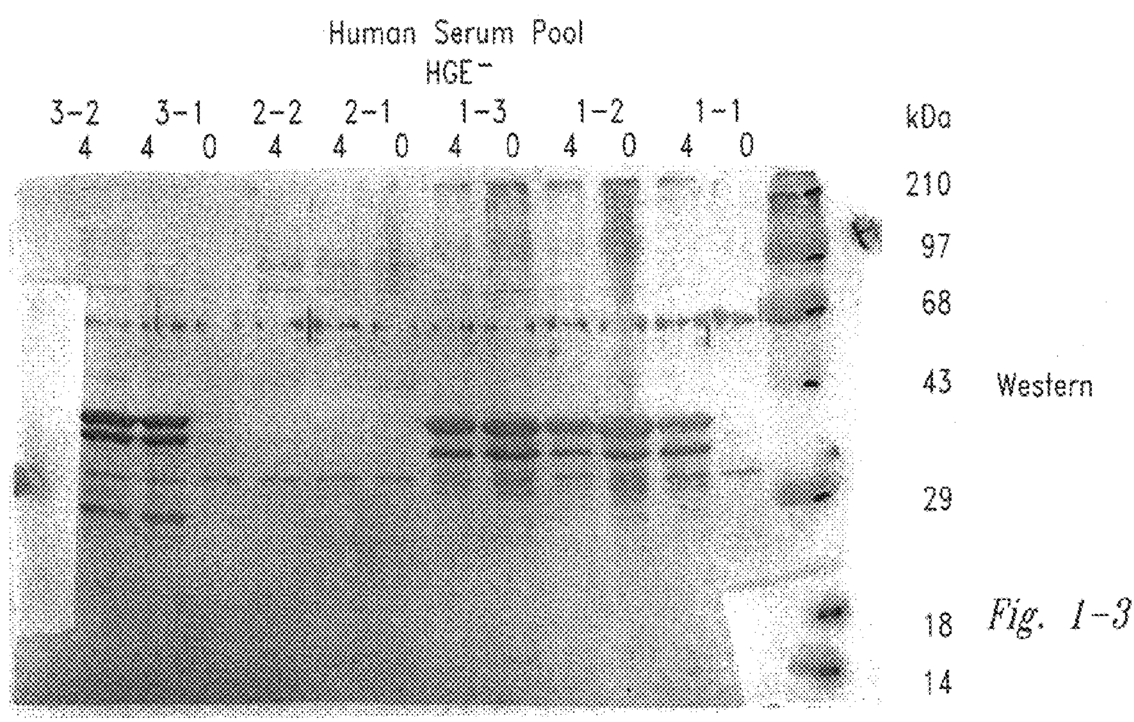

This application is related to U.S. patent application Ser. No. 09/566,617, filed May 8, 2000; U.S. patent application Ser. No. 09/295,028, filed Apr. 20, 1999; U.S. patent application Ser. No. 09/159,469, filed Sep. 23, 1998; U.S. patent application Ser. No. 09/106,582, filed Jun. 29, 1998; U.S. patent application Ser. No. 08/975,762; filed Nov. 20, 1997; and U.S. patent application Ser. No. 08/821,324, filed Mar. 21, 1997, each a CIP of the previous application and all pending; and PCT/US98/05695, filed Mar. 23, 1998, converted, and PCT/US99/14793, filed Jun. 29, 1999, published.

TECHNICAL FIELD

The present invention relates generally to the detection and treatment of Ehrlichia infection. In particular, the invention is related to polypeptides comprising an Ehrlichia antigen and the use of such polypeptides for the serodiagnosis and treatment of Human granulocytic ehrlichiosis (HGE).

BACKGROUND OF THE INVENTION

Human granulocytic ehrlichiosis (HGE) is an illness caused by a rodent bacterium which is generally transmitted to humans by the same tick that is responsible for the transmission of Lyme disease and babesiosis, thereby leading to the possibility of co-infection with Lyme disease, babesiosis and HGE from a single tick bite. The bacterium that causes HGE (referred to herein as *Ehrlichia phagocytophila*) is believed to be quite widespread in parts of the northeastern United States and has been detected in parts of Europe. While the number of reported cases of HGE infection is increasing rapidly, infection with Ehrlichia, including co-infection with Lyme disease, often remains undetected for extended periods of time. HGE is a potentially fatal disease, with the risk of death increasing if appropriate treatment is delayed beyond the first few days after symptoms occur. In contrast, deaths from Lyme disease and babesiosis are relatively rare.

The preferred treatments for HGE, Lyme disease and babesiosis are different, with penicillin's, such as doxycycline and amoxicillin, being most effective in treating Lyme disease, anti-malarial drugs being preferred for the treatment of babesiosis and tetracycline being preferred for the treatment of ehrlichiosis. Accurate and early diagnosis of Ehrlichia infection is thus critical but methods currently employed for diagnosis are problematic.

All three tick-borne illnesses share the same flu-like symptoms of muscle aches, fever, headaches and fatigue, thus making clinical diagnosis difficult. Microscopic analysis of blood samples may provide false-negative results when patients are first seen in the clinic. The only tests currently available for the diagnosis of HGE infection are indirect fluorescent antibody staining methods for total immunoglobulins to Ehrlichia causative agents and polymerase chain reaction (PCR) amplification tests. Such methods are time-consuming, labor-intensive and expensive. There thus remains a need in the art for improved methods for the detection of Ehrlichia infection, particularly as related to HGE. The present invention fulfills this need and further provides other related advantages.

SUMMARY OF THE INVENTION

The present invention provides compositions and methods for the diagnosis and treatment of Ehrlichia infection and, in particular, for the diagnosis and treatment of HGE. In one aspect, polypeptides are provided comprising an immunogenic portion of an Ehrlichia antigen, particularly one associated with HGE, or a variant of such an antigen. In one embodiment, the antigen comprises an amino acid sequence encoded by a polynucleotide selected from the group consisting of (a) SEQ ID NO: 1–7, 15–22, 31, 34, 36, 39–49, 86 and 88; (b) the complements of said sequences; (c) sequences that hybridize to a sequence of (a) or (b) under moderately stringent conditions; (d) sequences that have either 75% or 90% identity to a sequence of (a) or (b), determined as described below; and (e) degenerate variants of SEQ ID NO: 1–7, 15–22, 31, 34, 36, 39–49, 86 and 88.

In another aspect, the present invention provides an antigenic epitope of an Ehrlichia antigen comprising an amino acid sequence selected from the group consisting of sequences recited in SEQ ID NO: 30 and 51, together with polypeptides comprising at least two such antigenic epitopes, the epitopes being contiguous.

In a related aspect, polynucleotides encoding the above polypeptides, recombinant expression vectors comprising one or more such polynucleotides and host cells transformed or transfected with such expression vectors are also provided.

In another aspect, the present invention provides fusion proteins comprising either a first and a second inventive polypeptide, a first and a second inventive antigenic epitope, or, alternatively, an inventive polypeptide and an inventive antigenic epitope. In one specific embodiment, a fusion protein comprising an amino acid sequence provided in SEQ ID NO: 85 is provided.

In further aspects of the subject invention, methods and diagnostic kits are provided for detecting Ehrlichia infection in a patient. In one embodiment, the method comprises: (a) contacting a biological sample with at least one of the above polypeptides, antigenic epitopes or fusion proteins; and (b) detecting in the sample the presence of antibodies that bind to the polypeptide, antigenic epitope or fusion protein, thereby detecting Ehrlichia infection in the biological sample. Suitable biological samples include whole blood, sputum, serum, plasma, saliva, cerebrospinal fluid and urine. The diagnostic kits comprise one or more of the above polypeptides, antigenic epitopes or fusion proteins in combination with a detection reagent.

The present invention also provides methods for detecting Ehrlichia infection comprising: (a) obtaining a biological sample from a patient; (b) contacting the sample with at least two oligonucleotide primers in a polymerase chain reaction, at least one of the oligonucleotide primers being specific for a polynucleotide encoding the above polypeptides; and (c) detecting in the sample a polynucleotide that amplifies in the presence of the oligonucleotide primers. In one embodiment, the oligonucleotide primer comprises at least about 10 contiguous nucleotides of a polynucleotide encoding the above polypeptides.

In a further aspect, the present invention provides a method for detecting Ehrlichia infection in a patient comprising: (a) obtaining a biological sample from the patient; (b) contacting the sample with an oligonucleotide probe specific for a polynucleotide encoding the above polypeptides; and (c) detecting in the sample a polynucleotide that hybridizes to the oligonucleotide probe. In one embodiment, the oligonucleotide probe comprises at least about 15 contiguous nucleotides of a polynucleotide encoding one of the above polypeptides.

In yet another aspect, the present invention provides antibodies, both polyclonal and monoclonal, that bind to the polypeptides described above, as well as methods for their use in the detection of Ehrlichia infection.

In further aspects, the present invention provides methods for detecting either Ehrlichia infection, Lyme disease or *B. microti* infection in a patient. Such inventive methods comprise: (a) obtaining a biological sample from the patient; (b) contacting the sample with (i) at least one of the inventive polypeptides, antigenic epitopes or fusion proteins, (ii) a known Lyme disease antigen, and (iii) a known *B. microti* antigen; and (c) detecting in the sample the presence of antibodies that bind to the inventive polypeptide, antigenic epitope or fusion protein, the known Lyme disease antigen or the known *B. microti* antigen, thereby detecting either Ehrlichia infection, Lyme disease or *B. microti* infection in the patient.

Within other aspects, the present invention provides pharmaceutical compositions that comprise one or more of the above polypeptides or antigenic epitopes, or polynucleotides encoding such polypeptides, and a physiologically acceptable carrier. The invention also provides immunogenic compositions comprising one or more of the inventive polypeptides or antigenic epitopes and an immunostimulant, together with immunogenic compositions comprising one or more polynucleotides encoding such polypeptides and an immunostimulant.

In yet another aspect, methods are provided for inducing protective immunity in a patient, comprising administering to a patient an effective amount of one or more of the above pharmaceutical compositions or immunogenic compositions.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIG. 1 shows the results of Western blot analysis of representative Ehrlichia antigens of the present invention.

Figure 2A:
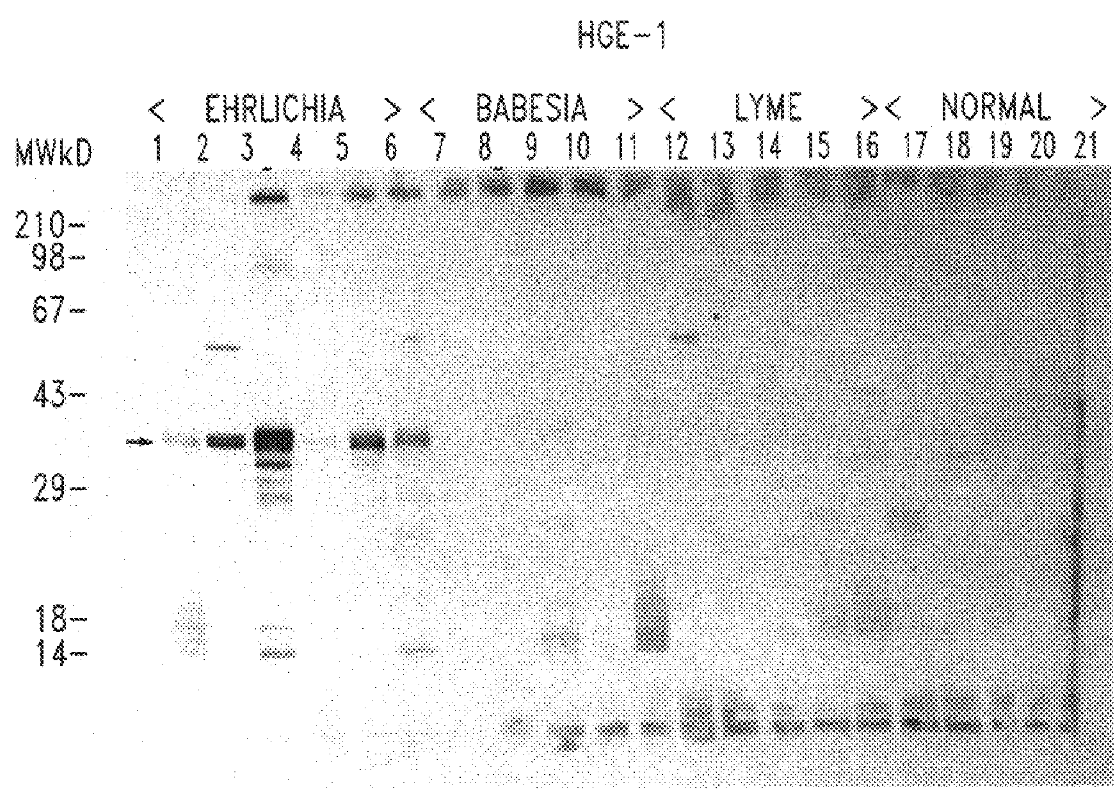

FIGS. 2A and B show the reactivity of purified recombinant Ehrlichia antigens HGE-1 and HGE-3, respectively, with sera from HGE-infected patients, babesiosis-infected patients, Lyme-disease infected patients and normal donors as determined by Western blot analysis.

SEQ ID NO: 1 is the determined DNA sequence of HGE-1.

SEQ ID NO: 2 is the determined DNA sequence of HGE-3.

SEQ ID NO: 3 is the determined DNA sequence of HGE-6.

SEQ ID NO: 4 is the determined 5' DNA sequence of HGE-7.

SEQ ID NO: 5 is the determined DNA sequence of HGE-12.

SEQ ID NO: 6 is the determined DNA sequence of HGE-23.

SEQ ID NO: 7 is the determined DNA sequence of HGE-24.

SEQ ID NO: 8 is the predicted protein sequence of HGE-1.

SEQ ID NO: 9 is the predicted protein sequence of HGE-3.

SEQ ID NO: 10 is the predicted protein sequence of HGE-6.

SEQ ID NO: 11 is the predicted protein sequence of HGE-7.

SEQ ID NO: 12 is the predicted protein sequence of HGE-12.

SEQ ID NO: 13 is the predicted protein sequence of HGE-23.

SEQ ID NO: 14 is the predicted protein sequence of HGE-24.

SEQ ID NO: 15 is the determined 5' DNA sequence of HGE-2.

SEQ ID NO: 16 is the determined DNA sequence of HGE-9.

SEQ ID NO: 17 is the determined DNA sequence of HGE-14.

SEQ ID NO: 18 is the determined 5' DNA sequence of HGE-15.

SEQ ID NO: 19 is the determined 5' DNA sequence of HGE-16.

SEQ ID NO: 20 is the determined 5' DNA sequence of HGE-17.

SEQ ID NO: 21 is the determined 5' DNA sequence of HGE-18.

SEQ ID NO: 22 is the determined 5' DNA sequence of HGE-25.

SEQ ID NO: 23 is the predicted protein sequence of HGE-2.

SEQ ID NO: 24 is the predicted protein sequence of HGE-9.

SEQ ID NO: 25 is the predicted protein sequence of HGE-14.

SEQ ID NO: 26 is the predicted protein sequence of HGE-18.

SEQ ID NO: 27 is the predicted protein sequence from the reverse complement of HGE-14.

SEQ ID NO: 28 is the predicted protein sequence from the reverse complement of HGE-15.

SEQ ID NO: 29 is the predicted protein sequence from the reverse complement of HGE-18.

SEQ ID NO: 30 is a 41 amino acid repeat sequence from HGE-14.

SEQ ID NO: 31 is the determined DNA sequence of HGE-11.

SEQ ID NO: 32 is the predicted protein sequence of HGE-11.

SEQ ID NO: 33 is the predicted protein sequence from the reverse complement of HGE-11.

SEQ ID NO: 34 is the determined DNA sequence of HGE-13.

SEQ ID NO: 35 is the predicted protein sequence of HGE-13.

SEQ ID NO: 36 is the determined DNA sequence of HGE-8.

SEQ ID NO: 37 is the predicted protein sequence of HGE-8.

SEQ ID NO: 38 is the predicted protein sequence from the reverse complement of HGE-8.

SEQ ID NO: 39 is the extended DNA sequence of HGE-2.

SEQ ID NO: 40 is the extended DNA sequence of HGE-7.

SEQ ID NO: 41 is the extended DNA sequence of HGE-8.

SEQ ID NO: 42 is the extended DNA sequence of HGE-11.

SEQ ID NO: 43 is the extended DNA sequence of HGE-14.

SEQ ID NO: 44 is the extended DNA sequence of HGE-15.

SEQ ID NO: 45 is the extended DNA sequence of HGE-16.

SEQ ID NO: 46 is the extended DNA sequence of HGE-18.

SEQ ID NO: 47 is the extended DNA sequence of HGE-23.

SEQ ID NO: 48 is the extended DNA sequence of HGE-25.

SEQ ID NO: 49 is the determined 3' DNA sequence of HGE-17.

SEQ ID NO: 50 is the extended predicted protein sequence of HGE-2.

SEQ ID NO: 51 is the amino acid repeat sequence of HGE-2.

SEQ ID NO: 52 is a second predicted protein sequence of HGE-7.

SEQ ID NO: 53 is a third predicted protein sequence of HGE-7.

SEQ ID NO: 54 is a second predicted protein sequence of HGE-8.

SEQ ID NO: 55 is a third predicted protein sequence of HGE-8.

SEQ ID NO: 56 is a fourth predicted protein sequence of HGE-8.

SEQ ID NO: 57 is a fifth predicted protein sequence of HGE-8.

SEQ ID NO: 58 is a second predicted protein sequence of HGE-11.

SEQ ID NO: 59 is a third predicted protein sequence of HGE-11.

SEQ ID NO: 60 is a second predicted protein sequence from the reverse complement of HGE-14.

SEQ ID NO: 61 is a third predicted protein sequence from the reverse complement of HGE-14.

SEQ ID NO: 62 is a first predicted protein sequence of HGE-15.

SEQ ID NO: 63 is a second predicted protein sequence of HGE-15.

SEQ ID NO: 64 is a second predicted protein sequence from the reverse complement of HGE-15.

SEQ ID NO: 65 is the predicted protein sequence of HGE-16.

SEQ ID NO: 66 is a first predicted protein sequence from the reverse complement of HGE-17.

SEQ ID NO: 67 is a second predicted protein sequence from the reverse complement of HGE-17.

SEQ ID NO: 68 is a second predicted protein sequence from the reverse complement of HGE-18.

SEQ ID NO: 69 is a third predicted protein sequence from the reverse complement of HGE-18.

SEQ ID NO: 70 is a fourth predicted protein sequence from the reverse complement of HGE-18.

SEQ ID NO: 71 is a second predicted protein sequence of HGE-23.

SEQ ID NO: 72 is a third predicted protein sequence of HGE-23.

SEQ ID NO: 73 is the predicted protein sequence of HGE-25.

SEQ ID NO: 74–79 are primers used in the preparation of a fusion protein containing HGE-9, HGE-3 and HGE-1.

SEQ ID NO: 80–83 are primers used in the preparation of a fusion protein containing HGE-3 and HGE-1 (referred to as ErF-1).

SEQ ID NO: 84 is the DNA sequence of the fusion ErF-1.

SEQ ID NO: 85 is the amino acid sequence of the fusion protein ErF-1.

SEQ ID NO: 86 is the full-length cDNA sequence for HGE-17.

SEQ ID NO: 87 is the amino acid sequence for HGE-17.

SEQ ID NO: 88 is a corrected cDNA sequence for HGE-14.

SEQ ID NO: 89 is the amino acid encoded by SEQ ID NO: 88.

DETAILED DESCRIPTION OF THE INVENTION

As noted above, the present invention is generally directed to compositions and methods for the diagnosis and treatment of Ehrlichia infection, in particular HGE. In one aspect, the compositions of the subject invention include polypeptides that comprise at least one immunogenic portion of an Ehrlichia antigen, or a variant of such an antigen.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native Ehrlichia antigen or may be heterologous, and such sequences may (but need not) be immunogenic.

An "immunogenic portion" of an antigen is a portion that is capable of reacting with sera obtained from an Ehrlichia-infected individual (i.e., generates an absorbance reading with sera from infected individuals that is at least three standard deviations above the absorbance obtained with sera from uninfected individuals, in a representative ELISA assay described herein). Such immunogenic portions generally comprise at least about 5 amino acid residues, more preferably at least about 10, and most preferably at least about 20 amino acid residues. Methods for preparing and identifying immunogenic portions of antigens of known sequence are well known in the art and include those summarized in Paul, *Fundamental Immunology*, 3rd ed., Raven Press, 1993, pp. 243–247. Polypeptides comprising at least an immunogenic portion of one or more Ehrlichia antigens as described herein may generally be used, alone or in combination, to detect HGE infection in a patient.

The compositions and methods of the present invention also encompass variants of the above polypeptides and polynucleotides. Such variants include, but are not limited to, naturally occurring allelic variants of the inventive sequences.

A polypeptide "variant," as used herein, is a polypeptide that differs from a native protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% identity (determined as described below) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polynucleotides may comprise a native sequence (i.e., an endogenous sequence that encodes a protein or a portion thereof) or may comprise a variant of such a sequence, or a biological or antigenic functional equivalent of such a sequence. Polynucleotide variants may contain one or more substitutions, additions, deletions and/or insertions, as further described below, preferably such that the immunogenicity of the encoded polypeptide, relative to the native protein, is not diminished. The effect on the immunogenicity of the encoded polypeptide may generally be assessed as described herein. As used herein, the term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Preferred examples of algorithms that are suitable for determining percentage sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by to yield the percentage of sequence identity.

The present invention thus encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% sequence identity compared to a polynucleotide or polypeptide sequence of this invention using the methods described herein, (e.g., BLAST analysis using standard parameters, as described above). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In general, Ehrlichia antigens, and polynucleotides encoding such antigens, may be prepared using any of a variety of procedures. For example, polynucleotides encoding Ehrlichia antigens may be isolated from an Ehrlichia genomic or cDNA expression library by screening with sera from HGE-infected individuals as described below in Example 1, and sequenced using techniques well known to those of skill in the art. Polynucleotides encoding Ehrlichia antigens may also be isolated by screening an appropriate Ehrlichia expression library with anti-sera (e.g., rabbit) raised specifically against Ehrlichia antigens.

Antigens may be induced from such clones and evaluated for a desired property, such as the ability to react with sera obtained from an HGE-infected individual as described herein. Alternatively, antigens may be produced recombinantly, as described below, by inserting a polynucleotide that encodes the antigen into an expression vector and expressing the antigen in an appropriate host. Antigens may be sequenced, either partially or fully, using, for example, traditional Edman chemistry. See Edman and Berg, *Eur. J. Biochem.* 80:116–132, 1967.

Polynucleotides encoding antigens may also be obtained by screening an appropriate Ehrlichia cDNA or genomic DNA library for polynucleotides that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

Immunogenic portions of Ehrlichia antigens may be prepared and identified using well known techniques, such as those summarized in Paul, *Fundamental Immunology*, 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of an Ehrlichia antigen generates at least about 20%, and preferably about 100%, of the signal induced by the full length antigen in a model ELISA as described herein.

Portions and other variants of Ehrlichia antigens may be generated by synthetic or recombinant means. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a polynucleotide encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line, such as COS or CHO. The polynucleotides expressed in this manner may encode naturally occurring antigens, portions of naturally occurring antigens, or other variants thereof.

In another aspect, the present invention provides antigenic epitopes of an Ehrlichia antigen or epitope repeat sequences, as well as polypeptides comprising at least two such contiguous antigenic epitopes. As used herein, an "epitope" is a portion of an antigen that reacts with sera from Ehrlichia-infected individuals (i.e. an epitope is specifically bound by one or more antibodies present in such sera). As discussed above, epitopes of the antigens described in the present application may be generally identified using techniques well known to those of skill in the art.

In specific embodiments, antigenic epitopes of the present invention comprise an amino acid sequence selected from the group consisting of sequence recited in SEQ ID NO: 30 and 51. As discussed in more detail below, antigenic epitopes provided herein may be employed in the diagnosis and treatment of Ehrlichia infection, either alone or in combination with other Ehrlichia antigens or antigenic epitopes. Antigenic epitopes and polypeptides comprising such epitopes may be prepared by synthetic means, as described generally above and in detail in Example 3.

In general, regardless of the method of preparation, the polypeptides and antigenic epitopes disclosed herein are prepared in an isolated, substantially pure, form. Preferably, the polypeptides and antigenic epitopes are at least about 80% pure, more preferably at least about 90% pure and most preferably at least about 99% pure.

In a further aspect, the present invention provides fusion proteins comprising either a first and a second inventive polypeptide, a first and a second inventive antigenic epitope, or an inventive polypeptide and an antigenic epitope of the present invention, together with variants of such fusion proteins. The fusion proteins of the present invention may also include a linker peptide between the polypeptides or antigenic epitopes.

A polynucleotide encoding a fusion protein of the present invention may be constructed using known recombinant DNA techniques to assemble separate DNA sequences encoding, for example, the first and second polypeptides, into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. As an alternative to the use of a peptide linker sequence (when desired), one can utilize non-essential N-terminal amino acid regions (when present) on the first and second polypeptides to separate the functional domains and prevent steric hindrance.

In another aspect, the present invention provides methods for using the polypeptides, fusion proteins and antigenic epitopes described above to diagnose Ehrlichia infection, in particular HGE. In this aspect, methods are provided for detecting Ehrlichia infection in a biological sample, using one or more of the above polypeptides, fusion proteins and antigenic epitopes, either alone or in combination. For clarity, the term "polypeptide" will be used when describing specific embodiments of the inventive diagnostic methods. However, it will be clear to one of skill in the art that the antigenic epitopes and fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to Ehrlichia antigens which may be indicative of HGE.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with HGE. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the inmmobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Ehrlichia antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for HGE. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a 10 signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for HGE.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-Ehrlichia antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 μg, and more preferably from about 50 ng to about 500 ng. Such tests can typically be performed with a very small amount (e.g., one drop) of patient serum or blood.

Of course, numerous other assay protocols exist that are suitable for use with the polypeptides and antigenic epitopes of the present invention. The above descriptions are intended to be exemplary only.

The inventive polypeptides may be employed in combination with known Lyme disease and/or *B. microti* antigens to diagnose the presence of either Ehrlichia infection, Lyme disease and/or *B. microti* infection, using either the assay formats described herein or other assay protocols. One example of an alternative assay protocol which may be usefully employed in such methods is a Western blot, wherein the proteins present in a biological sample are separated on a gel, prior to exposure to a binding agent. Such techniques are well known to those of skill in the art. Lyme disease antigens which may be usefully employed in such methods are well known to those of skill in the art and include, for example, those described by Magnarelli, L. et al. (J. Clin. Microbiol., 1996 34:237–240), Magnarelli, L. (Rheum. Dis. Clin. North Am., 1989, 15:735–745) and Cutler, S. J. (J. Clin. Pathol., 1989, 42:869–871). *B. microti* antigens which may be usefully employed in the inventive methods include those described in U.S. patent application Ser. No. 08/845,258, filed Apr. 24, 1997, the disclosure of which is hereby incorporated by reference.

In yet another aspect, the present invention provides antibodies to the polypeptides and antigenic epitopes of the present invention. Antibodies may be prepared by any of a variety of techniques known to those of ordinary skill in the art. See, e.g., Harlow and Lane, *Antibodies: A Laboratory Manual*, Cold Spring Harbor Laboratory, Cold Spring Harbor, N.Y., 1988. In one such technique, an immunogen comprising the antigenic polypeptide or epitope is initially injected into any of a wide variety of mammals (e.g., mice, rats, rabbits, sheep and goats). The polypeptides and antigenic epitopes of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide coupled to a suitable solid support.

Monoclonal antibodies specific for the antigenic polypeptide or epitope of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and mycloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of Ehrlichia antigens using assays similar to those detailed above and other techniques well known to those of skill in the art, thereby providing a method for detecting Ehrlichia infection in a patient.

The presence of HGE infection may also, or alternatively, be detected based on the level of mRNA encoding an HGE-specific protein in a biological sample, such as whole blood, serum, plasma, saliva, cerebrospinal fluid and urine. For example, at least two oligonucleotide primers may be employed in a polymerase chain reaction (PCR) based assay to amplify a portion of an HGE-specific polynucleotide derived from a biological sample, wherein at least one of the oligonucleotide primers is specific for (i.e., hybridizes to) a polynucleotide encoding the HGE protein. The amplified polynucleotide is then separated and detected using techniques well known in the art, such as gel electrophoresis. Similarly, oligonucleotide probes that specifically hybridize to a polynucleotide encoding an HGE protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a sequence that is complementary to a portion of a polynucleotide encoding an HGE protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule that is complementary to a polynucleotide disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an uninfected individual. The amplification reaction may be performed on several dilutions of cDNA spanning two orders of magnitude. A two-fold or greater increase in expression in several dilutions of the test patient sample as compared to the same dilutions of the non-infected sample is typically considered positive.

In another aspect, the present invention provides methods for using one or more of the above polypeptides, antigenic epitopes or fusion proteins (or polynucleotides encoding such polypeptides) to induce protective immunity against Ehrlichia infection in a patient. As used herein, a "patient" refers to any warm-blooded animal, preferably a human. A patient may be afflicted with a disease, or may be free of detectable disease and/or infection. In other words, protective immunity may be induced to prevent or treat Ehrlichia infection, specifically HGE.

In this aspect, the polypeptide, antigenic epitope, fusion protein or polynucleotide is generally present within a pharmaceutical composition or a vaccine (also referred to as an immunogenic composition). Pharmaceutical compositions may comprise one or more polypeptides, each of which may contain one or more of the above sequences (or variants thereof), and a physiologically acceptable carrier. Immunogenic compositions may comprise one or more of the above polypeptides and an immunostimulant, such as an adjuvant or a liposome (into which the polypeptide is incorporated). Such pharmaceutical and immunogenic compositions may also contain other Ehrlichia antigens, either incorporated into a combination polypeptide or present as a separate polypeptide.

Alternatively, an immunogenic composition may contain DNA encoding one or more polypeptides, antigenic epitopes or fusion proteins as described above, such that the polypeptide is generated in situ. In such immunogenic compositions, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine, or immunogenic composition, as described above may be administered simultaneously with or sequentially to either a polypeptide of the present invention or a known Ehrlichia antigen. For example, administration of DNA encoding a polypeptide of the present invention, either "naked" or in a delivery system as described above, may be followed by administration of an antigen in order to enhance the protective immune effect of the immunogenic composition.

Routes and frequency of administration, as well as dosage, will vary from individual to individual. In general, the pharmaceutical compositions and immunogenic compositions may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from HGE for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 mL to about 5 mL.

While any suitable carrier known to those of ordinary skill in the art may be employed in the compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the immunogenic compositions of this invention to enhance the immune response. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants. In certain embodiments, the inventive immunogenic compositions include an adjuvant capable of eliciting a predominantly Th-1 type response. Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corp. (Hamilton, Mont.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555 and WP 99/33488. Immunostimulatory DNA sequences are also described, for example, by Sato et al., *Science* 273:352, 1996. Another preferred adjuvant is a saponin, preferably QS21 (Aquila, United States), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, California, United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

The following Examples are offered by way of illustration and not by way of limitation.

EXAMPLE 1

Isolation of DNA Sequences Encoding Ehrlichia Antigens

This example illustrates the preparation of DNA sequences encoding

Ehrlichia antigens by screening an Ehrlichia genomic expression library with sera obtained from mice infected with the HGE agent.

Ehrlichia genomic DNA was isolated from infected human HL60 cells and sheared by sonication. The resulting randomly sheared DNA was used to construct an Ehrlichia genomic expression library (approximately 0.5–4.0 kbp inserts) with EcoRI adaptors and a Lambda ZAP II/EcoRI/CIAP vector (Stratagene, La Jolla, Calif.). The unamplified library ($6.5\times10^6$/ml) was screened with an *E. coli* lysate-absorbed Ehrlichia mouse serum pool, as described in Sambrook et al., *Molecular Cloning: A Laboratory Manual*, Cold Spring Harbor Laboratories, Cold Spring Harbor, N.Y., 1989. Positive plaques were visualized and purified with goat-anti-mouse alkaline phosphatase. Phagemid from the plaques was rescued and DNA sequence for positive clones was obtained using forward, reverse, and specific internal primers on a Perkin Elmer/Applied Biosystems Inc. Automated Sequencer Model 373A (Foster City, Calif.).

Of the eighteen antigens isolated using this technique, seven (hereinafter referred to as HGE-1, HGE-3, HGE-6, HGE-7, HGE-12, HGE-23 and HGE-24) were found to be related. The determined DNA sequences for HGE-1, HGE-3, HGE-6, HGE-12, HGE-23 and HGE-24 are shown in SEQ ID NO: 1–3 and 5–7, respectively, with the 5' DNA sequence for HGE-7 being provided in SEQ ID NO: 4. The deduced amino acid sequences for HGE-1, HGE-3, HGE-6, HGE-7, HGE-12, HGE-23 and HGE-24 are provided in SEQ ID NO: 8–14, respectively. Comparison of these sequences with known sequences in the gene bank using the DNA STAR system, revealed some degree of homology to the *Anaplasma marginale* major surface protein.

Of the remaining eleven isolated antigens, no significant homologies were found to HGE-2, HGE-9, HGE-14, HGE-15, HGE-16, HGE-17, HGE-18 and HGE-25. The determined full-length cDNA sequences for HGE-9 and HGE-14 are provided in SEQ ID NO: 16 and 17, respectively, with the determined 5' DNA sequences for HGE-2, HGE-15, HGE-16, HGE-17, HGE-18 and HGE-25 being shown in SEQ ID NO: 15, and 18–22, respectively. The corresponding predicted amino acid sequences for HGE-2, HGE-9, HGE-14 and HGE-18 are provided in SEQ ID NO: 23–26, respectively. The reverse complements of HGE-14, HGE-15 and HGE-18 were found to contain open reading frames which encode the amino acid sequences shown in SEQ ID NO: 27, 28 and 29, respectively. The predicted amino acid sequence from the reverse complement strand of HGE-14 (SEQ ID NO: 27) was found to contain a 41 amino acid repeat, provided in SEQ ID NO: 30. The full-length cDNA sequence for HGE-14 provided in SEQ ID NO: 17 was subsequently found to contain minor sequencing errors. A corrected full-length cDNA sequence for HGE-14 is provided in SEQ ID NO: 88, with the corresponding amino acid sequence being provided in SEQ ID NO: 89. The cDNA sequence of SEQ ID NO: 88 differs from that of SEQ ID NO: 17 by 2 nucleotides.

The determined DNA sequence for the isolated antigen HGE-11 is provided in SEQ ID NO: 31, with the predicted amino acid sequences being provided in SEQ ID NO: 32 and 33. Comparison of these sequences with known sequence in the gene bank, revealed some homology between the amino acid sequence of SEQ ID NO: 32 and that of bacterial DNA-directed RNA polymerase beta subunit rpoB (Monastyrskaya, G. S. et al., 1990*, Bioorg. Khim.* 6:1106–1109), and further between the amino acid sequence of SEQ ID NO: 33 and that of bacterial DNA-directed RNA polymerase beta' subunit rpoC (Borodin A. M. et al, 1988 *Bioorg. Khim*. 14:1179–1182).

The determined 5' DNA sequence for the antigen HGE-13 is provided in SEQ ID NO: 34. The opposite strand for HGE-13 was found to contain an open reading frame which encodes the amino acid sequence provided in SEQ ID NO: 35. This sequence was found to have some homology to bacterial 2,3-biphosphoglycerate-independent phosphoglycerate mutase (Leyva-Vazquez, M. A. and Setlow, P., 1994 *J. Bacteriol.* 176:3903–3910).

The determined partial nucleotide sequence for the isolated antigen HGE-8 (SEQ ID NO: 36) was found to include, on the reverse complement of the 5' end, two open reading frames encoding the amino acid sequences provided in SEQ ID NO: 37 and 38. The amino acid sequences of SEQ ID NO: 37 and 38 were found to show some homology to prokaryotic and eukaryotic dihydrolipamide succinyltransferase (Fleischmann R. D. et al, 1995 Science 269:496–512) and methionine aminopeptidase (Chang, Y. H., 1992 *J. Biol. Chem*. 267:8007–8011), respectively.

Subsequent studies resulted in the determination of extended DNA sequences for HGE-2, HGE-7, HGE-8, HGE-11, HGE-14, HGE-15, HGE-16, HGE-18, HGE-23 and HGE-25 (SEQ ID NO: 39–48, respectively) and in the determination of the 3' sequence for HGE-17 (SEQ ID NO: 49). The complement of the extended HGE-2 DNA sequence was found to contain an open reading frame which encodes for a 61.4 kDa protein (SEQ ID NO: 50) having three copies of a 125 amino acid repeat (SEQ ID NO: 51). The extended DNA sequence of HGE-7 was found to contain two open reading frames encoding for the amino acid sequences shown in SEQ ID NO: 52 and 53. The extended DNA sequence of HGE-8 was found to contain four open reading frames encoding the proteins of SEQ ID NO: 54–57. Each of these four proteins was found to show some similarity to known proteins, however, to the best of the inventors' knowledge, none have previously been identified in Ehrlichia.

The extended DNA sequence of HGE-11 was found to contain two open reading frames encoding the amino acid sequences provided in SEQ ID NO: 58 and 59. These two proteins were found to show some homology to the bacterial DNA-directed RNA polymerase beta subunits rpoB and rpo C, respectively. The reverse complement of the extended DNA sequence of HGE-14 was found to contain two open reading frames, with one encoding the amino acid sequence provided in SEQ ID NO: 60. The second open reading frame encodes the amino acid sequence provided in SEQ ID NO: 61, which contains the amino acid sequence provided in SEQ ID NO: 27. The extended DNA sequence of HGE-15 was found to contain two open reading frames encoding for the sequences provided in SEQ ID NO: 62 and 63, with a third open reading frame encoding the sequence of SEQ ID NO: 64 being located on the reverse complement. The extended DNA sequence of HGE-16 was found to contain an open reading frame encoding the amino acid sequence of SEQ ID NO: 65. The reverse complement of the 3' DNA sequence of HGE-17 was found to contain two open reading frames encoding the amino acid sequences of SEQ ID NO: 66 and 67.

The reverse complement of the extended DNA sequence of HGE-18 was found to contain three open reading frames encoding the amino acid sequences of SEQ ID NO: 68–70. The sequence of SEQ ID NO: 70 was found to show some homology to bacterial DNA helicase. The extended DNA sequence of HGE-23 was found to contain two open reading frames encoding for the sequences of SEQ ID NO:71 and 72. Both of these sequences, together with those of SEQ ID NO:52 and 53, were found to share some homology with the Anaplasma marginale major surface protein. The predicted amino acid sequence encoded by the extended DNA sequence of HGE-25 is provided in SEQ ID NO:73. This sequence was found to show some similarity to that of SEQ ID NO:64 (HGE-15). No significant homologies were found to the amino acid sequences of HGE-2, HGE-14, HGE-15, HGE-16, HGE-17 and HGE-25 (SEQ ID NO: 50, 60–67 and 73).

Using standard full-length cloning techniques, the full-length cDNA sequence for HGE-17 was isolated. This sequence is provided in SEQ ID NO: 86, with the corresponding amino acid sequence being provided in SEQ ID NO: 87. These sequences were found to show some homology to the known sequences for ankyrin.

EXAMPLE 2

Use of Representative Antigens for Serodiagnosis of HGE Infection

The diagnostic properties of representative Ehrlichia antigens were determined by Western blot analysis as follows.

Antigens were induced as pBluescript SK-constructs (Stratagene), with 2 mM IPTG for three hours (T3), after which the resulting proteins from time 0 (T0) and T3 were separated by SDS-PAGE on 15% gels. Separated proteins were then transferred to nitrocellulose and blocked for 1 hr in 1% BSA in 0.1% Tween 20™/PBS. Blots were then washed 3 times in 0.1% Tween 20™/PBS and incubated with either an HGE patient serum pool (1:200) or an Ehrlichia-infected mouse serum pool for a period of 2 hours. After washing in 0.1% Tween 20™/PBS 3 times, blots were incubated with a second antibody (goat-anti-human IgG conjugated to alkaline phosphatase (AP) or goat-anti-mouse IgG-AP, respectively) for 1 hour. Immunocomplexes were visualized with NBT/BCIP (Gibco BRL) after washing with Tween 20™/PBS three times and AP buffer (100 mM Tris-HCl, 100 mM NaCl, 5 mM $MgCl_2$, pH 9.5) two times.

As shown in FIG. 1, resulting bands of reactivity with serum antibody were seen at 37 kDa for HGE-1 and HGE-3 for both the mouse serum pool and the human serum pool. Protein size standards, in kDa (Gibco BRL, Gaithersburg, Md.), are shown to the left of the blots.

Western blots were performed on partially purified HGE-1 and HGE-3 recombinant antigen with a series of patient sera from HGE patients, patients with Lyme disease, babesiosis patients or from normal donors. Specifically, purified antigen (4 μg) was separated by SDS-PAGE on 12% gels. Protein was then transferred to nitrocellulose membrane for immunoblot analysis. The membrane was first blocked with PBS containing 1% Tween 20™ for 2 hours. Membranes were then cut into strips and incubated with individual sera (1/500) for two hours. The strips were washed 3 times in PBS/0.1% Tween 20™ containing 0.5 M NaCl prior to incubating with Protein A-horseradish peroxidase conjugate (1/20,000) in PBS/0.1% Tween 20™/0.5 M NaCl for 45 minutes. After further washing three times in PBS/0.1% Tween 20™/0.5 M NaCl, ECL chemiluminescent substrate (Amersham, Arlington Heights, Ill.) was added for 1 min. Strips were then reassembled and exposed to Hyperfilm ECL (Amersham) for 5–30 seconds.

Figure 2B:
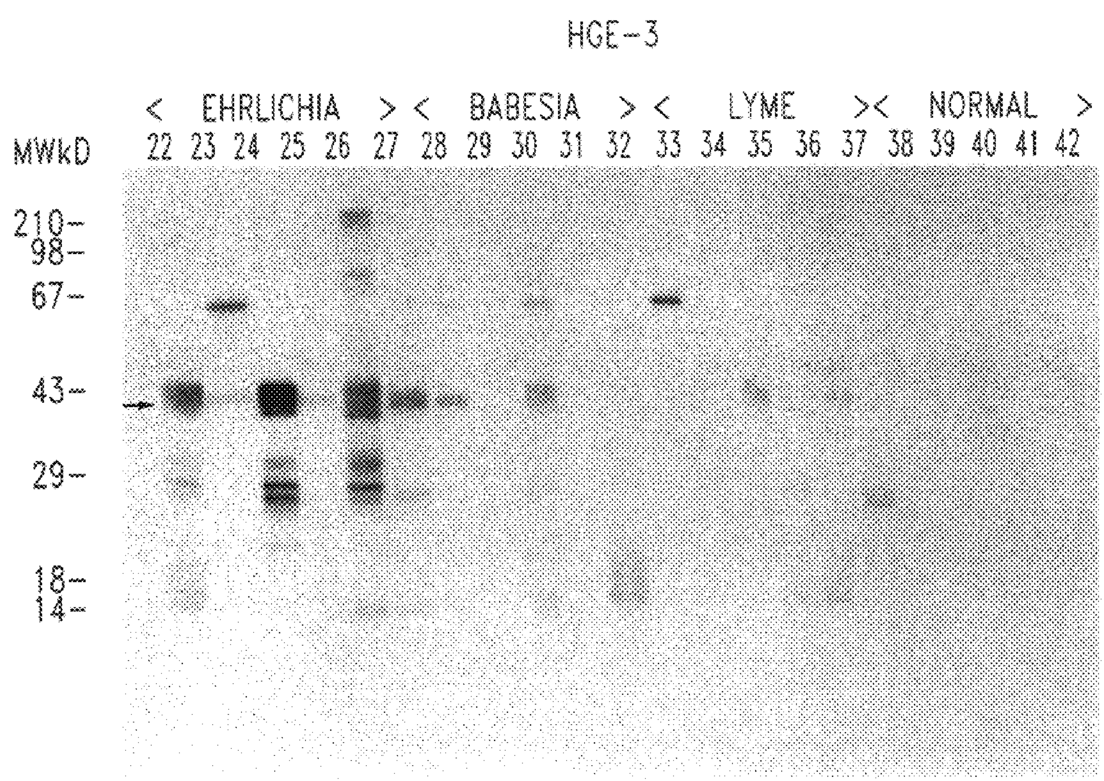

Lanes 1–6 of FIG. 2A show the reactivity of purified recombinant HGE-1 (MW 37 kD) with sera from six HGE-infected patients, of which all were clearly positive. In contrast, no immunoreactivity with HGE-1 was seen with sera from patients with either babesiosis (lanes 7–11), or Lyme disease (lanes 12–16), or with sera from normal individuals (lanes 17–21). As shown in FIG. 2B, HGE-3 (MW 37 kD) was found to react with sera from all six HGE patients (lanes 22–27), while cross-reactivity was seen with sera from two of the five babesiosis patients and weak cross-reactivity was seen with sera from two of the five Lyme disease patients. This apparent cross-reactivity may represent the ability of the antigen HGE-3 to detect low antibody titer in patients co-infected with HGE. No immunoreactivity of HGE-3 was seen with sera from normal patients.

Table 1 provides representative data from studies of the reactivity of HGE-1, HGE-3 and HGE-9 with both IgG and IgM in sera from patients with acute (A) or convalescent (C) HGE, determined as described above. The antibody titer for each patient, as determined by immunofluorescence, is also provided.

TABLE 1

| Patient | HGE | IgG | | | IgM | | |
|---|---|---|---|---|---|---|---|
| ID | titer | HGE-1 | HGE-3 | HGE-9 | HGE-1 | HGE-3 | HGE-9 |
| 1 (A) | 128 | 0.346 | 0.154 | 0.423 | 0.067 | 0.028 | 0.022 |
| 2 (A) | 1024 | 1.539 | 1.839 | 0.893 | 2.75 | 3.256 | 1.795 |
| 3 (A) | <16 | 0.412 | 0.16 | 0.659 | 0.043 | 0.088 | 0.047 |
| 4 (A) | <16 | 0.436 | 0.072 | 0.472 | 0.017 | 0.032 | 0.064 |
| 5 (C) | 256 | 0.322 | 0.595 | 0.694 | 0.229 | 0.345 | 0.269 |

TABLE 1-continued

| Patient | HGE | IgG | | | IgM | | |
|---|---|---|---|---|---|---|---|
| ID | titer | HGE-1 | HGE-3 | HGE-9 | HGE-1 | HGE-3 | HGE-9 |
| 6 (A) | 512 | 1.509 | 2.042 | 1.241 | 0.721 | 0.695 | 0.313 |
| 7 (C) | 512 | 0.508 | 1.019 | 0.777 | 0.45 | 0.777 | 0.29 |
| 8 (C) | 128 | 0.635 | 0.979 | 1.684 | 0.729 | 2.079 | 0.729 |
| 9 (C) | 256 | 0.408 | 0.74 | 0.679 | 0.052 | 0.11 | 0.062 |
| 10 (A) | 64 | 0.579 | 0.133 | 0.239 | −0.002 | 0.015 | 0.126 |
| 11 (A) | 256 | 0.13 | 0.066 | 1.002 | −0.018 | 0.003 | 0.047 |
| 12 (A) | 16 | 0.347 | 0.249 | 0.727 | 0.135 | 0.071 | 0.113 |
| 14 (A) | 1024 | 2.39 | 3.456 | 2.635 | 1.395 | 1.52 | 0.55 |

These results indicate that HGE-9 is able to complement the serological reactivity of HGE-1 and HGE-3, leading to increased sensitivity in the serodiagnosis of HGE-infection in convalescent and acute patient sera, as shown, for example, with patients 5, 8, 11 and 12 in Table 1.

EXAMPLE 3

Preparation and Characterization of Ehrlichia Fusion Proteins

A fusion protein containing the Ehrlichia antigens HGE-9, HGE-3 and HGE-1 is prepared as follows.

Each of the DNA constructs HGE-9, HGE-3 and HGE-1 are modified by PCR in order to facilitate their fusion and the subsequent expression of the fusion protein. HGE-9, HGE-3 and HGE-1 DNA was used to perform PCR using the primers PDM-225 and PDM-226 (SEQ ID NO: 74 and 75), PDM-227 and PDM-228 (SEQ ID NO: 76 and 77), and PDM-229 and PDM-209 (SEQ ID NO: 78 and 79), respectively. In each case, the DNA amplification is performed using 10 μl of 10×Pfu buffer (Stratagene), 1 μl of 12.5 mM dNTPs, 2 μl each of the PCR primers at 10 μM concentration, 82 μl water, 2 μl Pfu DNA polymerase (Stratagene, La Jolla, Calif.) and 1 μl DNA at 110 ng/μl. Denaturation at 96° C. is performed for 2 min, followed by 40 cycles of 96° C. for 20 sec, 60° C. for 15 and 72° C. for 5 min, and lastly by 72° C. for 5 min.

The HGE-9 PCR fragment is cloned into pPDM HIS at the Eco 72 I sites along with a three-way ligation of HGE-3 or HGE-1 by cutting with Pvu I. HGE-3 is cloned into pPDM HIS which has been cut with Eco 72I/Xho I. HGE-1 is cloned into pPDM HIS which has been cut with Eco 72I/Eco RI. PCR is performed on the ligation mix of each fusion with the primers PDM-225, PDM-228 and PDM-209 using the conditions provided above. These PCR products are digested with Eco RI (for HGE-1) or Xho I (for HGE-3) and cloned into pPDM HIS which is digested with Eco RI (or Xho I) and Eco 72I. The fusion construct is confirmed by DNA sequencing.

The expression construct is transformed to BLR pLys S *E. coli* (Novagen, Madison, Wis.) and grown overnight in LB broth with kanamycin (30 μg/ml) and chloramphenicol (34 μg/ml). This culture (12 ml) is used to inoculate 500 ml 2XYT with the same antibiotics and the culture is induced with IPTG. Four hours post-induction, the bacteria are harvested and sonicated in 20 mM Tris (8.0), 100 mM NaCl, 0.1% DOC, followed by centrifugation at 26,000×g. The resulting pellet is resuspended in 8 M urea, 20 mM Tris (8.0), 100 mM NaCl and bound to Ni NTA agarose resin (Qiagen, Chatsworth, Calif.). The column is washed several times with the above buffer then eluted with an imidazole gradient (50 mM, 100 mM, 500 mM imidazole is added to 8 M urea, 20 mM Tris (8.0), 100 mM NaCl). The eluates containing the protein of interest are then dialyzed against 10 mM Tris (8.0).

A fusion protein containing the Ehrlichia antigens HGE-3 and HGE-1, referred to as ErF-1, was prepared as follows.

HGE-3 and HGE-1 DNA was used to perform PCR using the primers PDM-263 and PDM-264 (SEQ ID NO: 80 and 81), and PDM-208 and PDM-265 (SEQ ID NO: 82 and 83), respectively. In both cases, the DNA amplification was performed using 10 μl of 10×Pfu buffer (Stratagene), 1 μl of 10 mM dNTPs, 2 μl each of the PCR primers at 10 μM concentration, 83 μl water, 1.5 μl Pfu DNA polymerase (Stratagene, La Jolla, Calif.) and 1 μl DNA at 50 ng/μl. Denaturation at 96° C. was performed for 2 min, followed by 40 cycles of 96° C. for 20 sec, 60° C. for 15 sec and 72° C. for 3 min, and lastly by 72° C. for 4 min. The HGE-3 PCR product was digested with Eco 721 and Xho I, and cloned into pPDM His which had been digested with Eco 721 and Xho I. The HGE-1 PCR product was digested with ScaI, cloned into the above construct at the ScaI site, and screened for orientation. The fusion construct was confirmed by DNA sequencing. The determined DNA sequence of the fusion construct is provided in SEQ ID NO: 84.

The expression construct was transformed into BL21 pLys S *E. coli* (Novagen, Madison, Wis.) and grown overnight in LB broth with kanamycin (30 μg/ml) and chloramphenicol (34 μg/ml). This culture (12 ml) was used to inoculate 500 ml 2XYT with the same antibiotics and the culture was induced with IPTG. Four hours post-induction, the bacteria were harvested and sonicated in 20 mM Tris (8.0), 100 mM NaCl, 0.1% DOC, followed by centrifugation at 26,000×g. The protein came out in the inclusion body pellet. This pellet was washed three times with a 0.5% CHAPS wash in 20 mM Tris (8.0), 300 mM NaCl. The pellet was then solubilized in 6 M GuHCl, 20 mM Tris (9.0), 300 mM NaCl, 1% Triton X-100 and batch bound to Nickel NTA resin (Qiagen). The column was washed with 100 ml 8M urea, 20 mM Tris (9.0), 300 mM NaCl and 1% DOC. This wash was repeated but without DOC. The protein was eluted with 8 M urea, 20 mM Tris (9.0), 100 mM NaCl and 500 mM imidazole. In a second elution, the imidazole was increased to 1 M. The elutions were run on a 4–20% SDS-PAGE gel and the fractions containing the protein of interest were pooled and dialyzed against 10 mM Tris (9.0). The amino acid sequence of the fusion protein ErF-1 is provided in SEQ ID NO: 85.

One of skill in the art will appreciate that the order of the individual antigens within the fusion protein may be changed and that comparable or enhanced activity could be expected provided each of the epitopes is still functionally available. In addition, truncated forms of the proteins containing active epitopes may be used in the construction of fusion proteins.

Table 2 provides representative data from studies of the reactivity of ErF-1, HGE-1 or HGE-3 with both IgG and IgM in sera from patients with acute (A) or convalescent (C) HGE, determined as described above in Example 2. The antibody titer for each patient, as determined by immunofluorescence, is also provided.

TABLE 2

| Patient | HGE | IgG | | | IgM | | |
|---|---|---|---|---|---|---|---|
| ID | titer | HGE-1 | HGE-3 | ErF-1 | HGE-1 | HGE-3 | ErF-1 |
| 1 (A) | 128 | 0.346 | 0.154 | 0.114 | 0.067 | 0.028 | 0.149 |
| 2 (A) | 1024 | 1.539 | 1.839 | 1.911 | 2.75 | 3.256 | 1.916 |
| 3 (A) | <16 | 0.412 | 0.16 | 0.096 | 0.043 | 0.088 | 0.104 |
| 4 (A) | <16 | 0.436 | 0.072 | 0.111 | 0.017 | 0.032 | 0.081 |
| 5 (C) | 256 | 0.322 | 0.595 | 0.713 | 0.229 | 0.345 | 0.190 |
| 6 (A) | 512 | 1.509 | 2.042 | 1.945 | 0.721 | 0.695 | 0.314 |
| 7 (C) | 512 | 0.508 | 1.019 | 1.206 | 0.45 | 0.777 | 0.361 |
| 8 (C) | 128 | 0.635 | 0.979 | 1.212 | 0.729 | 2.079 | 0.551 |
| 9 (C) | 256 | 0.408 | 0.74 | 0.767 | 0.052 | 0.11 | 0.157 |
| 10 (A) | 64 | 0.579 | 0.133 | 0.116 | −0.002 | 0.015 | 0.052 |
| 11 (A) | 256 | 0.13 | 0.066 | 0.039 | −0.018 | 0.003 | 0.022 |
| 12 (A) | 16 | 0.347 | 0.249 | 0.063 | 0.135 | 0.071 | 0.032 |
| 14 (A) | 1024 | 2.39 | 3.456 | 2.814 | 1.395 | 1.52 | 0.773 |

Table 3 shows the sensitivity and specificity of the reactivity of ErF-1, HGE-9, ErF-1 plus HGE-9, HGE-2, HGE-14, HGE-15 or HGE-17, with both IgG and IgM in sera from patients with acute (A) or convalescent (C) HGE, determined by ELISA as described above in Example 2. The theoretical results for a combination of ErF-1, HGE-9, HGE-2, HGE-14, HGE-15 and HGE-17 are also shown in Table 3. With the combination of all the recombinant antigens, 85.2% of the acute phase serum samples and 96.7% of the convalescent phase samples were detected, with a specificity of greater than 90%.

TABLE 3

| | Sensitivity | | |
|---|---|---|---|
| | Acute | Convalescent | Specificity |
| ErF-1 | | | |
| IgG | 14/27 (51.8%) | 25/27 (92/6%) | 97.2% (1/36) |
| IgM | 15/27 (55.6%) | 23/27 (85.2%) | 100% (0/36) |
| IgG + IgM | 15/27 (55.6%) | 25/27 (92.6%) | 97.2% (1/36) |
| HGE-9 | | | |
| IgG | 18/27 (66.7%) | 19/26 (73.1%) | 97.3% (1/37) |
| IgM | 12/27 (44.4%) | 18/26 (69.2%) | 100% (0/37) |
| IgG + IgM | 20/27 (74.1%) | 20/26 (76.9%) | 97.3% (1/37) |
| ErF-1 + HGE-9 | | | |
| IgG | 19/27 (70.4%) | 25/27 (92.6%) | |
| IgM | 16/27 (59.2%) | 23/27 (85.2%) | |
| IgG + IgM | 20/27 (77.8%) | 25/27 (92.6%) | |
| HGE-2 | | | |
| IgG | 15/27 (55.6%) | 21/26 (80.8%) | 97.3% (1/37) |
| IgM | 4/27 (14.8%) | 3/26 (11.5%) | 94.6% (2/37) |
| IgG + IgM | 15/27 (55.6%) | 21/26 (80.8%) | 91.9% (3/37) |
| HGE-14 | | | |
| IgG | 13/27 (48.1%) | 13/26 (50.0%) | 96.8% (1/31) |
| IgM | 8/27 (29.6) | 7/26 (26.9%) | 93.5% (2/31) |
| IgG + IgM | 14/27 (51.8%) | 13/26 (50.0%) | 93.5% (2/31) |
| HGE-15 | | | |
| IgG | 12/27 (44.4%) | 17/26 (65.4%) | 97.3% (1/37) |
| IgM | 12/27 (44.4%) | 13/26 (4850.0%%) | 97.3% (1/37) |
| IgG + IgM | 13/27 (48.1%) | 18/26 (69.2%) | 94.6% (2/37) |
| HGE-17 | | | |
| IgG | 12/27 (44.4%) | 13/26 (50.0%) | 94.6% (2/37) |
| IgM | 14/27 (51.8%) | 14/26 (53.8%) | 100% (0/37) |
| IgG + IgM | 15/27 (55.6%) | 18/26 (69.2%) | 94.6% (2/37) |

TABLE 3-continued

| | Sensitivity | | |
|---|---|---|---|
| | Acute | Convalescent | Specificity |
| ALL ANTIGENS | | | |
| IgG | 21/27 (77.8%) | 26/27 (96.3%) | |
| IgM | 16/27 (59.2%) | 22/27 (81.5%) | |
| IgG + IgM | 23/27 (85.2%) | 26/27 (96.2%) | |

EXAMPLE 4

Preparation of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide comprising an amino acid sequence selected from the group consisting of:

(a) sequences encoded by the polynucleotide of SEQ ID NO: 84;

(b) sequences having at least 70% identity to a sequence encoded by SEQ ID NO: 84; and (c) sequences having at least 90% identity to a sequence encoded by SEQ ID NO: 84;

wherein the polypeptide possesses an ability to react with antisera raised against a polypeptide of SEQ ID NO: 85.

2. The polypeptide of claim 1, wherein the polypeptide comprises the amino acid sequence of SEQ ID NO: 85.

3. A composition comprising a first component selected from the group consisting of physiologically acceptable carriers and immunostimulants, and a second component comprising one or more polypeptides according to any one of claim 1 or claim 2.

* * * * *